(12) United States Patent
Grayson

(10) Patent No.: US 12,087,564 B2
(45) Date of Patent: *Sep. 10, 2024

(54) TUNED SYNTHETIC DENDRIMER CALIBRANTS FOR MASS SPECTROMETRY

(71) Applicant: The Administrators of the Tulane Educational Fund, New Orleans, LA (US)

(72) Inventor: Scott Grayson, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 83 days.

This patent is subject to a terminal disclaimer.

(21) Appl. No.: 17/557,879

(22) Filed: Dec. 21, 2021

(65) Prior Publication Data

US 2022/0384167 A1    Dec. 1, 2022

Related U.S. Application Data

(60) Continuation of application No. 16/457,033, filed on Jun. 28, 2019, now Pat. No. 11,217,435, which is a division of application No. 14/402,474, filed as application No. PCT/US2013/042110 on May 21, 2013, now Pat. No. 10,347,476.

(60) Provisional application No. 61/649,920, filed on May 21, 2012.

(51) Int. Cl.
*H01J 49/00* (2006.01)
*C07D 319/06* (2006.01)
*C07D 493/22* (2006.01)

(52) U.S. Cl.
CPC ........ *H01J 49/0009* (2013.01); *C07D 319/06* (2013.01); *C07D 493/22* (2013.01); *H01J 49/004* (2013.01); *Y10T 436/10* (2015.01)

(58) Field of Classification Search
None
See application file for complete search history.

(56) References Cited

FOREIGN PATENT DOCUMENTS

WO    WO 2010/091109    *  8/2010    ........... C07D 319/06

* cited by examiner

*Primary Examiner* — Xiaoyun R Xu
(74) *Attorney, Agent, or Firm* — MARSHALL, GERSTEIN & BORUN LLP

(57) ABSTRACT

Provided are synthetic dendrimer calibrants for mass spectrometry. The calibrants are distinguished by their relative case and rapidity of synthesis, comparatively low cost, long shelf life, high purity, and amenability to batch synthesis as mixtures. The latter characteristic enables parallel preparation of higher molecular weight compounds displaying useful distributions of discrete molecular weights, thereby providing multi-point mass spectrometry calibration standards. Methods of making, tuning and using said calibrants are provided.

20 Claims, 31 Drawing Sheets

TUNED SYNTHETIC DENDRIMER CALIBRANTS FOR MASS SPECTROMETRY

CROSS-REFERENCE TO RELATED APPLICATIONS

This application is a continuation of U.S. application Ser. No. 16/457,033 filed Jun. 28, 2019, which is a division of U.S. application Ser. No. 14/402,474, filed Nov. 20, 2014, which is a U.S. national stage entry of International Application No. PCT/US2013/042110, filed May 21, 2013, which claims the priority benefit of U.S. Provisional Application No. 61/649,920, filed May 21, 2012, all of which are incorporated herein by reference in their entireties.

BACKGROUND

1. Field

The present disclosure relates to dendritic molecules having serially-branched structure wherein at least one of the branches possesses a second branching structure. The present disclosure also comprises methods for the preparation of said dendritic molecules, their use as calibrants for time-of-flight matrix-assisted laser desorption/ionization (MALDI-TOF) mass spectrometry (MS), electrospray ionization (ESI-MS), atmospheric pressure chemical ionization (APCI-MS), fast atom bombardment (FAB-MS), and other MS techniques for the analysis of compounds with molecular weights greater than 1000 Daltons. The present disclosure further relates to the tuning of dendritic molecules, the method of preparation of said tuned dendritic molecules, and their use as calibrants.

2. Description of Related Art

Mass spectrometry (MS) is an analytical technique for determining the elemental composition of samples (e.g., proteins, chemical compounds, etc.). It may also be used in determining the chemical structures of such samples. Generally, MS comprises ionizing a sample to generate charged molecules (and fragments thereof), and measuring their mass-to-charge ratios.

Time-of-flight mass spectrometry (TOF-MS) is a method in which ions are accelerated by an electric field into a field-free drift region with a kinetic energy of qV, where q is the ion charge and V is the applied voltage. Since each ion's kinetic energy is $\frac{1}{2}mv^2$, where x is mass and v is velocity, lighter ions have a higher velocity than heavier ions. Thus, the lighter ions reach the detector at the end of the drift region sooner than the heavier ions. Matrix-assisted laser desorption/ionization (MALDI) is an ionization technique used in mass spectrometry, which facilitates the analysis of biomolecules (e.g., proteins, peptides, and sugars) and large organic molecules (e.g., polymers and other macromolecules).

Electrospray ionization (ESI) is an atmospheric pressure ionization technique whereby an analyte, dissolved in volatile solvent (e.g., acetonitrile, $CH_3OH$, $CH_3Cl$, water, etc.), is forced through a small, charged capillary (usually metal). The analyte exists as an ion in solution, and as the sample is forced out of the capillary it aerosolizes. This increases the distance between the similarly-charged analyte particles. A neutral gas carrier (e.g., nitrogen) is often used to evaporate the solvent from the droplets. As the solvent evaporates, the charged analyte molecules are brought closer together. At the same time, though, the like charge on the analyte molecules forces them apart. This process of contraction and expansion repeats until the sample is free of solvent and is a lone ion. The lone ion then proceeds to the mass analyzer.

Atmospheric pressure chemical ionization (APCI) is also an atmospheric pressure ionization technique, whereby a sample solution passing through a heated tube (e.g., greater than 400° C.) is volatilized and subjected to a corona discharge with the aid of nitrogen nebulization. APCI is a variant of ESI, and can be performed in a modified ESI source. Ions, produced by the discharge, are extracted into the mass spectrometer. This technique is best for relatively polar, semi-volatile samples, and may be used as a liquid chromatography-mass spectrometry (LC/MS) interface because if can accommodate very high liquid flow rates (e.g., 1 mL/min). Spectra from APCI-MS usually contain the quasi-molecular ion $[M+H]^+$.

Fast atom bombardment (FAB) employs a high-energy beam of neutral atoms, typically xenon or argon, which strikes a solid sample (analyte mixed with matrix) under vacuum to cause desorption and ionization. Common matrices include glycerol, thioglycerol, 3-nitrobenzyl alcohol (3-NBA), 18-Crown6 ether, 2-nitrophenyloctyl ether, sulfolane, diethanolamine, and triethanolamine. FAB is used for large biological molecules that are difficult to get into the gas phase. The high-energy beam is produced by accelerating ions from an ion source through a charge-exchange cell. Those ions accumulate an electron through collisions with neutral atoms, to form a beam of high-energy atoms. Because FAB spectra often contain only a few fragments, and a signal for the pseudo molecular ion (e.g., $[M+H]^+$, $[M+Na]^+$), it is useful for determining molecular weights. The low m/z region, though, is usually crowded with signals from the matrix.

In order to calibrate mass spectrometers for a range of analytical work, including protein, peptide, oligonucleotide, and synthetic polymer characterization and structural determination, known calibrants of a diverse set of molecular weights are required. Typically, proteins and peptides have been used because of their monodispersity (only a single and exact molecular weight is present in a pure sample) al their availability from biological sources. Examples include: bradykinin, adrenocorticotropic hormone, insulin chain B, cytochrome c, apomyoglobin, albumin, aldolase, and angiotensin H. However, the production—and particularly the purification—of such standards is time consuming and technically complicated, leading to a fairly high expense for gram quantities. In addition, such standards have inherently poor shelf-life due to enzymatic instability and acid sensitivity.

Synthetic polymers offer a much cheaper alternative, but exist as a broad distribution of molecular weights because they are prepared using a relatively unmediated reaction between single monomer units (compared to biological syntheses) that inevitably result in a statistical distribution of molecular weights. This broad distribution of molecular weights is typically observed in mass spectra as a Gaussian series of peaks, evenly spaced as multiples of the monomer mass. However, the development of efficient dendrimer syntheses offers to marry the cheap scalable cost of synthetic materials with the exact molecular weight traditionally associated with biosynthesized materials.

Two contrasting synthetic routes towards the preparation of "true" dendrimers (highly branched, molecules with a high degree of structural regularity) are known.

The first approach—the divergent approach—first involves the coupling of a branched monomer to a core molecule, yielding an intermediate, and then "activation" of the intermediate to produce a new, larger molecule with an enhanced number of surface functionalities. Repetition of these two steps leads to outward, layer-by-layer growth of dendritic molecules having exponentially increasing size.

The second approach—the convergent approach—involves peripheral groups which are tethered via one monomer unit, producing "wedges" or "dendrons." Two of these dendrons may be coupled with an additional monomer molecule to make a larger dendron, and growth continues inward, layer by layer, until coupled to a core.

Typically, divergent techniques are technically simple: a large excess of a small molecule reacts with the growing molecule, and then is removed (e.g., by distillation), providing a relatively cost-efficient and scalable synthesis. With divergent techniques, however, the number of coupling reactions increases exponentially with each generation. Consequently, dendrimers with minor structural impurities are nearly inevitable and cannot be easily removed (e.g., when n is a large number, the product of n coupling reactions has physical properties nearly identical to the product of n−1 couplings). The result is poorly-defined materials for applications such as MS calibration.

Convergent techniques have the distinct advantage that each coupling involves a small and constant number of reactions (usually 2 or 3 reactions). Thus, with convergent techniques the reactions can be driven to completion and any impurities generated by side reactions are easily detected (since n is small) and removed. But while the materials produced with convergent techniques are well-defined, their synthesis is demanding. This prevents their economical use for all but specialty applications.

The technical problem underlying the present disclosure was therefore to overcome these prior art difficulties by providing monodisperse calibrants with improved shelf-life, at lower cost, and over a broad range of molecular weights. The solution to this technical problem is provided by the embodiments characterized in the claims.

BRIEF SUMMARY

The present disclosure relates to dendritic molecules—dendrimers—useful for calibration of mass spectrometry instruments, and particularly useful in MALDI-TOF, ESI, APCI, and FAB mass spectrometry techniques and any additional technique used for mass analysis of materials with molecular weights above 1,000 daltons. The present disclosure also relates to methods of synthesizing said dendrimers, as well as methods of using them.

The disclosure relates, in one aspect, to synthetic calibrants. The synthetic calibrants of the present disclosure are dendritic molecules—dendrimers—synthesized ("generated") via "dendronization" of a hydroxyl-terminated core molecule and, optionally, a subsequent "deprotection" step. Also optionally, the dendronization and deprotection steps may be performed multiple times (wherein each deprotection step follows a dendronization step, and wherein each dendronization step after the first dendronization step follows a deprotection step) to yield dendrimers of known and useful sizes. The dendrimer products of each round of dendronization/deprotection are part of the same "generation."

For example, the first dendronization step performed with a core molecule yields a first generation, or "G-1" dendrimer. Likewise, the next deprotection step performed on the resulting G-1 dendrimer also yields a first generation dendrimer. The dendronization step after the G-1 deprotection step, however, leads to a second generation, or "G-2" dendrimer. Thus, each round of dendronization and deprotection yield dendrimer products of the same "generation."

In a preferred embodiment, the disclosure relates to a mixture of dendrimers of different molecular weights, and especially to a specifically proportioned mixture (e.g., an equimolar mixture) of said dendrimers. In particular, the present disclosure relates to a mixture of dendrimers synthesized in parallel, wherein equimolar quantities of core molecules bearing different numbers of alcohol functionalities are mixed together and subjected to at least one round of dendronization. Optionally, the resulting mixture may be subjected to several rounds of dendronization and deprotection to yield dendrimer mixtures of known and useful sizes, across a broad spectrum of molecular weights. In each of these mixtures, the dendrimers are of the same generation and all are useful in mass spectrometry. Additionally, because the end groups can be modified by dendronization and deprotection, the dendrimers of the present disclosure possess high solubility in nearly the full spectrum of solvents, matrices, and analytes useful for MS. Consequently, the dendrimers of the present disclosure are useful as internal calibrants (i.e., they may be mixed directly with the analyte and matrix during sample preparation).

In one embodiment, a composition is provided comprising a first dendrimer comprising a first core molecule, wherein said first core molecule is selected from the group consisting of: a molecule comprising between 1 and 8 alcohol functionalities, a molecule comprising between 1 and 8 amine functionalities, and a molecule comprising at least one amine functionality and at least one alcohol functionality wherein the combined number of amine and alcohol functionalities of said first core molecule is at least 2 but no greater than 8; a second dendrimer comprising a second core molecule, wherein said second core molecule is selected from the group consisting of: a molecule comprising between 1 and 8 alcohol functionalities, a molecule comprising between 1 and 8 amine functionalities, and a molecule comprising at least one amine functionality and at least one alcohol functionality wherein the combined number of amine and alcohol functionalities of said second core molecule is at least 2 but no greater than 8; and wherein said first core molecule has a different number of total alcohol functionalities and amine functionalities than said second core molecule.

In another embodiment, a composition is provided comprising a first dendrimer comprising a first core molecule, wherein said first core molecule is selected from the group consisting of: a molecule comprising between 1 and 8 alcohol functionalities, a molecule comprising between 1 and 8 amine functionalities, and a molecule comprising at least one amine functionality and at least one alcohol functionality wherein the combined number of amine and alcohol functionalities of said first core molecule is at least 2 but no greater than 8; and a second dendrimer comprising a second core molecule, wherein said second core molecule comprises a subsequent generation dendrimer of said first core molecule.

In yet another embodiment, a method of manufacturing is provided comprising the steps of: providing a composition comprising a first core molecule wherein said first core molecule is selected from the group consisting of: a molecule comprising between 1 and 8 alcohol functionalities, a molecule comprising between 1 and 8 amine functionalities, and a molecule comprising at least one amine functionality and at least one alcohol functionality wherein the combined number of amine and alcohol functionalities of said first core molecule is at least 2 but no greater than 8; a second core molecule wherein said second core molecule is selected from the group consisting of: a molecule comprising between 1 and 8 alcohol functionalities, a molecule comprising between 1 and 8 amine functionalities, a molecule comprising at least one amine functionality and at least one alcohol functionality wherein the combined number of amine and alcohol functionalities of said second core molecule is at least 2 but no greater than 8; and wherein said first core molecule has a different number of total alcohol functionalities and amine functionalities than said second core molecule; and subjecting said first core molecule and said second core molecule to a round of dendronization.

In yet another embodiment a method of manufacturing is provided comprising the steps of providing a composition comprising a first dendrimer comprising a first core molecule, wherein said first core molecule is selected from the group consisting of: a molecule comprising between 1 and 8 alcohol functionalities, a molecule comprising between 1 and 8 amine functionalities, and a molecule comprising at least one amine functionality and at least one alcohol functionality wherein the combined number of amine and alcohol functionalities of said first core molecule is at least 2 but no greater than 8; and a second dendrimer comprising a second core molecule, wherein said second core molecule comprises a subsequent generation dendrimer of said first core molecule; and subjecting said first core molecule and said second core molecule to a round of dendronization.

In yet another embodiment a method of determining physical properties of a sample is provided, the method comprising: providing a composition comprising a first dendrimer comprising a first core molecule, wherein said first core molecule is selected from the group consisting of: a molecule comprising between 1 and 8 alcohol functionalities, a molecule comprising between 1 and 8 amine functionalities, and a molecule comprising at least one amine functionality and at least one alcohol functionality wherein the combined number of amine and alcohol functionalities of said first core molecule is at least 2 but no greater than 8; a second dendrimer comprising a second core molecule, wherein said second core molecule is selected from the group consisting of: a molecule comprising between 1 and 8 alcohol functionalities, a molecule comprising between 1 and 8 amine functionalities, and a molecule comprising at least one amine functionality and at least one alcohol functionality wherein the combined number of amine and alcohol functionalities of said second core molecule is at least 2 but no greater than 8; wherein said first core molecule has a different number of total alcohol functionalities and amine functionalities than said second core molecule; and wherein said composition has physical properties; ionizing at least a portion of said composition; providing an analyte sample wherein said analyte sample has physical properties; ionizing at least a portion of said analyte; collecting data from said ionized portion of said composition and said ionized portion of said analyte sample; and relating said data to said physical properties of said portion of said composition, thereby determining said physical properties of said analyte sample.

In yet another embodiment a method of determining physical properties of a sample is provided, the method comprising providing a composition comprising a first dendrimer comprising a first core molecule, wherein said first core molecule is selected from the group consisting of: a molecule comprising between 1 and 8 alcohol functionalities, a molecule comprising between 1 and 8 amine functionalities, and a molecule comprising at least one amine functionality and at least one alcohol functionality wherein the combined number of amine and alcohol functionalities of said first core molecule is at least 2 but no greater than 8; a second dendrimer comprising a second core molecule, wherein said second core molecule comprises a subsequent generation dendrimer of said first core molecule; and wherein said composition has physical properties; ionizing at least a portion of said composition; providing an analyte sample wherein said analyte sample has physical properties; ionizing at least a portion of said analyte; collecting data from said ionized portion of said composition and said ionized portion of said analyte sample; and relating said data to said physical properties of said portion of said composition, thereby determining said physical properties of said analyte sample.

In yet another embodiment, a method of calibrating a mass spectrometer is provided, the method comprising providing a composition comprising a first dendrimer comprising a first core molecule, wherein said first core molecule is selected from the group consisting of: a molecule comprising between 1 and 8 alcohol functionalities, a molecule comprising between 1 and 8 amine functionalities, and a molecule comprising at least one amine functionality and at least one alcohol functionality wherein the combined number of amine and alcohol functionalities of said first core molecule is at least 2 but no greater than 8; a second dendrimer comprising a second core molecule, wherein said second core molecule is selected from the group consisting of: a molecule comprising between 1 and 8 alcohol functionalities, a molecule comprising between 1 and 8 amine functionalities, and a molecule comprising at least one amine functionality and at least one alcohol functionality wherein the combined number of amine and alcohol functionalities of said second core molecule is at least 2 but no greater than 8; wherein said first core molecule has a different number of total alcohol functionalities and amine functionalities than said second core molecule; and wherein said composition has physical properties; ionizing at least a portion of said composition; collecting data from said ionized portion of said composition; and relating said data to said physical properties.

In yet another embodiment, a method of calibrating a mass spectrometer is provided, the method comprising: providing a composition comprising a first dendrimer comprising a first core molecule, wherein said first core molecule is selected from the group consisting of: a molecule comprising between 1 and 8 alcohol functionalities, a molecule comprising between 1 and 8 amine functionalities, and a molecule comprising at least one amine functionality and at least one alcohol functionality wherein the combined number of amine and alcohol functionalities of said first core molecule is at least 2 but no greater than 8; a second dendrimer comprising a second core molecule, wherein said second core molecule comprises a subsequent generation dendrimer of said first core molecule, and wherein said composition has physical properties; ionizing at least a portion of said composition; collecting data from said ionized portion of said composition; and relating said data to said physical properties.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

DETAILED DESCRIPTION

Figure 1:
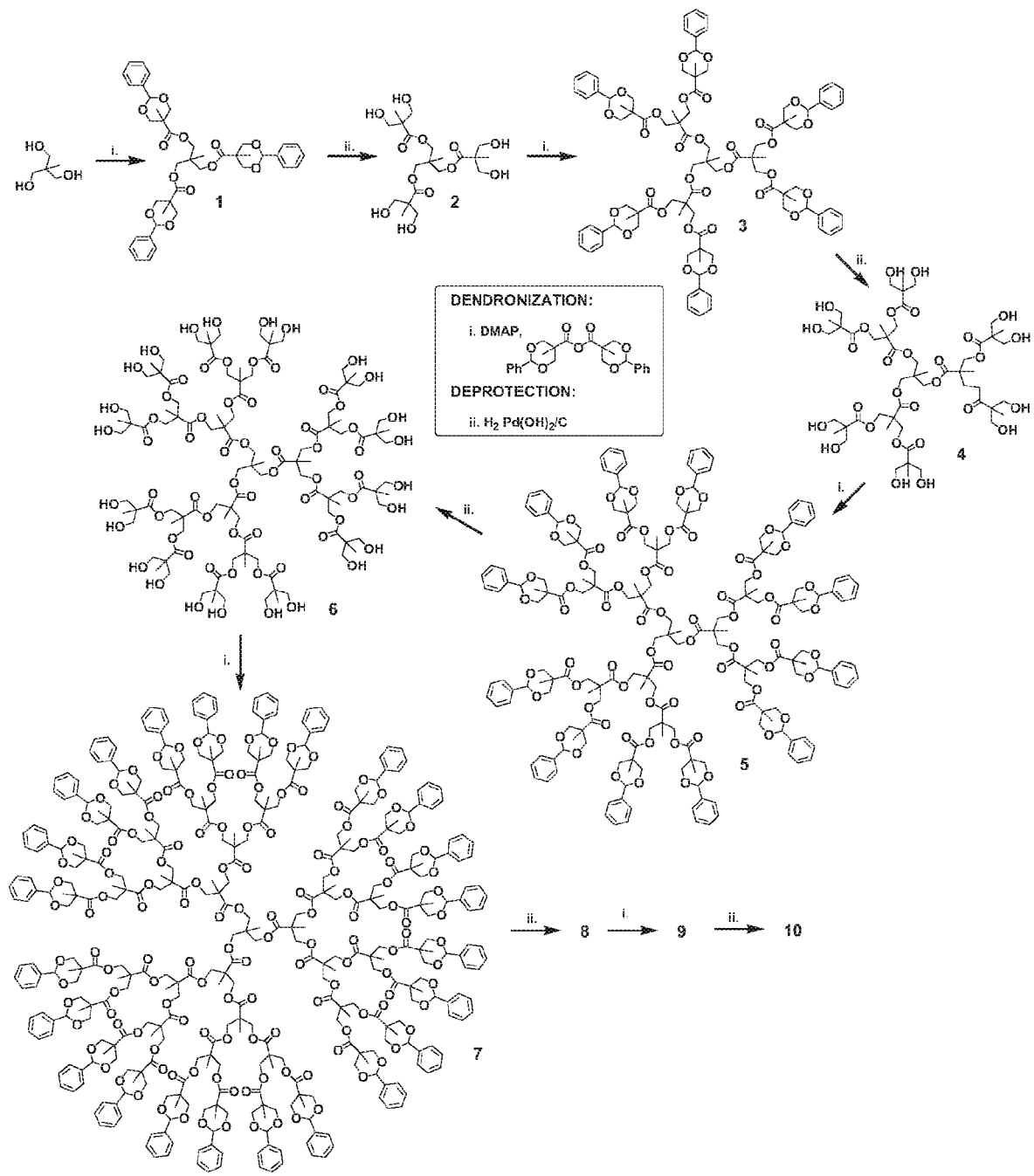
FIG. 1 is a schematic diagram showing the synthesis of tri-functional "C-3" calibrants of the present disclosure.

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

Furthermore, this application incorporates by reference, in their entireties, U.S. Non-Provisional application Ser. No. 11/290,998, which is the National Stage of International Application No. PCT/US10/23087 filed on 3 Feb. 2012, U.S. Provisional Patent Application No. 61/149,506, filed 3 Feb. 2009, U.S. Provisional Patent Application No. 61/167,708, filed on 8 Apr. 2009, and U.S. Provisional Patent Application No. 61/185,665, filed on 10 Jun. 2009.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

As used herein, the term "[M+Ag]" indicates that one silver cation is attached per molecule, during ionization of samples, as the counterion. Other counterions may include, for example and without limitation, "H", "Na", and "K", as will be readily appreciated by those persons having ordinary skill in the relevant art. As used herein, the term "m/z" denotes the mass-to-charge ratio. As used herein, "MW" means molecular weight.

The recently developed divergent aliphatic poly(ester) synthesis appears to offer the advantages of both techniques, while minimizing the shortcomings of both. A divergent dendritic synthesis is an iterative process that involves a well-defined (though exponential) increase of mass with each repetition of two synthetic steps: the "coupling step," and the "deprotection step." In FIG. 1, for example, the "coupling step" (e.g., step "i" in FIG. 1) involves reaction of a specific number of alcohol functionalities (—OH groups) from the core structure with the benzylidene protected bis-MPA acid anhydride (IUPAC name bis(5-methyl-2-phenyl-1,3-dioxane-5-carboxylic) acid anhydride monomer ("monomer" in FIG. 1) In doing so, an exact number of monomer units are connected to the core molecules, yielding a new dendritic molecule with a discrete molecular weight. In the "deprotection step" (e.g., step "ii" of FIG. 1), a palladium catalyst (palladium(II) hydroxide supported on graphite, also known as Pearlman's catalyst) is used to remove the benzylidene protecting groups via a hydrogenolysis reaction to generate a new core. It should be noted that in doing so, the number of alcohol functionalities doubles after carrying out each iteration of coupling and deprotection, thus enabling the process to be repeated and the structures to grow exponentially—but in a well controlled fashion—and so yielding monodisperse products. Because the coupling step involves the clean, highly activated esterification reaction of alcohol functional groups with acid anhydrides, the reaction can be carried out in "quantitative" yields (greater than 99.9%), without byproduct. In addition, a number of deprotection steps (e.g. palladium ("Pd") catalyzed hydrogenolysis and acid catalyzed hydrolysis for the corresponding benzylidene and acetal protected monomer) can be carried out in an equally clean and quantitative fashion, providing monodisperse compounds sufficiently pure to act as calibrants for mass spectrometry. At the same time, this divergent approach offers a fast route that is technically simple without chromatographic purification, enabling cost-efficient, scalable production.

The synthetic dendrimer calibrants of the present disclosure offer a number of distinct advantages over other calibrants. Peptides and proteins have been used as commercial standards for calibration because, traditionally, these were the only monodisperse polymers which could be prepared and purified with sufficiently high molecular weight. While peptide and protein calibrants provide a viable standard, they suffer from short shelf-life (because of the prevalence of peptidases) and high cost (because their synthesis and purification is typically carried out on a milligram scale). A representative example of these calibrants is provided in TABLE 1.

TABLE 1

Prior Art Peptide and Protein Calibrants

| Calibrant | Molecu Weight | Price per (USD) |
|---|---|---|
| Bradykinin Fragment | 756 | 38,300 |
| Angiotensin II | 1,046 | 6,580 |
| PnR | 1,533 | 8,733,300 |

TABLE 1-continued

Prior Art Peptide and Protein Calibrants

| Calibrant | Molecu Weight | Price per (USD) |
|---|---|---|
| ACTH Fragment 18- | 2,464 | 220,500 |
| Insulin Chain B | 3,496 | 8,160 |
| Insulin | 5,730 | 2,652,900 |
| Cytochrome c | 12,362 | 1,181,000 |
| Apomyoglobin | 16,952 | 861,200 |
| Aldolase | 39,211 | 372,300 |
| Albumin | 66,429 | 219,800 |

Source: Sigma-Aldrich, Inc.

Synthetic calibrants offer a number of potential advantages, including increased shelf-life, but until recently the only products that could be produced at a competitive price were polydisperse polymers (i.e., they exhibit a broad range of mass characteristics). The presence of multiple species (and the prevalence of different counterions in MS, including MALDI-TOF, ESI, APCI, and FAB) has prevented these from becoming an attractive alternative to peptides and proteins. Monodisperse synthetic calibrants, such as $P_{14}R$, are at least 3 times as expensive as the next-cheapest peptide calibrant (Insulin), and more than 1,000 times more expensive than the cheapest peptide calibrant (Insulin Chain B).

The synthetic dendrimer calibrants of the present disclosure, in contrast, are less expensive to produce. Because of this rapid synthetic access to cost-efficient, yet highly pure dendritic compounds, the dendrimer calibrants of the present disclosure offer a competitive solution to the calibration of mass spectrometers, particularly when using MALDI-TOF, ESI, APCI, or FAB methods. In addition, they can be synthesized as mixtures, thus reducing preparation, purification, and packaging costs. While presently-available peptide and protein calibrants are widely used and accepted, the reduced cost of the dendrimer calibrants of the present disclosure, as well as their improved shelf-life and solvent compatibility, should result in their ready acceptance.

The dendrimers are given a standard nomenclature to denote their architecture. For example, in the names "CX-([G-n]Ph$_p$)$_2$," and "CX-([G-n]OH$_q$)$_2$" the "CX" term refers to the number of alcohol functionalities on the core—the "core number"—where "X" is an integer. Thus, "C3" refers to 1,1,1-trishydroxyethylmethane (a triol) as the core, "C4" refers to pentaerythritol (a tetraol) as the core, "C5" refers to xylitol (a pentaol) as the core, and C6 refers to dipentaerythritol (a hexaol) as the core. The "G-n" term refers to the generation number, which denotes the number of layers of branching points which have been added, and which also refers to the number of coupling-and-deprotection iterations that have taken place. For example, "[G-1]" denotes "generation one," and indicates that one round of coupling has occurred (see, e.g., dendrimer 1 of FIG. 1: "C3-([G-1]Ph)$_3$") or that one round of coupling-and-deprotection has occurred (see, e.g., dendrimer 2 of FIG. 1: "C3-([G-1]OH$_2$)$_3$"). In other words, dendrimers 1 and 2 are of the same generation: generation one, or "G-1". Each of the initiating alcohols bears a wedge shaped dendritic moiety, referred to as a "dendron." The end groups (per dendron) are noted by either Ph$_p$, for the benzylidene protected structures (where "p" has a value of $2^{n-1}$), or OH$_q$, for the hydroxylated structures (where "q" has a value of 2), and where "p" and "q" denote the number of the end groups per dendron (per wedge-shaped dendritic moiety). Finally, the number of dendrons per core, which corresponds to the core number, is denoted by "z".

Example 1

General Synthetic Procedure

The general procedure for the preparation of the dendritic calibrants follows generally those published by Grayson et al. (Grayson, S. M.; Fréchet, J. M. J. *Macromolecules*, 2001; 34:6542-6544) and by Ihre et al. (Ihre, H.; Padilla de Jesus, O. L; Fréchet, J. M. J *J. Am. Chem. Soc.* 2001; 123:5908-5917), each of which are hereby incorporated by reference in their entireties.

As shown in FIG. 1, the dendritic synthesis involves the repetition of two critical steps: i) the dendritic growth or "dendonization" step, in which a "protected" monomer is attached to every active peripheral functionality; and ii) the activation or "deprotection" step, in which each monomer is altered to expose an increased multiplicity of active functionalities on the surface. Serial repetitions of these two steps lead to the exponential increase in both peripheral functional groups and molecular weight.

Example 2

Preparation of Benzylidene Protected Bis-MPA Anhydride Monomer

The benzylidene protected bis-MPA anhydride monomer was prepared according to the synthesis reported previously by Ihre, H.; Padilla de Jesus, O. L.; Fréchet, J. M. J *J. Am. Chem. Soc.* 2001, 123, 5908-5917, which is hereby incorporated by reference in its entirety.

Example 3

General Dendronization Procedure for Preparation of CX-([G-n]Ph$_p$)$_z$

The procedure of this EXAMPLE is shown schematically as step "i" of FIG. 1 (e.g., the syntheses of: dendrimer 1 from hydroxyl-terminated core; of dendrimer 3 from dendrimer 2; etc.). To a round bottom flask were added: a known quantity of either hydroxyl-terminated core (e.g., 1,1,1-tris(hydroxymethyl)ethane, pentaerythritol, xylitol, or dipentaerythritol) or of dendrimer (e.g., one having the general formula CX-([G-(n−1)]OH$_r$)$_z$, where "r" has a value of $2^{(n-1)}$, as appropriate; 1.1 equivalents (per —OH of hydroxyl-terminated core or of dendrimer) of the benzylidene protected bis-MPA anhydride monomer (bis(5-methyl-2-phenyl-1,3-dioxane-5-carboxylic) acid anhydride monomer); and 0.1 molar equivalents (per —OH of hydroxyl-terminated core or of dendrimer) of 4-dimethylaminopyridine (DMAP). The reaction mixture was dissolved in the minimum amount of pyridine, diluted in twice that amount (relative to pyridine) of dichloromethane, and the reaction mixture was then stirred vigorously for 4 hours at standard temperature and pressure. The reaction was monitored periodically by MALDI-TOF MS to determine the degree of coupling. After complete esterification was observed by MALDI-TOF MS, the flask contents were transferred to a separatory funnel, diluted with dichloromethane, extracted three times with 1M aqueous NaHSO$_4$ (sodium bis sulfate) and three extractions with 1M aqueous NaHCO$_3$ (sodium bicarbonate). The organic layers were reduced in vacuo to concentrate the sample, precipitated into hexanes, and filtered to yield the benzylidene protected dendrimers, CX-([G-n]Ph$_p$)$_z$, as a white powdery precipitate. The resulting precipitate may then be prepared for spectrometric analysis via standard protocols.

Example 4

General Deprotection Procedure for Preparation of CX-([G-n]OH$_q$)$_z$

The procedure of this EXAMPLE is shown schematically as step "ii" of FIG. 1 (e.g., the syntheses of: dendrimer 2 from dendrimer 1; of dendrimer 4 from dendrimer 3; etc.). To a round bottom flask, a measured quantity of CX-([G-n]Ph$_r$)$_z$, where "r" has a value of $2^{(n-1)}$ was added and dissolved in a sufficient amount of a 2:1 solution of dichloromethane:methanol. Pearlman's catalyst (Pd(OH)$_2$/C) was added to the reaction mixture, and the flask contents were placed under 8 atmospheres (atm) of hydrogen gas. The reaction mixture was stirred vigorously for 24 hours at room temperature. Full deprotection was verified by crude MALDI MS data, after which the Pd(OH)$_2$/C was removed via filtration over Celite®. The filtrate was then reduced in vacuo to yield a transparent glassy solid having the formula CX-([G-n]OH$_q$)$_z$. The resulting filtrate may then be prepared for spectrometric analysis via standard protocols.

Example 5

Synthesis of Tri-Functional "C-3" Calibrants

The tri-functional dendrimer species of this EXAMPLE 5 are shown in FIG. 1.

Synthesis of C3-([G-1]Ph)$_3$, dendrimer 1 of FIG. 1: 1,1,1-tris(hydroxymethyl)ethane (IUPAC name: 2-(hydroxymethyl)-2-methylpropane-1,3-diol), which is commercially available, was esterified following the General Dendronization Procedure of EXAMPLE 3, using the benzylidene-protected Bis-MPA anhydride of EXAMPLE 2 and DMAP to afford C3-([G-1]Ph)$_3$. Molecular Formula: $C_{41}H_{48}O_{12}$. MALDI-TOF MS: Theoretical Exact MW: [M+Ag]$^+$ m/z=839.220. Observed MW: [M+Ag]$^+$ m/z=83920

Synthesis of C3-([G-1]OH$_2$)$_3$, dendrimer 2 of FIG. 1: The benzylidene protected dendrimer 1 was deprotected using 5% Pd(OH)$_2$/C and hydrogen gas following the General Deprotection Procedure of EXAMPLE 4, to afford C3-([G-1]OH$_2$)$_3$. Molecular Formula: $C_{20}H_{36}O_{12}$. MALDI-TOF MS: Theoretical Exact MW: [M+Na]$^+$ m/z=491.210. Observed MW: [M+Na]$^+$ m/z=491.22

Synthesis of C3-([G-2]Ph$_2$)$_3$, dendrimer 3 of FIG. 1: The hydroxylated dendrimer 2, was esterified following the General Dendronization Procedure of EXAMPLE 3, using the benzylidene-protected Bis-MPA anhydride of EXAMPLE 2 and DMAP to afford C3-([G-2]Ph$_2$)$_3$, Molecular Formula: $C_{92}H_{108}O_{30}$. MALDI-TOF MS: Theoretical Exact MW: [M+Ag]$^+$ m/z=1799.598. Observed MW: [M+Ag]$^+$ m/z=1799.59

Synthesis of C3-([G-2]OH$_4$)$_3$, dendrimer 4 of FIG. 1: The benzylidene protected dendrimer 3 was deprotected using 5% Pd(OH)$_2$/C and hydrogen gas following the General Deprotection Procedure of EXAMPLE 4, to afford C3-([G-2]OH$_4$)$_3$. Molecular Formula: $C_{50}H_{84}O_{30}$. MALDI-TOF MS: Theoretical Exact MW: [M+Na]$^+$ m/z=1187.495. Observed MW: [M+Na]$^+$ m/z=1187.46

Synthesis of C3-([G-3]Ph$_4$)$_3$, dendrimer 5 of FIG. 1: The hydroxylated dendrimer 4, was esterified following the General Dendronization Procedure of EXAMPLE 3, using the benzylidene-protected Bis-MPA anhydride of EXAMPLE 2 and DMAP to afford C3-([G-3]Ph$_4$)$_3$, Molecular Formula: $C_{194}H_{228}O_{66}$. MALDI-TOF MS: Theoretical Exact MW: $[M+Ag]^+$ m/z=3720.354. Observed MW: $[M+Ag]^+$ m/z=3720.42

Synthesis of C3-([G-3]OH$_8$)$_3$, dendrimer 6 of FIG. 1: The benzylidene protected dendrimer 5 was deprotected using 5% Pd(OH)$_2$/C and hydrogen gas following the General Deprotection Procedure of EXAMPLE 4, to afford C3-([G-3]OH$_8$)$_3$. Molecular Formula: $C_{110}H_{180}O_{66}$, MALDI-TOF MS: Theoretical Exact MW: $[M+Na]^+$ m/z=2580.063. Observed MW: $[M+Na]^+$ m/z=2580.10

Synthesis of C3-([G-4]Ph$_8$)$_3$, dendrimer 7 of FIG. 1: The hydroxylated dendrimer 6, would be esterified following the General Dendronization Procedure of EXAMPLE 3, using the benzylidene-protected Bis-MPA anhydride of EXAMPLE 2 and DMAP to afford C3-([G-4]Ph$_8$)$_3$. Molecular Formula: $C_{398}H_{468}O_{138}$. MALDI-TOF MS: Theoretical Exact MW: $[M+Ag]^+$ m/z=7561.865. Observed MW: $[M+Ag]^+$ m/z=7559.9.

Synthesis of C3-([G-4]OH$_{16}$)$_3$, dendrimer 8 of FIG. 1: The benzylidene protected dendrimer 7 would be deprotected using 5% Pd(OH)$_2$/C and hydrogen gas following the General Deprotection Procedure of EXAMPLE 4, to afford C3-([G-4]OH$_{16}$)$_3$. Molecular Formula: $C_{230}H_{372}O_{138}$. MALDI-TOF MS: Theoretical Exact MW: $[M+Na]^+$ m/z=5365256. Observed MW: $[M+Na]^+$ m/z=5366.6.

Synthesis of C3-([G-5]Ph$_{16}$)$_3$, dendrimer 9 of FIG. 1: The hydroxylated dendrimer 8, would be esterified following General Dendronization Procedure of EXAMPLE 3, using the benzylideneprotected Bis-MPA anhydride of EXAMPLE 2 and DMAP to afford C3-([G-5]Ph$_{16}$)$_3$. Molecular Formula: $C_{806}H_{948}O_{282}$ MALDI-TOF MS: Theo. Avg. MW: $[M+Ag]^+$ m/z=15256.1. Observed MW: $[M+Ag]^+$ m/z=to be determined.

Synthesis of C3-([G-5]OH$_{32}$)$_3$, dendrimer 10 of FIG. 1: The benzylidene protected dendrimer 9 would be deprotected using 5% Pd(OH)$_2$/C and hydrogen gas following the General Deprotection Procedure of EXAMPLE 4, to afford C3-([G-5]OH$_{32}$)$_3$. Molecular Formula: $C_{470}H_{756}O_{282}$. MALDI-TOF MS: Theo. Avg. MW: $[M+Na]^+$ m/z=10942.0. Observed MW: $[M+Na]^+$ m/z=to be determined.

Example 6

Synthesis of Tetra-Functional "C-4" Calibrants

Figure 2:
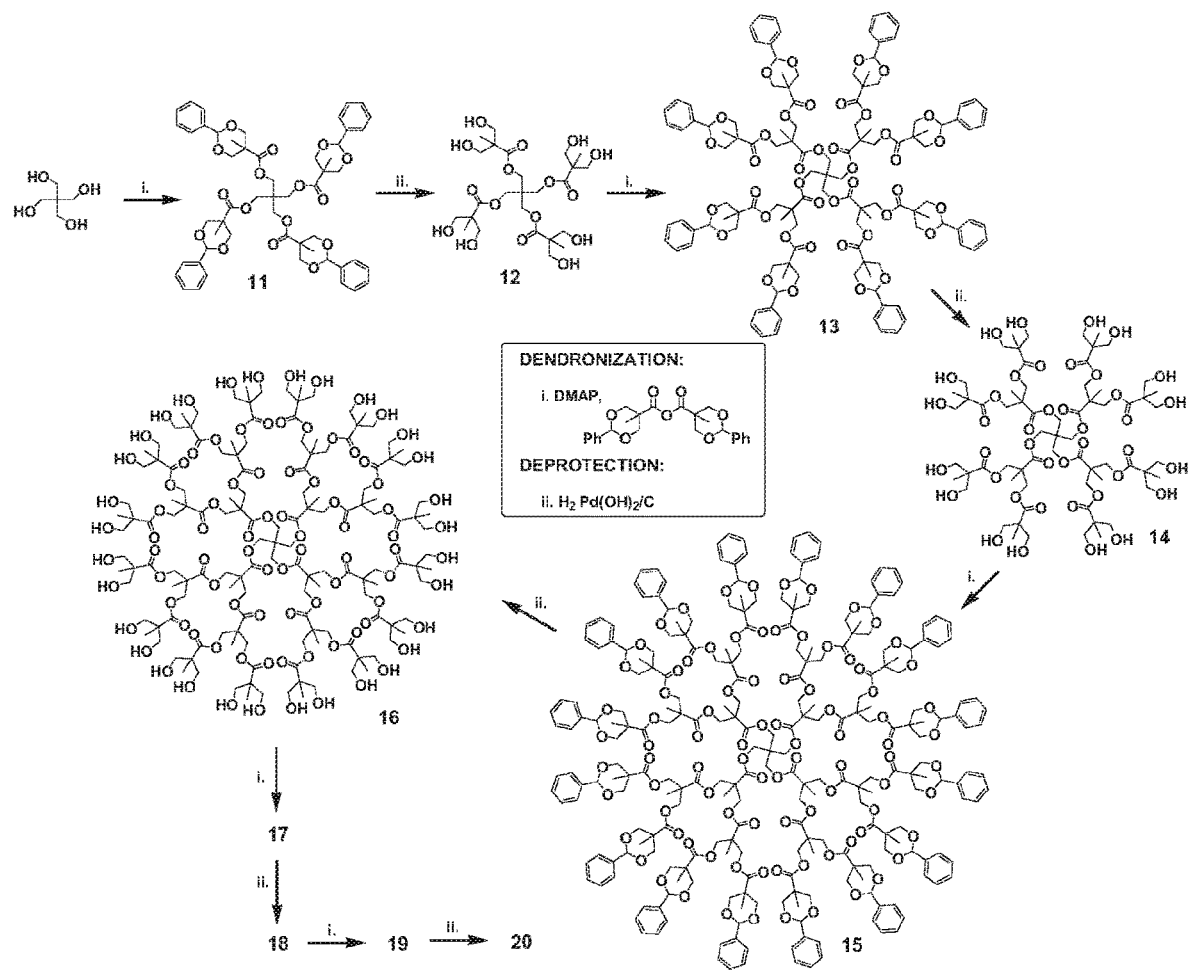
FIG. 2 is a schematic diagram showing the synthesis of tetra-functional "C-4" calibrants of the present disclosure.

The tetra-functional dendrimer species of this EXAMPLE 6 are shown in FIG. 2.

Synthesis of C4-([G-1]Ph)$_4$, dendrimer 11 of FIG. 2: Pentaerythritol (IUPAC name: 2,2-bis(hydroxymethyl)propane-1,3-diol), which is commercially available, was esterified following the General Dendronization Procedure of EXAMPLE 3, using the benzylidene-protected Bis-MPA anhydride of EXAMPLE 2 and DMAP to afford C4-([G-1]Ph)$_4$. Molecular Formula: $C_{53}H_{60}O_{16}$. MALDI-TOF MS: Theoretical Exact MW: $[M+Ag]^+$ m/z=1059.292. Observed MW: $[M+Ag]^+$ m/z=1059.28

Synthesis of C4-([G-1]OH$_2$)$_4$, dendrimer 12 of FIG. 2: The benzylidene protected dendrimer 11 was deprotected using 5% Pd(OH)$_2$/C and hydrogen gas following the General Deprotection Procedure of EXAMPLE 4, to afford C4-([G-1]OH$_2$)$_4$. Molecular Formula $C_{25}H_{44}O_{16}$. MALDI-TOF MS: Theoretical Exact MW: $[M+Na]^+$ m/z=623.252. Observed MW: $[M+Na]^+$ m/z=623.05

Synthesis of C4-([G-2]Ph$_2$)$_4$, dendrimer 13 of FIG. 2: The hydroxylated dendrimer 12, was esterified following the General Dendronization Procedure of EXAMPLE 3, using the benzylidene-protected Bis-MPA anhydride of EXAMPLE 2 and DMAP to afford C4-([G-2]Ph$_2$)$_4$. Molecular Formula: $C_{121}H_{140}O_{40}$. MALDI-TOF MS: Theoretical Exact MW: $[M+Ag]^-$ m/z=2339.797. Observed MW: $[M+Ag]^+$ m/z=2339.85

Synthesis of C4-([G-2]OH$_4$)$_4$, dendrimer 14 of FIG. 2: The benzylidene protected dendrimer 13 was deprotected using 5% Pd(OH)$_2$/C and hydrogen gas following the General Deprotection Procedure of EXAMPLE 4 to afford C4-([G-2]OH$_4$)$_4$. Molecular Formula: $C_{65}H_{108}O_{40}$. MALDI-TOF MS: Theoretical Exact MW: $[M+Na]^+$ m/z=1551.631. Observed MW: $[M+Na]^+$ m/z=1551.62

Synthesis of C4-([G-3]Ph$_4$)$_4$, dendrimer 15 of FIG. 2: The hydroxylated dendrimer 14, was esterified following the General Dendronization Procedure of EXAMPLE 3, using the benzylidene-protected Bis-MPA anhydride of EXAMPLE 2 and DMAP to afford C4-([G-3]Ph)$_4$. Molecular Formula: $C_{257}H_{300}O_{88}$. MALDI-TOF MS: Theoretical Exact MW: $[M+Ag]^+$ m/z=4900.805. Observed MW: $[M+Ag]^+$ m/z=4900.98

Synthesis of C4-([G-3]OH$_8$)$_4$, dendrimer 16 of FIG. 2: The benzylidene protected dendrimer 15 was deprotected using 5% Pd(OH)$_2$/C and hydrogen gas following the General Deprotection Procedure of EXAMPLE 4, to afford C4-([G-3]OH$_8$)$_4$. Molecular Formula: $C_{145}H_{236}O_{88}$. MALDI-TOF MS: Theoretical Exact MW: $[M+Na]^+$ m/z=3408389 Observed MW: $[M+Na]^+$ m/z=3408.41

Synthesis of C4-([G-4]Ph$_8$)$_4$, dendrimer 17 of FIG. 2: The hydroxylated dendrimer 16, would be esterified following the General Dendronization Procedure of EXAMPLE 3, using the benzylideneprotected Bis-MPA anhydride of EXAMPLE 2 and DMAP to afford C3-([G-4]Ph$_8$)$_4$. Molecular Formula: $C_{529}H_{620}O_{184}$. MALDI-TOF MS: Theo. Avg. MW: $[M+Ag]^+$ m/z=10030.5 Observed MW: $[M+Ag]^+$ m/z=10018.1.

Synthesis of C4-([G-4]OH$_{16}$)$_4$, dendrimer 18 of FIG. 2: The benzylidene protected dendrimer 17 would be deprotected using 5% Pd(OH)$_2$/C and hydrogen gas following the General Deprotection Procedure of EXAMPLE 4, to afford C4-([G-4]OH$_{16}$)$_4$. Molecular Formula $C_{305}H_{492}O_{184}$. MALDI-TOF MS: Theo. Avg. MW: $[M+Na]^+$ m/z=7126.1. Observed MW: $[M+Na]^+$ m/z=7123.5.

Synthesis of C4-([G-5]Ph$_{16}$)$_4$, dendrimer 19 of FIG. 2: The hydroxylated dendrimer 18, would be esterified following the General Dendronization Procedure of EXAMPLE 3, using the benzylideneprotected Bis-MPA anhydride of EXAMPLE 2 and DMAP to afford C4-([G-5]Ph$_{16}$)$_4$. Molecular Formula: $C_{1073}H_{1260}O_{376}$. MALDI-TOF MS: Theo. Avg. MW: $[M+Ag]^+$ m/z=20281.4. Observed MW: $[M+Ag]^+$ m/z=to be determined.

Synthesis of C4-([G-5]OH$_{32}$)$_4$, dendrimer 20 of FIG. 2: The benzylidene protected dendrimer 19 would be deprotected using 5% Pd(OH)/C and hydrogen gas following the General Deprotection Procedure of EXAMPLE 4, to afford C4-([G-5]OH$_{32}$)$_4$. Molecular Formula $C_{625}H_{1004}O_{376}$. MALDI-TOF MS: Theo. Avg. MW: $[M+Na]^+$ m/z=14557.6. Observed MW: $[M+Na]^+$ m/z=to be determined.

Example 7

Synthesis of Penta-Functional "C-5" Calibrants

Figure 3:
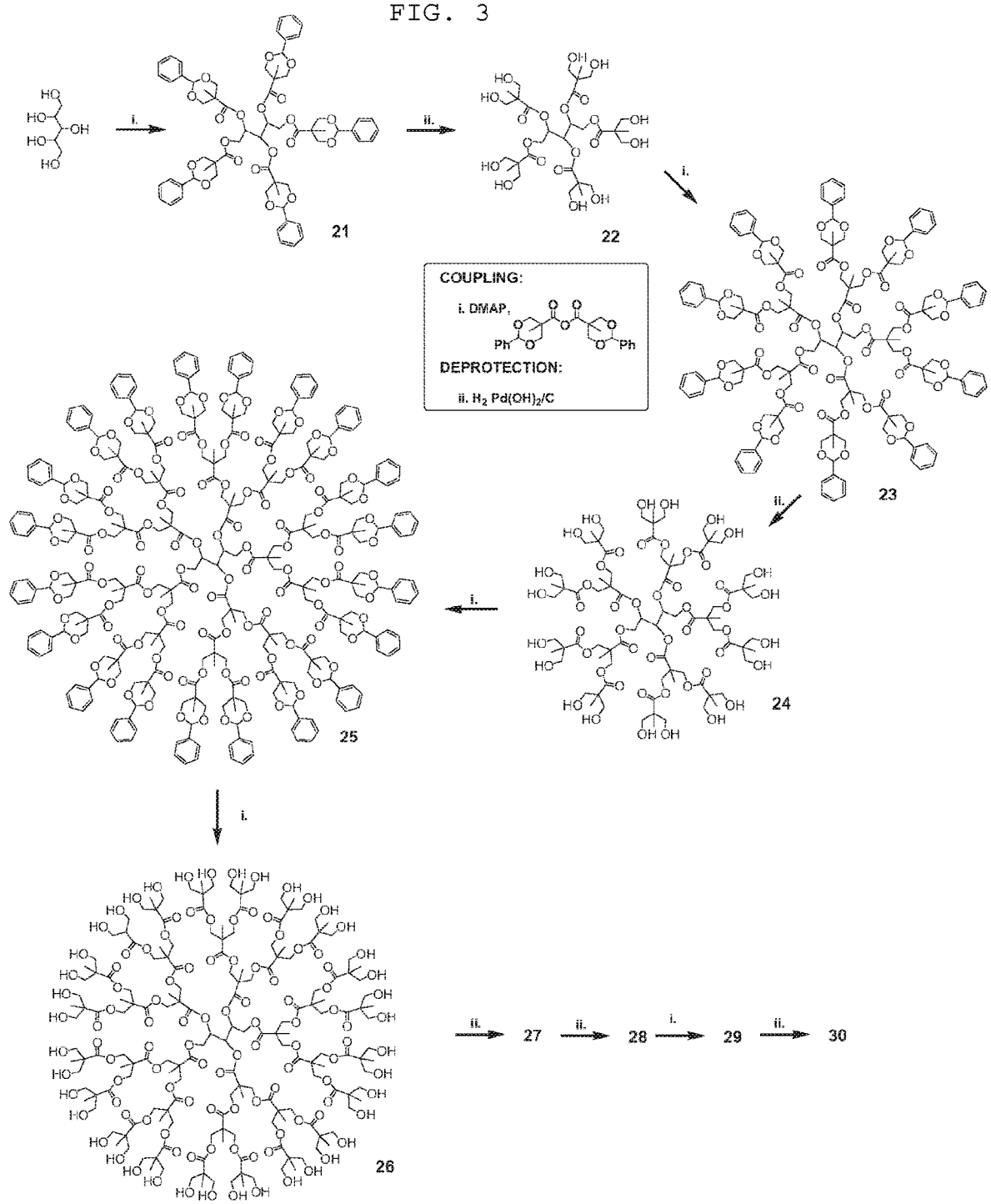
FIG. 3 is a schematic diagram showing the synthesis of penta-functional "C-5" calibrants of the present disclosure.

The penta-functional dendrimer species of this EXAMPLE 7 are shown in FIG. 3.

Synthesis of C5-([G-1]Ph)$_5$, dendrimer 21 of FIG. 3: Xylitol (IUPAC name: pentane-1,2,3,4,5-pentol), which is commercially available, was esterified following the General Dendronization Procedure of EXAMPLE 3, using the benzylidene-protected Bis-MPA anhydride of EXAMPLE 2 and DMAP to afford C5-([G-1]Ph)$_5$. Molecular Formula:

$C_{65}H_{72}O_{20}$. MALDI-TOF MS: Theoretical Exact MW: $[M+Ag]^+$ m/z=1279.366. Observed MW: $[M+Ag]^+$ m/z=1279.39

Synthesis of C5-([G-1]$OH_2$)$_5$, dendrimer 22 of FIG. 3: The benzylidene protected dendrimer 21 was deprotected using 5% Pd(OH)$_2$/C and hydrogen gas following the General Deprotection Procedure of EXAMPLE 4, to afford C5-([G-1]$OH_2$)$_5$. Molecular Formula: $C_{30}H_{52}O_{20}$. MALDI-TOF MS: Theoretical Exact MW: $[M+Na]^+$ m/z=755.295. Observed MW: $[M+Na]^+$ m/z=755.17

Synthesis of C5-([G-2]$Ph_2$)$_5$, dendrimer 23 of FIG. 3: The hydroxylated dendrimer 22, was esterified following the General Dendronization Procedure of EXAMPLE 3, using the benzylidene-protected Bis-MPA anhydride of EXAMPLE 2 and DMAP to afford C5-([G-2]$Ph_2$)$_5$. Molecular Formula: $C_{150}H_{172}O_{50}$. MALDI-TOF MS: Theoretical Exact MW: $[M+Ag]^-$ m/z=2879.997. Observed MW: $[M+Ag]^+$ m/z=2880.01

Synthesis of C5-([G-2]$OH_4$)$_5$, dendrimer 24 of FIG. 3: The benzylidene protected dendrimer 23 was deprotected using 5% Pd(OH)$_2$/C and hydrogen gas following the General Deprotection Procedure of EXAMPLE 4, to afford C5-([G-2]$OH_4$)$_5$. Molecular Formula: $C_{80}H_{132}O_{50}$. Molecular Formula: $C_{150}H_{172}O_{50}$. MALDI-TOF MS: Theoretical Exact MW: $[M+Na]^+$ m/z=1915.768. Observed MW: $[M+Na]^+$ m/z=1915.78

Synthesis of C5-([G-3]$Ph_4$)$_5$, dendrimer 25 of FIG. 3: The hydroxylated dendrimer 24, was esterified following the General Dendronization Procedure of EXAMPLE 3, using the benzylidene-protected Bis-MPA anhydride of EXAMPLE 2 and DMAP to afford C5-([G-3]$Ph_4$)$_5$. Molecular Formula: $C_{320}H_{327}O_{110}$. MALDI-TOF MS: Theoretical Exact MW: $[M+Ag]^-$ m/z=6081.257. Observed MW: $[M+Ag]^+$ m/z=6081.51

Synthesis of C5-([G-3]$OH_8$)$_5$, dendrimer 26 of FIG. 3: The benzylidene protected dendrimer 25 was deprotected using 5% Pd(OH)$_2$/C and hydrogen gas following the General Deprotection Procedure of EXAMPLE 4, to afford C5-([G-3]$OH_8$)$_5$. Molecular Formula: $C_{180}H_{292}O_{110}$. MALDI-TOF MS: Theoretical Exact MW: $[M+Na]^+$ m/z=4236.715. Observed MW: $[M+Na]^+$ m/z=4236.80

Synthesis of C5-([G-4]$Ph_8$)$_5$, dendrimer 27 of FIG. 3: The hydroxylated dendrimer 26, would be esterified following the General Dendronization Procedure of EXAMPLE 3, using the benzylideneprotected Bis-MPA anhydride of EXAMPLE 2 and DMAP to afford C5-([G-4]$Ph_8$)$_5$. Molecular Formula: $C_{660}H_{772}O_{230}$. MALDI-TOF MS: Theo. Avg. MW: $[M+Ag]^+$ m/z=12493.1. Observed MW: $[M+Ag]^+$ m/z=12476.0.

Synthesis of C5-([G-4]$OH_{16}$)$_5$, dendrimer 28 of FIG. 3: The benzylidene protected dendrimer 27 would be deprotected using 5% Pd(OH)$_2$/C and hydrogen gas following the General Deprotection Procedure of EXAMPLE 4, to afford C5-([G-4]$OH_{16}$)$_5$. Molecular Formula: $C_{380}H_{612}O_{230}$. MALDI-TOF MS: Theo. Avg. MW: $[M+Na]^+$ m/z=8883.9. Observed MW: $[M+Na]^+$ m/z=8880.1.

Synthesis of C5-([G-5]$Ph_{16}$)$_5$, dendrimer 29 of FIG. 3: The hydroxylated dendrimer 28, would be esterified following the General Dendronization Procedure of EXAMPLE 3, using the benzylideneprotected Bis-MPA anhydride of EXAMPLE 2 and DMAP to afford C5-([G-5]$Ph_{16}$)$_5$. Molecular Formula: $C_{1340}H_{1572}O_{470}$, MALDI-TOF MS: Theo. Avg. MW: $[M+Ag]^+$ m/z=25306.7. Observed MW: $[M+Ag]^+$ m/z=to be determined.

Synthesis of C5-([G-5]$OH_{32}$)$_5$, dendrimer 30 of FIG. 3: The benzylidene protected dendrimer 29 would be deprotected using 5% Pd(OH)$_2$/C and hydrogen gas following the General Deprotection Procedure of EXAMPLE 4, to afford C5-([G-5]$OH_{32}$)$_5$. Molecular Formula: $C_{780}H_{1252}O_{470}$. MALDI-TOF MS: Theo. Avg. MW: $[M+Na]^+$ m/z=18173.2. Observed MW: $[M+Na]^+$ m/z: =to be determined.

Example 8

Figure 4:
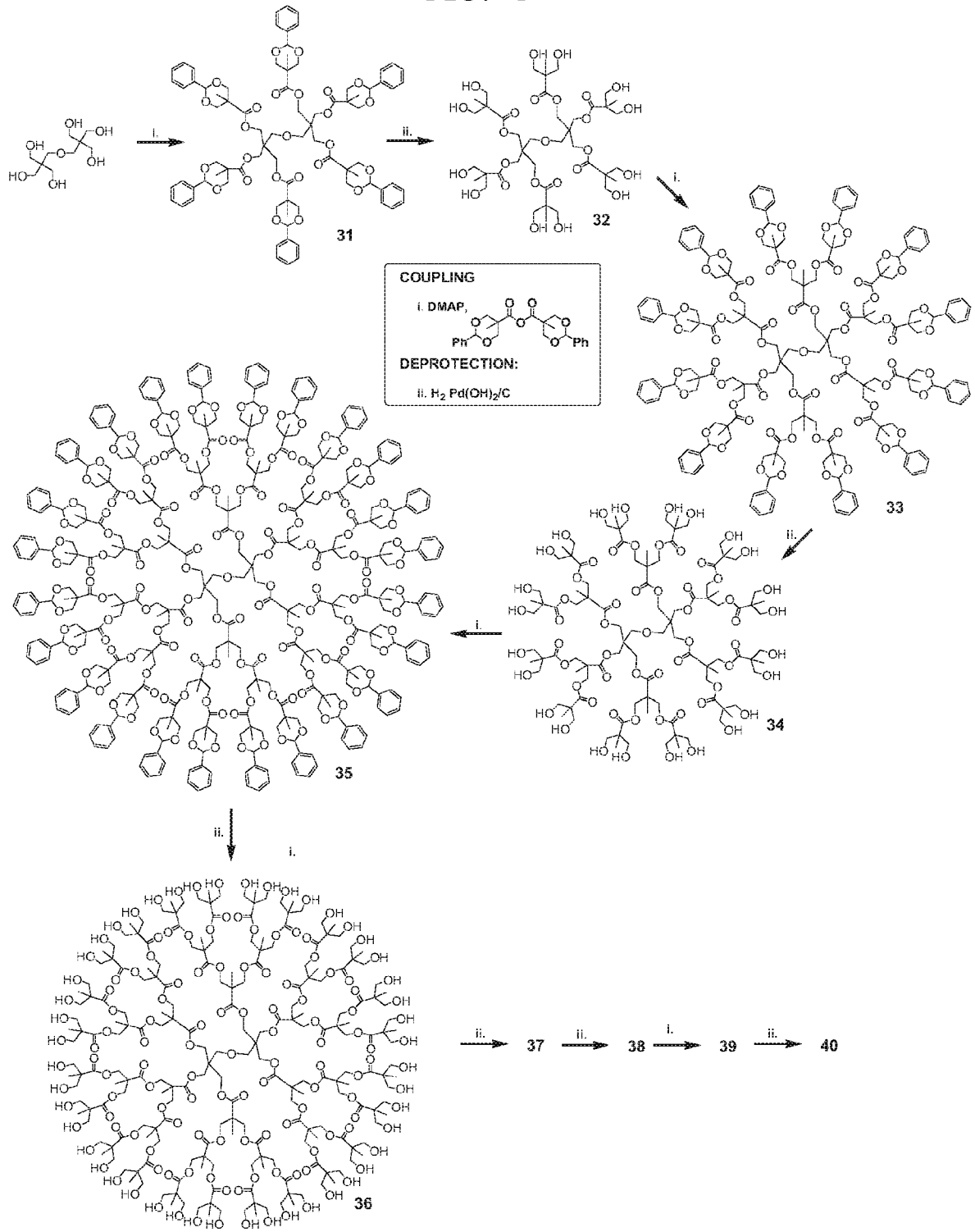
FIG. 4 is a schematic diagram showing the synthesis of hexa-functional "C-6" calibrants of the present disclosure.

Synthesis of Hexa-Functional "C-6" Calibrants
The hexa-functional dendrimer species of this EXAMPLE 8 are shown in FIG. 4.

Synthesis of C6-([G-1]Ph)$_6$, dendrimer 31 of FIG. 4: Dipentaerythritol (IUPAC name: 2-[[3-hydroxy2,2-bis(hydroxymethyl)propoxy]methyl]-2-(hydroxymethyl)propane-1,3-diol), which is commercially available, was esterified following the General Dendronization Procedure of EXAMPLE 3, using the benzylidene-protected Bis-MPA anhydride of EXAMPLE 2 and DMAP to afford C6-([G-1]Ph)$_6$. Molecular Formula: $C_{82}H_{94}O_{25}$. MALDI-TOF MS: Theoretical Exact MW: $[M+Ag]^+$ m/z=1585.514. Observed MW: $[M+Ag]^+$ m/z=1585.53

Synthesis of C6-([G-1]$OH_2$)$_6$, dendrimer 32 of FIG. 4: The benzylidene protected dendrimer 31 was deprotected using 5% Pd(OH)$_2$/C and hydrogen gas following the General Deprotection Procedure of EXAMPLE 4, to afford C6-([G-1]$OH_2$)$_6$. Molecular Formula: $C_{40}H_{70}O_{25}$. MALDI-TOF MS: Theoretical Exact MW: $[M+Na]^+$ m/z=973.410. Observed MW: $[M+Na]^+$ m/z=973.34

Synthesis of C6-([G-2]$Ph_2$)$_6$, dendrimer 33 of FIG. 4: The hydroxylated dendrimer 32, was esterified following the General Dendronization Procedure of EXAMPLE 3, using the benzylidene-protected Bis-MPA anhydride of EXAMPLE 2 and DMAP to afford C6-([G-2]$Ph_2$)$_6$. Molecular Formula: $C_{181}H_{214}O_{61}$. MALDI-TOF MS: Theoretical Exact MW: $[M+Ag]^-$ m/z=3506.269. Observed MW: $[M+Ag]^+$ m/z=3506.25

Synthesis of C6-([G-2]$OH_4$)$_6$, dendrimer 34 of FIG. 4: The benzylidene protected dendrimer 33 was deprotected using 5% Pd(OH)$_2$/C and hydrogen gas following the General Deprotection Procedure of EXAMPLE 4, to afford C6-([G-2]$OH_4$)$_6$. Molecular Formula: $C_{100}H_{166}O61$. MALDI-TOF MS: Theoretical Exact MW: $[M+Na]^+$ m/z=2365.979. Observed MW: $[M+Na]^+$ m/z=2365.98

Synthesis of C6-([G-3]$Ph_4$)$_6$, dendrimer 35 of FIG. 4: The hydroxylated dendrimer 34, was esterified following the General Dendronization Procedure of EXAMPLE 3, using the benzylidene-protected Bis-MPA anhydride of EXAMPLE 2 and DMAP to afford C6-([G-3]$Ph_4$)$_6$. Molecular Formula $C_{388}H_{454}O_{133}$. MALDI-TOF MS: Theoretical Exact MW: $[M+Ag]^+$ m/z=7347.781. Observed MW: $[M+Ag]^+$ m/z=7347.0

Synthesis of C6-([G-3]$OH_8$)$_6$, dendrimer 36 of FIG. 4: The benzylidene protected dendrimer 35 was deprotected using 5% Pd(OH)$_2$/C and hydrogen gas following the General Deprotection Procedure of EXAMPLE 4, to afford C6-([G-3]$OH_8$)$_6$. Molecular Formula $C_{220}H_{358}O_{133}$. MALDI-TOF MS: Theoretical Exact MW: $[M+Na]^+$ m/z=5151.115. Observed MW: $[M+Na]^+$ m/z=5151.28

Synthesis of C6-([G-4]$Ph_8$)$_6$, dendrimer 37 of FIG. 4: The hydroxylated dendrimer 36, would be esterified following the General Dendronization Procedure of EXAMPLE 3, using the benzylideneprotected Bis-MPA anhydride of EXAMPLE 2 and DMAP to afford C6-([G-4]$Ph_8$)$_6$. Molecular Formula: $C_{796}H_{934}O_{277}$. MALDI-TOF MS: Theo. Avg. MW: $[M+Ag]^+$ m/z=14969.7. Observed MW: $[M+Ag]^+$ m/z=15020.1.

Synthesis of C6-([G-4]$OH_{16}$)$_6$, dendrimer 38 of FIG. 4: The benzylidene protected dendrimer 37 would be deprotected using 5% Pd(OH)$_2$/C and hydrogen gas following the General Deprotection Procedure of EXAMPLE 4, to afford C6-([G-4]OH$_{16}$)$_6$. Molecular Formula: C$_{460}$H$_{742}$O$_{277}$. MALDI-TOF MS: Theo. Avg. MW: [M+Na]$^+$ m/z=10655.6. Observed MW: [M+Na]$^+$ m/z=10722.6.

Synthesis of C6-([G-5]Ph$_{16}$)$_6$, dendrimer 39 of FIG. 4: The hydroxylated dendrimer 38, would be esterified following the General Dendronization Procedure of EXAMPLE 3, using the benzylideneprotected Bis-MPA anhydride of EXAMPLE 2 and DMAP to afford C6-([G-5]Ph$_{16}$)$_6$. Molecular Formula: C$_{1612}$H$_{1894}$O$_{565}$. MALDI-TOF MS: Theo. Avg. MW: [M+Ag]$^+$ m/z=30346.1. Observed MW: [M+Ag]$^+$ m/z=to be determined.

Synthesis of C6-([G-5]OH$_{32}$)$_6$, dendrimer 40 of FIG. 4: The benzylidene protected dendrimer 39 would be deprotected using 5% Pd(OH)$_2$/C and hydrogen gas following the General Deprotection Procedure of EXAMPLE 4, to afford C6-([G-5]OH$_{32}$)$_6$. Molecular Formula: C$_{940}$H$_{1510}$O$_{565}$. MALDI-TOF MS: Theo. Avg. MW: [M+Na]$^+$ m/z=21802.8. Observed MW: [M+Na]$^+$ m/z=to be determined.

Example 9

Parallel Synthesis of Dendrimers 1, 11, 21, and 31

In the prior art, a broad range calibrant is made by mixing appropriate quantities of individual peptides, which have been prepared and purified separately, to yield a calibrant cocktail. The synthetic methodology described herein and shown schematically in FIG. 5, however, provides a unique way to prepare calibrant sets by starting with a mixture of well-defined commercially available starting materials, and dendronizing them in parallel.

By serial repetitions of steps "i" and "ii" as detailed in EXAMPLES 3 and 4 (and as shown, for example, in FIG. 1), dendrimers can be prepared with (approximately) exponentially increasing molecular weights. For example, by starting with just the C-3 hydroxyl-terminated core, serial repetition of steps "i" and "ii" can produce monodisperse dendrimer calibrants (e.g., dendrimers 1, 3, 5, 7, 9, etc. of FIG. 1) that have approximate molecular weights of 730, 1690, 3610, 7450, 15100, and 30500. By starting with a different core, bearing a different number of alcohol functionalities, (e.g., the C-4, C-5, or C-6 hydroxyl-terminated core), a wide range of calibrants with a broad distribution can be efficiently prepared.

Figure 5:
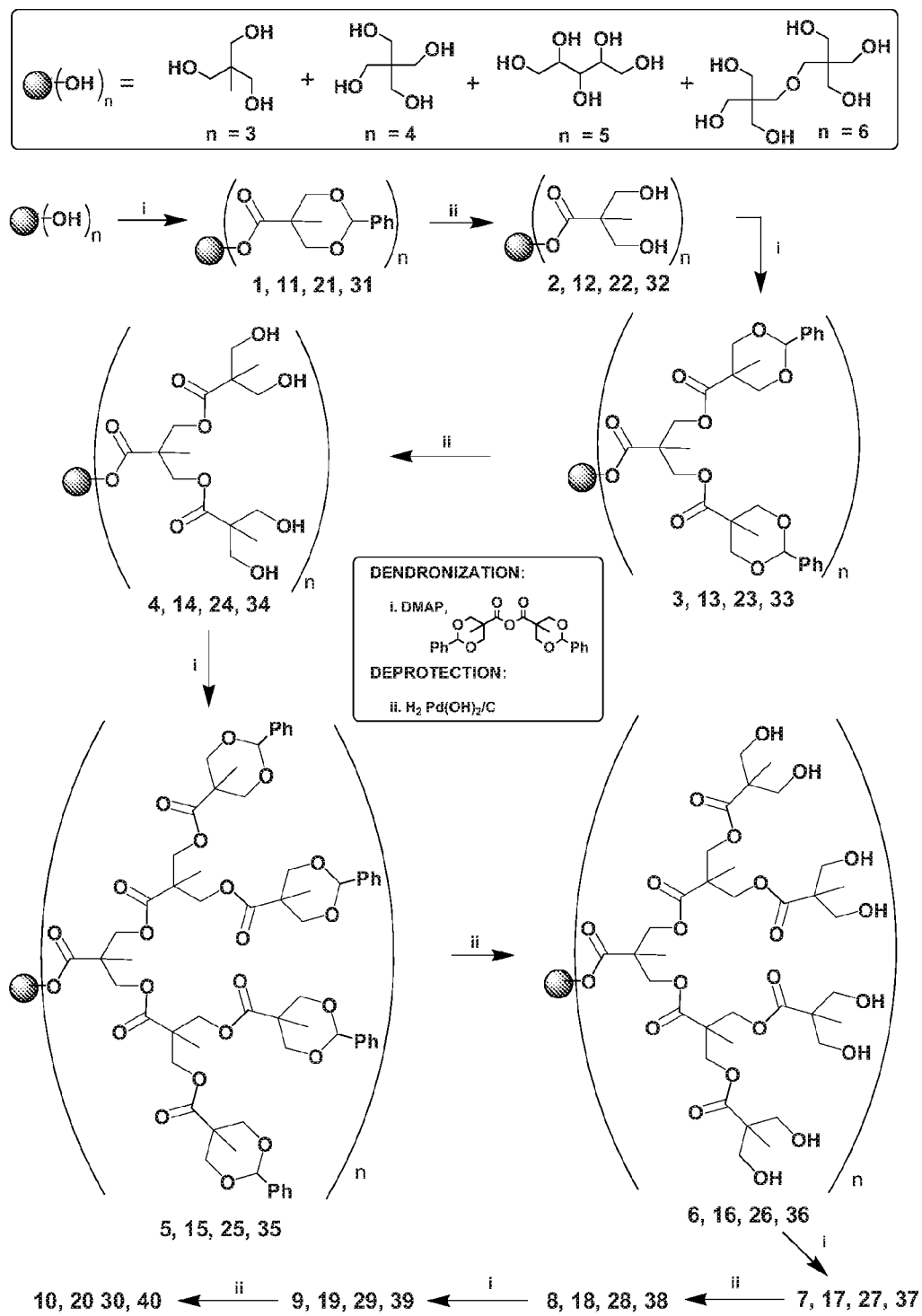
FIG. 5 is a schematic diagram showing the parallel synthesis of tri-, tetra-, penta- and hexa-functional calibrants of the present disclosure.

A particularly efficient way to make a calibranr mixture is to carry out the dendronization process using a mixture of cores in a single batch (e.g., equimolar mixtures of the C-3, C-4, C-5, and/or the C-6 cores). For example, and as shown in FIG. 5, after a single dendronization step, the mixture of four cores will yield a set of "first generation" dendrimers 1, 11, 21, and 31 having molecular weights (with silver counterion) of 839, 1059, 1279, and 1585 (as demonstrated in FIG. 6). After an additional repetition of steps "ii" and "i," also shown in FIG. 5, the set of "second generation" calibrants (3, 13, 23, 33) have molecular weights of 1800, 2340, 2880, and 3506 (as demonstrated in FIG. 7). In this way, serial repetitions of steps "i" and "ii" enable rapid access to a series of 4-point sets (se, e.g., FIGS. 6-12).

Because the most desirable calibrant would be a mixture of numerous, well-defined monodisperse compounds (e.g., as shown in the reaction scheme of FIG. 5 and the spectra of FIGS. 6-12), this described synthetic technique has the additional advantage that the different calibrants can be prepared together in one batch (by dendronizing a selected mixture of cores), rather than preparing each species separately and mixing them after the isolating of each product. Because previous attempts to prepare dendrimers sought a well-defined singular product, this parallel approach is both unprecedented and valuable in reducing the cost and effort of preparing sets of calibrants.

Figure 6:
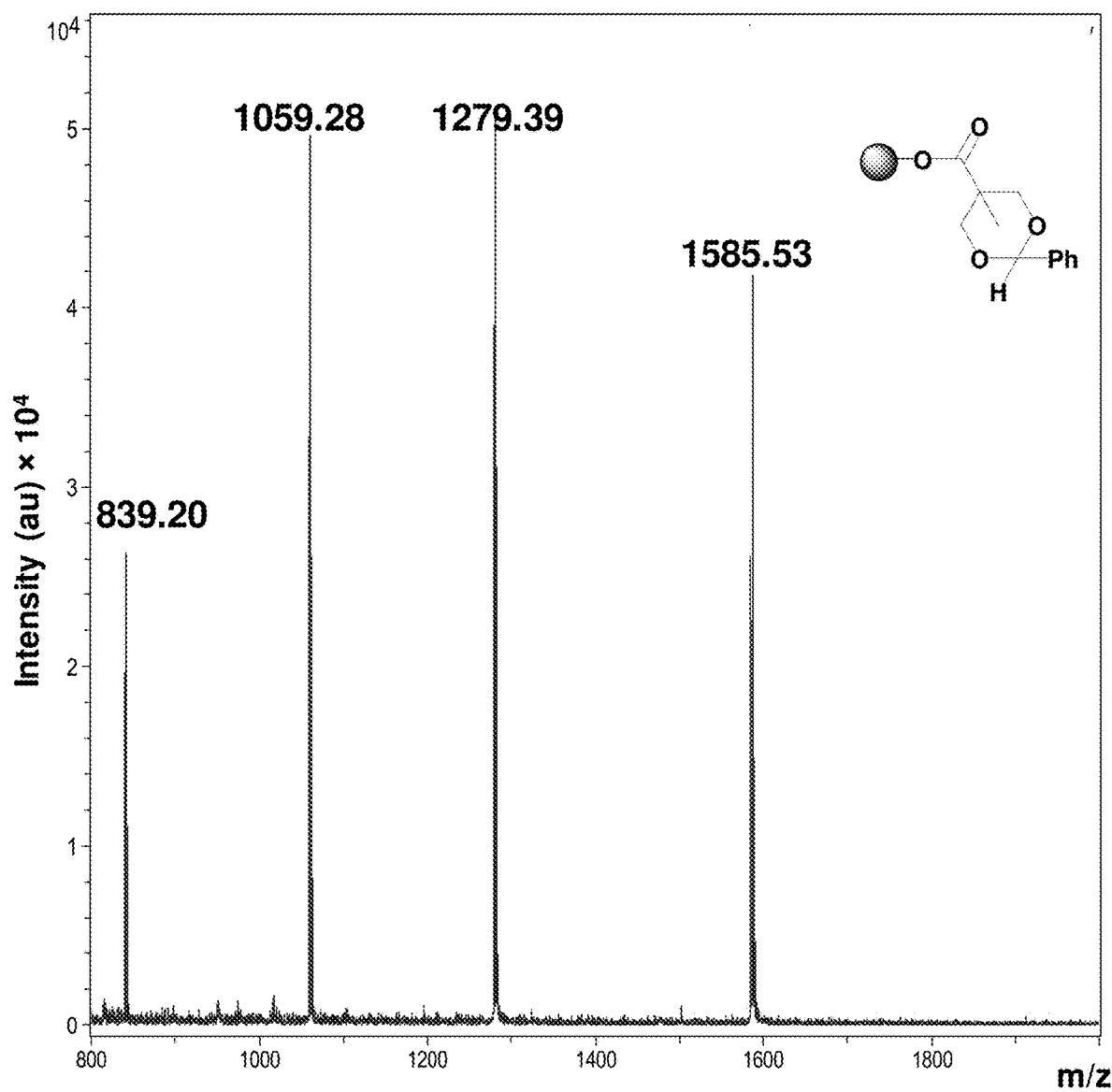
FIG. 6 shows the results of MALDI-TOF analysis of an equimolar mixture of dendrimers 1, 11, 21, and 31 of the present disclosure.

Synthesis of CX-([G-1]Ph)$_2$, an equimolar mixture of dendrimers 1, 11, 21, and 31 (see, e.g., reaction scheme of FIG. 5): An equimolar mixture of (trishydroxymethyl)ethane (C3-OH$_3$), pentaerythritol (C4-OH), xylitol (C5-OH$_5$), and dipentaerythritol (C6-OH$_6$) was esterified following the General Dendronization Procedure of EXAMPLE 3, using the benzylidene-protected Bis-MPA anhydride of EXAMPLE 2 and DMAP to afford the CX-([G-1]Ph), mixture of dendrimers 1, 11, 21, and 31. As shown in FIG. 6, MALDI-TOF MS: Theoretical Exact MW: [M+Ag]$^+$ m/z=839220; 1,059.293; 1,279.367; 1,585.514. Observed MW: [M+Ag]$^+$ m/z=839.20; 1,059.28; 1,279.39; 1585.53. As can be appreciated from FIG. 6, the mixture of dendrimers 1, 11, 21, and 31 provides an effective four-point calibration that covers the 800-1,600 mass range.

Example 10

Parallel Synthesis of Dendrimers 2, 12, 22, and 32

Synthesis of CX-([G-1]OH$_2$)$_2$, an equimolar mixture of dendrimers 2, 12, 22, and 32 (not shown) (see, e.g., reaction scheme of FIG. 5): The mixture of benzylidene protected dendrimers 1, 11, 21, and 31 from EXAMPLE 9 was deprotected using 5% Pd(OH)$_2$/C and hydrogen gas following the General Deprotection Procedure of EXAMPLE 4, to afford the CX-([G-1]OH$_2$)$_z$ mixture of dendrimers 2, 12, 22, and 32. MALDI-TOF MS: Theoretical Exact MW: [M+Na]$^+$ m/z=491210; 623253; 755.295; 973.410. Observed MW: [M+Na]$^+$ m/z=49122; 623.05; 755.17; and 973.34.

Example 11

Parallel Synthesis of Dendrimers 3, 13, 23, and 33

Figure 7:
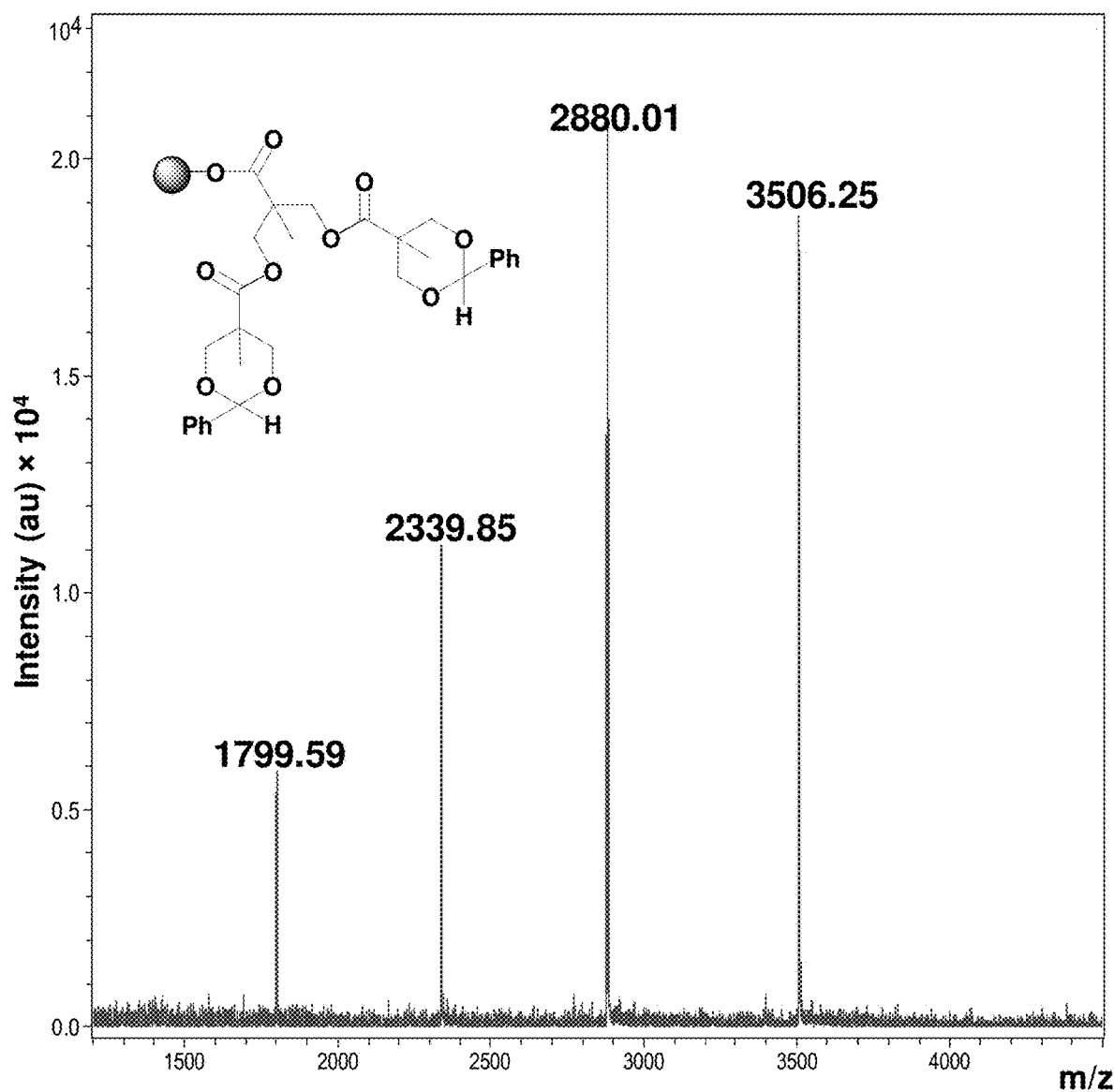
FIG. 7 shows the results of MALDI-TOF analysis of an equimolar mixture of dendrimers 3, 13, 23, and 33 of the present disclosure.

Synthesis of CX-([G-2]Ph$_2$)$_z$, an equimolar mixture of dendrimers 3, 13, 23, and 33 (se, e.g., reaction scheme of FIG. 5): The mixture of hydroxyl functionalized dendrimers 2, 12, 22, and 32 from EXAMPLE 10 was esterified following the General Dendronization Procedure of EXAMPLE 3, using the benzylidene-protected Bis-MPA anhydride of EXAMPLE 2 and DMAP to afford the CX-([G2]Ph$_2$)$_2$, mixture of dendrimers 3, 13, 23, and 33. As shown in FIG. 7, MALDI-TOF MS: Theoretical Exact MW: [M+Ag]$^+$ m/z=1,799.598; 2,339.797; 2,879.997; 3,506.269. Observed MW: [M+Ag]$^+$ m/z=1,799.59; 2,339.85; 2,880.01; 3,506.25. As can be appreciated from FIG. 7, the mixture of dendrimers 3, 13, 23, and 33 provides an effective four point calibration that covers the 1,800-3,600 mass range.

Example 12

Parallel Synthesis of Dendrimers 4, 14, 24, and 34

Figure 8:
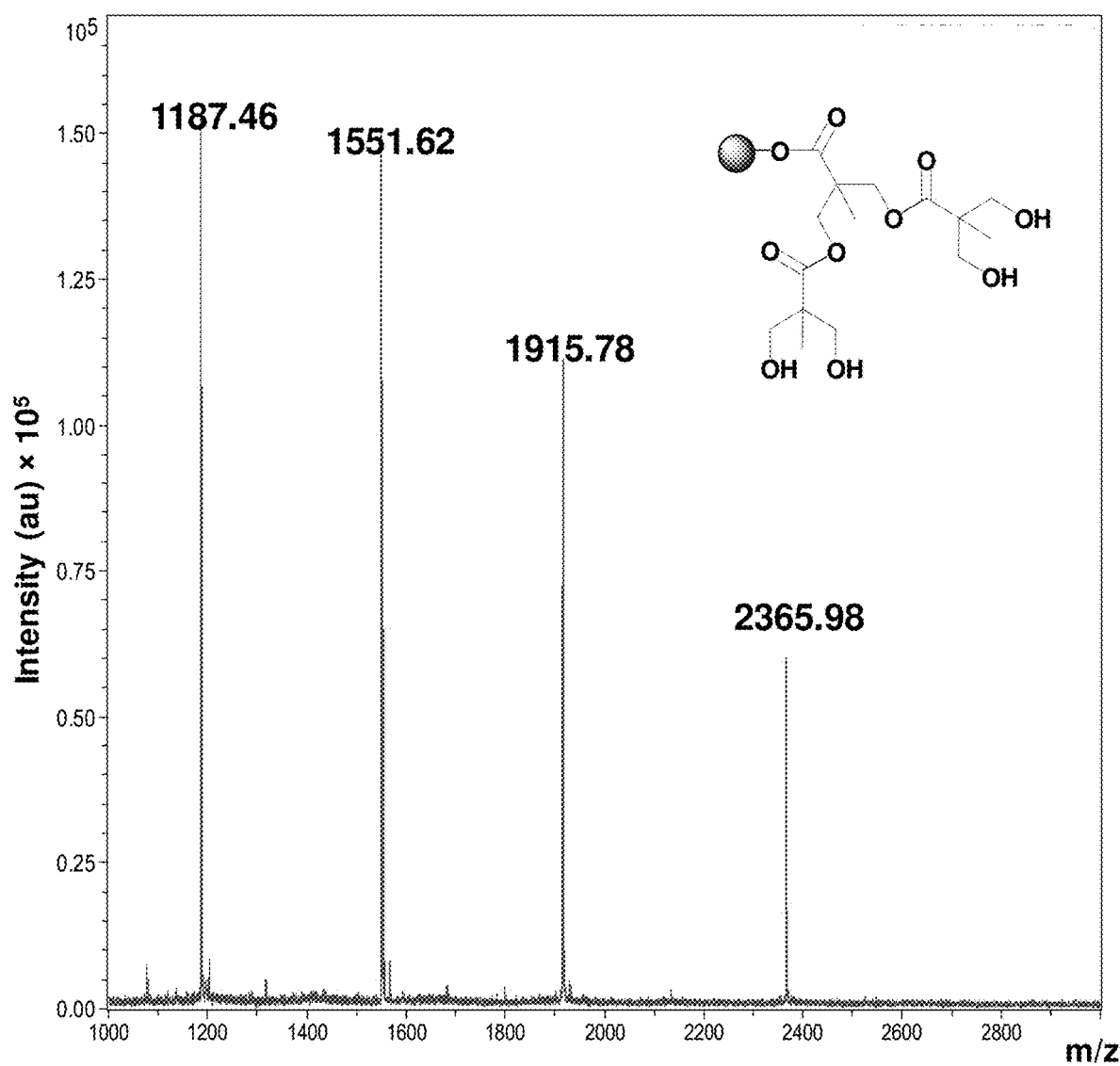
FIG. 8 shows the results of MALDI-TOF analysis of an equimolar mixture of dendrimers 4, 14, 24, and 34 of the present disclosure.

Synthesis of CX-([G-2]OH$_4$)$_z$, an equimolar mixture of dendrimers 4, 14, 24, and 34 (se, e.g., reaction scheme of FIG. 5): The mixture of benzylidene protected dendrimers 3, 13, 23, and 33 from EXAMPLE 11 was deprotected using 5% Pd(OH)$_1$/C and hydrogen gas following the General Deprotection Procedure of EXAMPLE 4, to afford the CX-([G-2]OH$_4$)$_z$ mixture of dendrimers 4, 14, 24, and 34. As shown in FIG. 8, MALDI-TOF MS: Theoretical Exact MW: [M+Na]$^+$ m/z=1,187.495; 1,551.631; 1,915.768; 2,365.979. Observed MW: [M+Na]$^+$ m/z=1,187.46; 1,551.62; 1,915.78; 2,365.98. As can be appreciated from FIG. 7, the mixture of dendrimers 4, 14, 24, and 34 provides an effective four point calibration that covers the 1,200-2,400 mass range.

Example 13

Parallel Synthesis of Dendrimers 5, 15, 25, and 35

Figure 9:
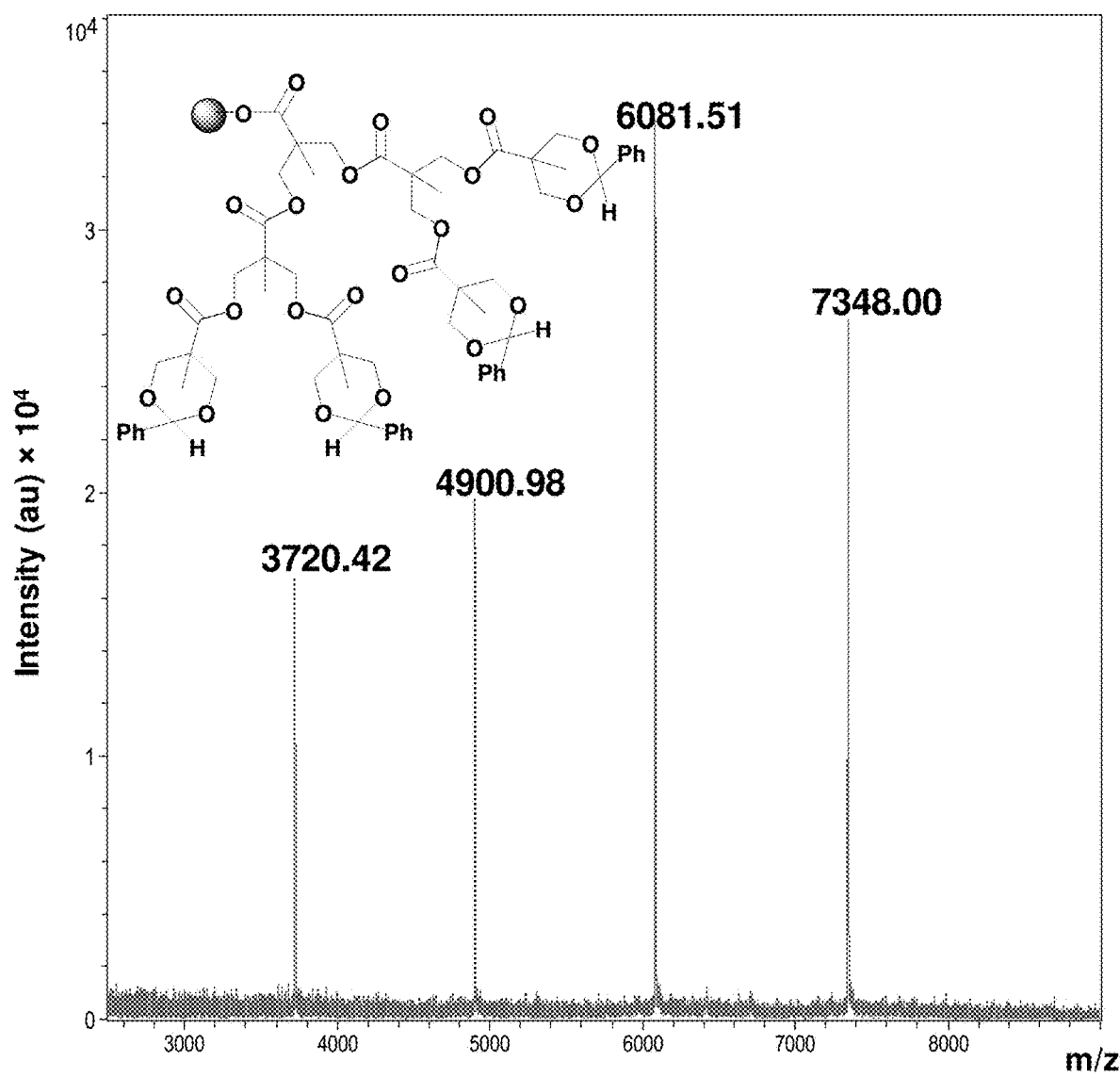
FIG. 9 shows the results of MALDI-TOF analysis of an equimolar mixture of dendrimers 5, 15, 25, and 35 of the present disclosure.

Synthesis of CX-([G-3]Ph$_4$)$_z$, an equimolar mixture of dendrimers 5, 15, 25, and 35 (see, e.g., reaction scheme of FIG. 5): The mixture of hydroxyl functionalized dendrimers 4, 14, 24, and 34 from EXAMPLE 12 was esterified following the General Dendronization Procedure of EXAMPLE 3, using the benzylidene-protected Bis-MPA anhydride from EXAMPLE 2 and DMAP to afford the CX-([G3]Ph$_4$)$_z$ mixture of dendrimers 5, 15, 25, and 35. As shown in FIG. 9, MALDI-TOF MS: Theoretical Exact MW: [M+Ag]$^+$ m/z=3,720.354; 4,900.805; 6,081.257; 7,347.781. Observed MW: [M+Ag]$^+$ m/z=3,720.42; 4,900.98; 6,081.51; and 7,348.00. As can be appreciated from FIG. 9, the mixture of dendrimers 5, 15, 25, and 35 provides an effective four point calibration that covers the 3,600-7,200 mass range.

Example 14

Parallel Synthesis of Dendrimers 6, 16, 26, and 36

Figure 10:
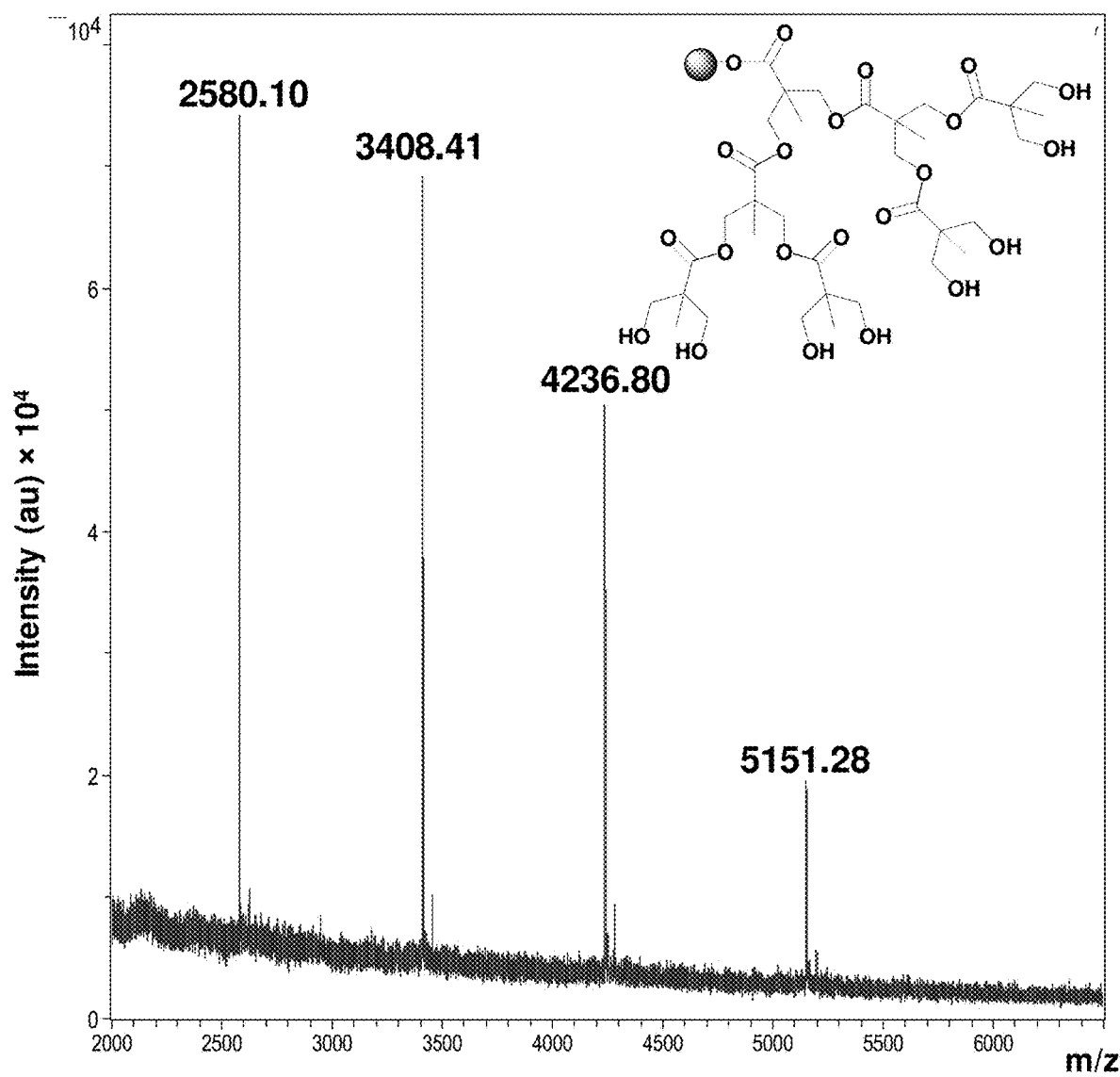
FIG. 10 shows the results of MALDI-TOF analysis of an equimolar mixture of dendrimers 6, 16, 26, and 36 of the present disclosure.
Figure 11:
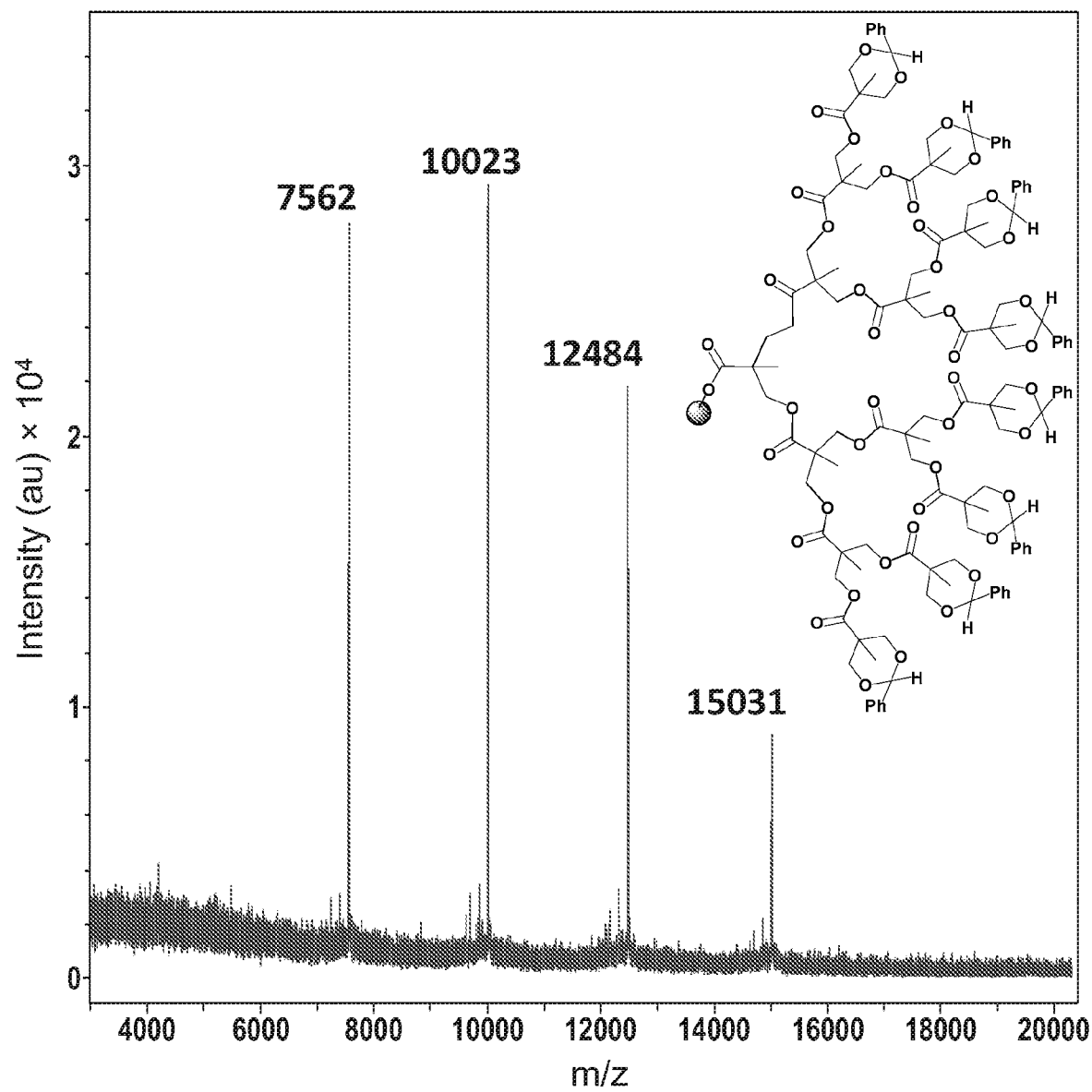
FIG. 11 shows the results of MALDI-TOF analysis of an equimolar mixture of dendrimers 7, 17, 27, and 37 of the present disclosure.
Figure 12:
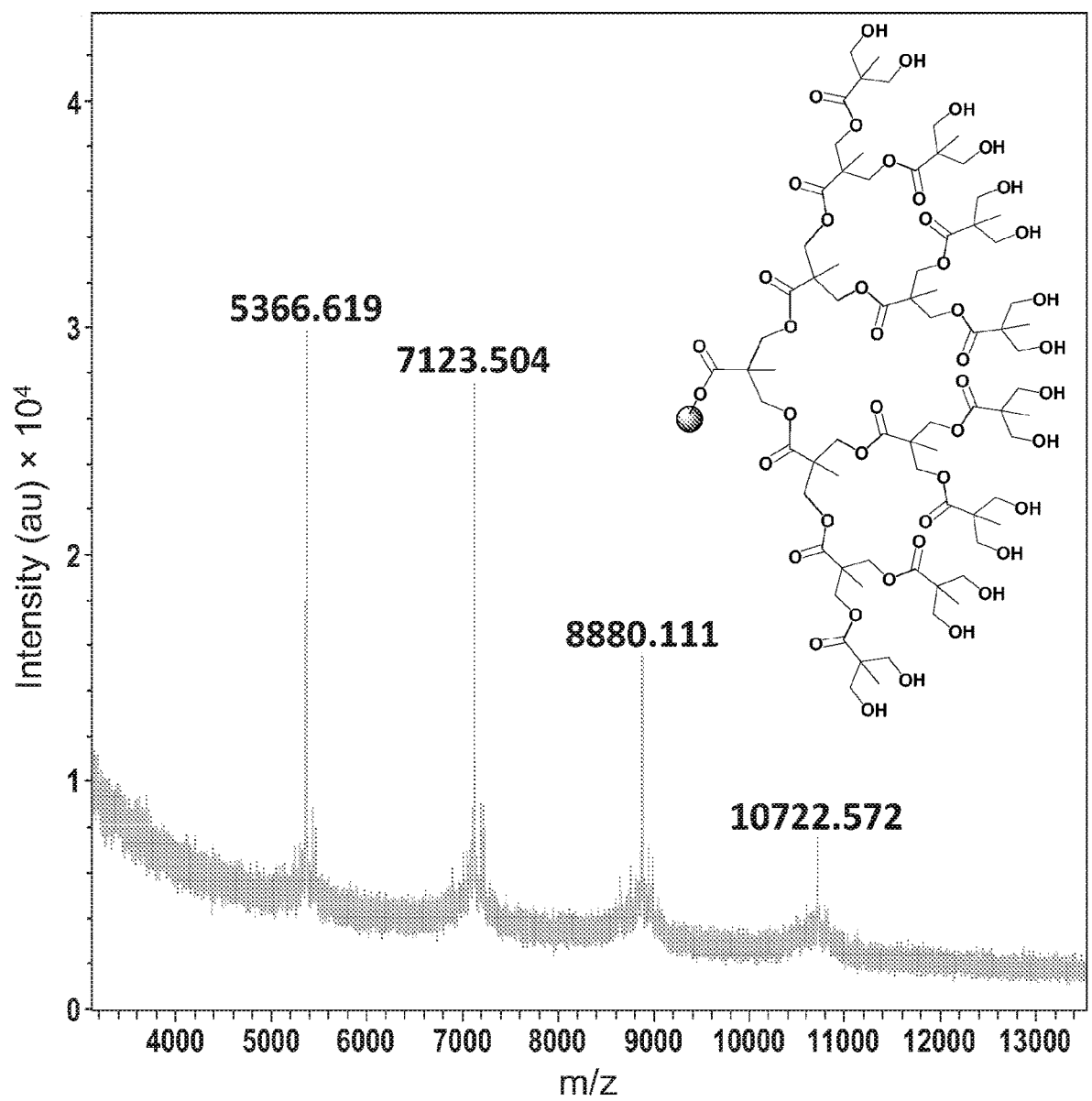
FIG. 12 shows the results of MALDI-TOF analysis of an equimolar mixture of dendrimers 8, 18, 28, and 38 of the present disclosure.

Synthesis of CX-([G-3]OH$_8$)$_z$, an equimolar mixture of dendrimers 6, 16, 26, 36 (see, e.g., reaction scheme of FIG. 5): The mixture of benzylidene protected dendrimers 5, 15, 25, and 35 from EXAMPLE 13 was deprotected using 5% Pd(OH)$_2$/C and hydrogen gas following the General Deprotection Procedure of EXAMPLE 4, to afford the CX-([G-3]OH$_8$)$_z$, mixture of dendrimers 6, 16, 26, 36. As shown in FIG. 10, MALDI-TOF MS: Theoretical Exact MW: [M+Na]$^+$ m/z=2,580.063; 3,408.389; 4,236.715; 5,151.115. Observed MW: [M+Na]$^+$ m/z=2,580.10; 3,408.41; 4,236.80; 5,151.28. As can be appreciated from FIG. 10, the mixture of dendrimers 6, 16, 26, and 36 provides an effective four point calibration that covers the 2,500-5,100 mass range.

Example 15

Parallel Synthesis of Dendrimers 7, 17, 27, and 37

Synthesis of CX-([G-4]Ph$_8$)$_z$, an equimolar mixture of dendrimers 7, 17, 27, and 37 (see, e.g., reaction scheme of FIG. 5): The mixture of hydroxyl functionalized dendrimers 6, 16, 26, and 36 from EXAMPLE 14 was esterified following the General Dendronization Procedure of EXAMPLE 3, using the benzylidene-protected Bis-MPA anhydride, and DMAP to afford the CX-([G-4]Ph$_8$)$_z$, mixture of dendrimers 7, 17, 27, and 37. MALDI-TOF MS: Theo. Avg. MW: [M+Ag]$^+$ m/z=7,561.9; 10,022.8; 12,483.8; 15,030.8. Observed MW: [M+Ag]$^+$ m/z=7,562; 10,023; 12,484; 15,031. As can be appreciated from FIG. 11, the mixture of dendrimers 7, 17, 27, and 37 provides an effective four point calibration that covers the 7,500-15,000 mass range.

Example 16

Parallel Synthesis of Dendrimers 8, 18, 28, and 38

Synthesis of CX-([G-4]OH$_{16}$)$_z$, an equimolar mixture of dendrimers 8, 18, 28, and 38: The mixture of benzylidene protected dendrimers 7, 17, 27, and 37 from EXAMPLE 15 was deprotected using 5% Pd(OH)$_2$/C and hydrogen gas following the General Deprotection Procedure of EXAMPLE 4, to afford the CX-([G-4]OH$_{16}$)$_z$ mixture of dendrimers 8, 18, 28, and 38. MALDI-TOF MS: Theo. Avg. MW: [M+Na]$^+$ m/z=5,365.2, 7,121.9; 8,878.6; 10,721.4. Observed MW: [M+Na]$^+$ m/z=5,366.619; 7,123.504; 8,880.111; 10,722.572. As can be appreciated from FIG. 12, the mixture of dendrimers 8, 18, 28, and 38 provides an effective four point calibration that covers the 5,500-10,500 mass range.

Example 17

Parallel Synthesis of Dendrimers 9, 19, 29, and 39

Synthesis of CX-([G-5]Ph$_{16}$)$_z$, an equimolar mixture of dendrimers 9, 19, 29, and 39: The mixture of hydroxyl functionalized dendrimers 8, 18, 28, and 38 from EXAMPLE 16 would be esterified following the General Dendronization Procedure of EXAMPLE 3, using the benzylidene-protected Bis-MPA anhydride of EXAMPLE 3 and DMAP to afford the CX-([G-5]Ph$_{16}$)$_z$ mixture of dendrimers 9, 19, 29, and 39. MALDI-TOF MS: Theo. Avg. MW: [M+Ag]$^+$ m/z=15,244.9; 20,266.9; 25,288.8; 30,396.9. Observed MW: [M+Ag]$^+$ m/z=to be determined.

Example 18

Parallel Synthesis of Dendrimers 10, 20, 30, and 40

Synthesis of CX-[G-5]OH$_{32}$)$_z$, an equimolar mixture of dendrimers 10, 20, 30, and 40: The mixture of benzylidene protected dendrimers, 9, 19, 29, and 39 from EXAMPLE 17 would be deprotected using 5% Pd(OH)$_2$/C and hydrogen gas following the General Deprotection Procedure of EXAMPLE 4, to afford the CX-([G-5]OH$_{32}$)$_z$ mixture of dendrimers 10, 20, 30, and 40. MALDI-TOF MS: Theo. Avg. MW: [M+Na]$^+$ m/z=10,935.5; 14,548.9; 18,162.4; 21,861.9. Observed MW: [M+Na]$^+$ m/z=to be determined Example 19

Calibrant Tests—Dendronized Cavitand

Figure 13A:
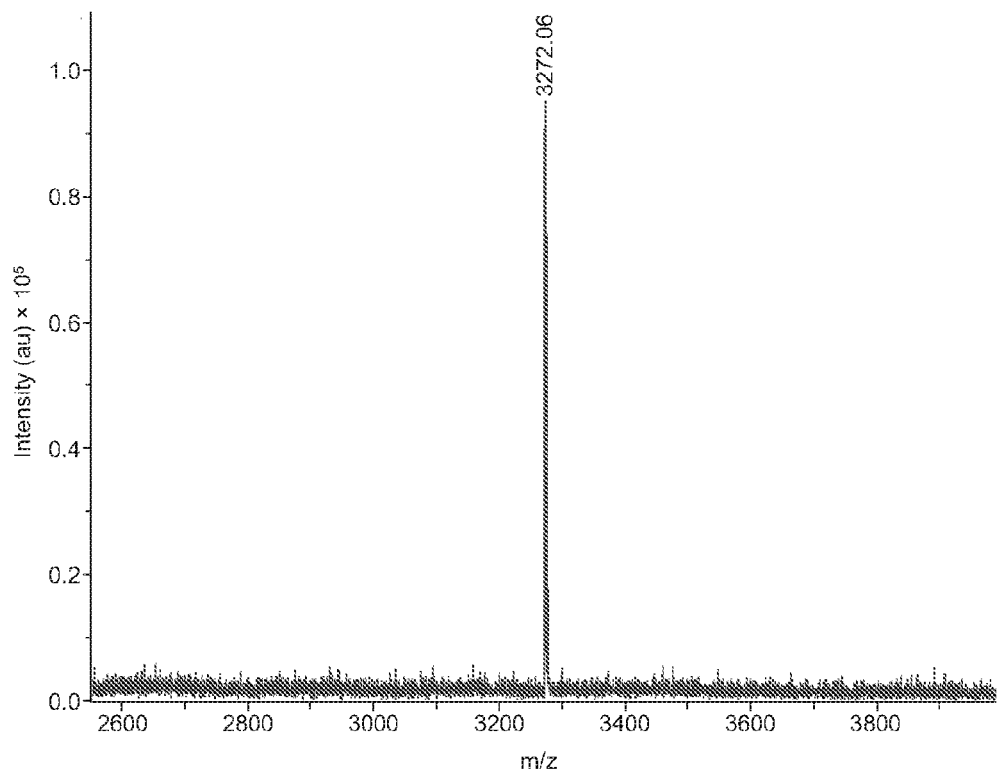
FIG. 13A shows the spectrum results of MALDI-TOF analysis of a dendronized cavitand (Cav-([G1]-Ph)$_8$, having molecular formula $C_{192}H_{176}O_{48}$.
Figure 13B:
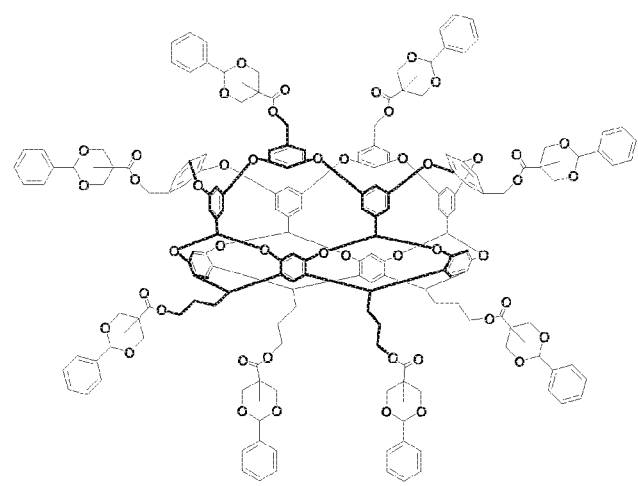
FIG. 13B shows the structure of the dendronized cavitand from FIG. 13A.

To verify the utility of the calibrants of the present disclosure in acquiring accurate MALDI-TOF data with high mass resolution, a dendronized cavitand (a monodisperse synthetic molecule) was examined, and the results are shown in FIG. 13A. The dendronized cavitand (Cav-([G1]-Ph)$_8$, as shown in FIG. 13B) has the molecular formula C$_{192}$H$_{176}$O$_{48}$, MALDI-TOF MS: Theoretical Exact MW: [M+Na]$^+$ m/z=3,272.122. Observed MW: [M+Na]$^+$ m/z=3,272.06. Mass Accuracy: 18.9 ppm.

Example 20

Calibrant Test—Poly(ethylene) Glycol, PEG 1970

Figure 14:
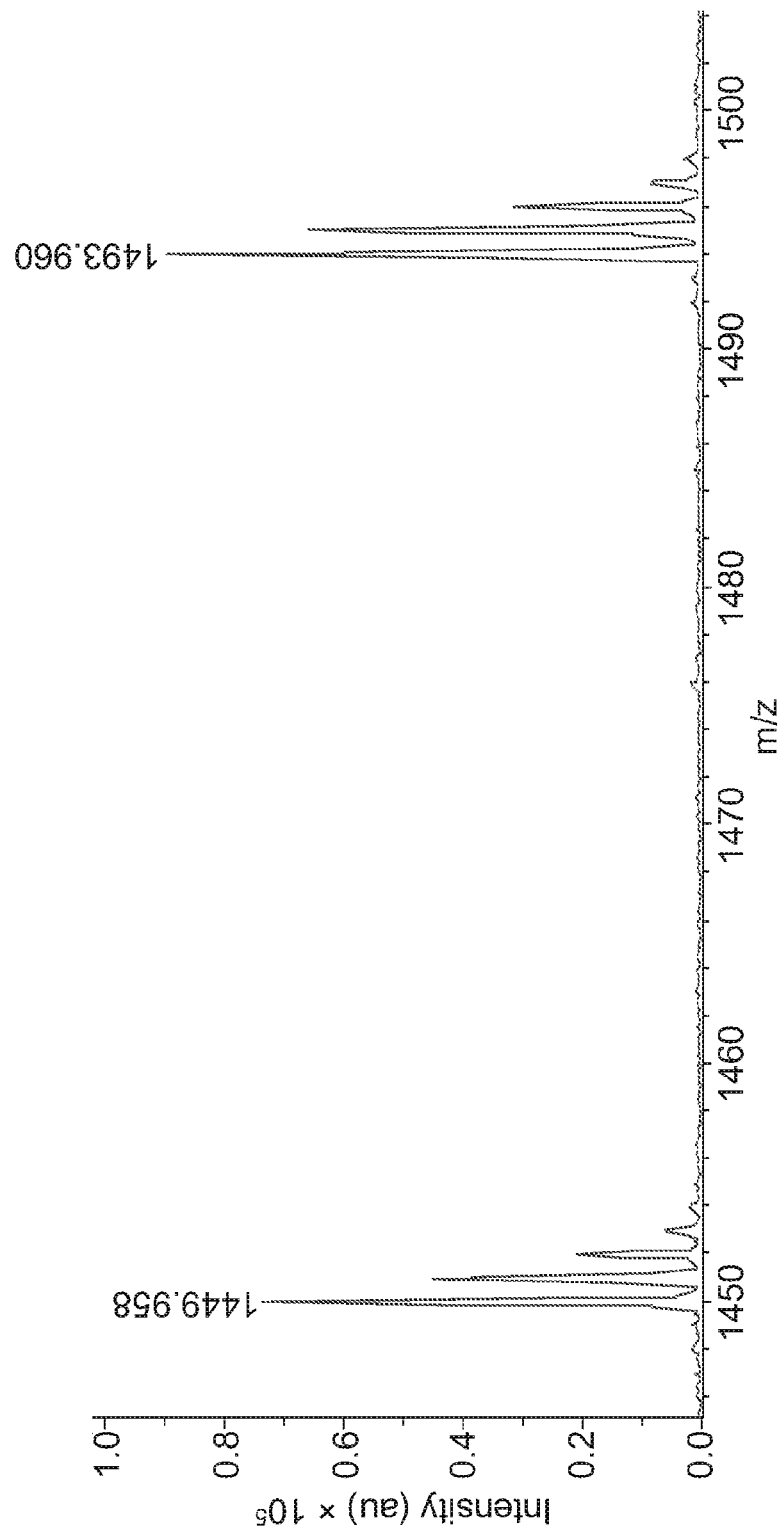
FIG. 14 shows the results of MALDI-TOF analysis of the PEG 1970 33-mer, having the molecular formula $C_{66}H_{134}O_{34}$.
Figure 15:
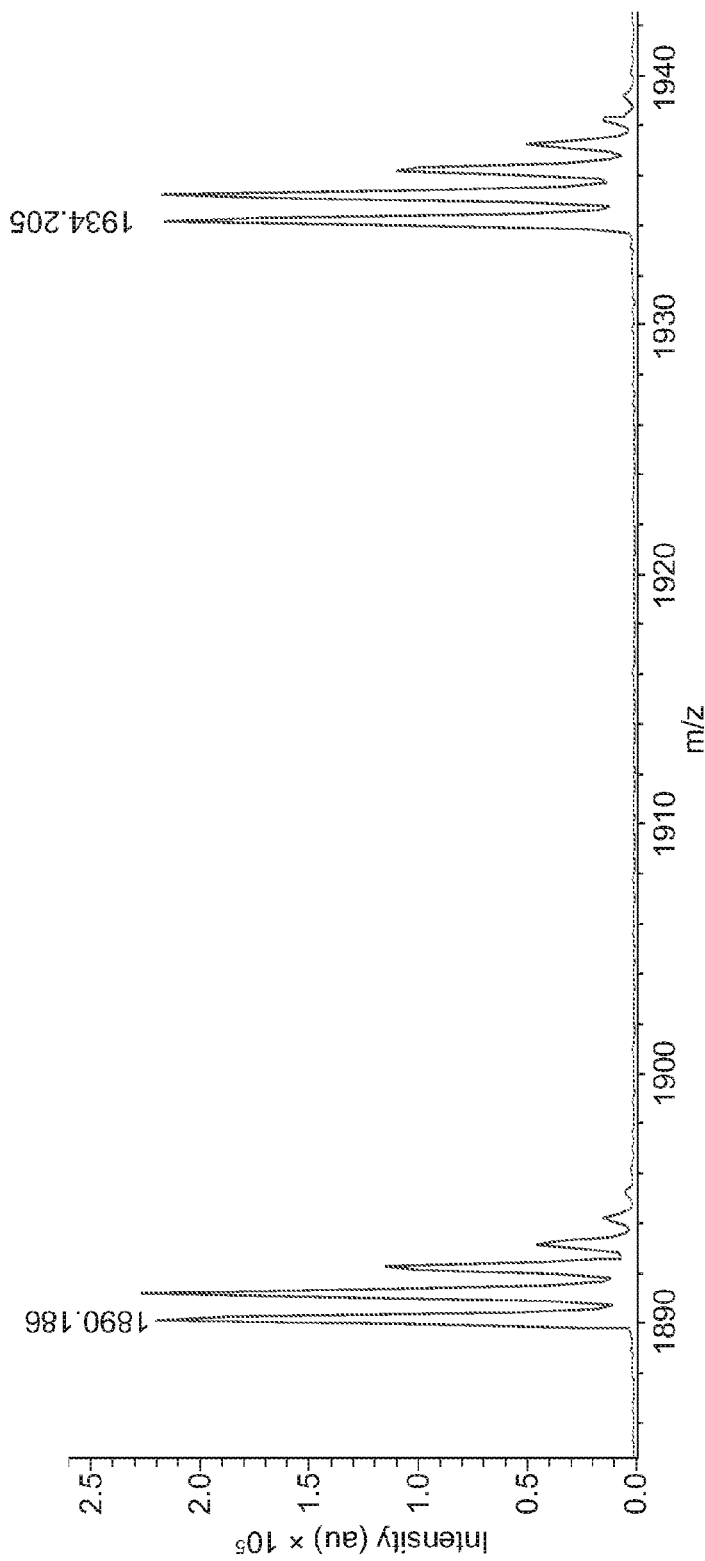
FIG. 15 shows the results of MALDI-TOF analysis of the PEG 1970 43-mer, having the molecular formula $C_{86}H_{174}O_{44}$.
Figure 16:
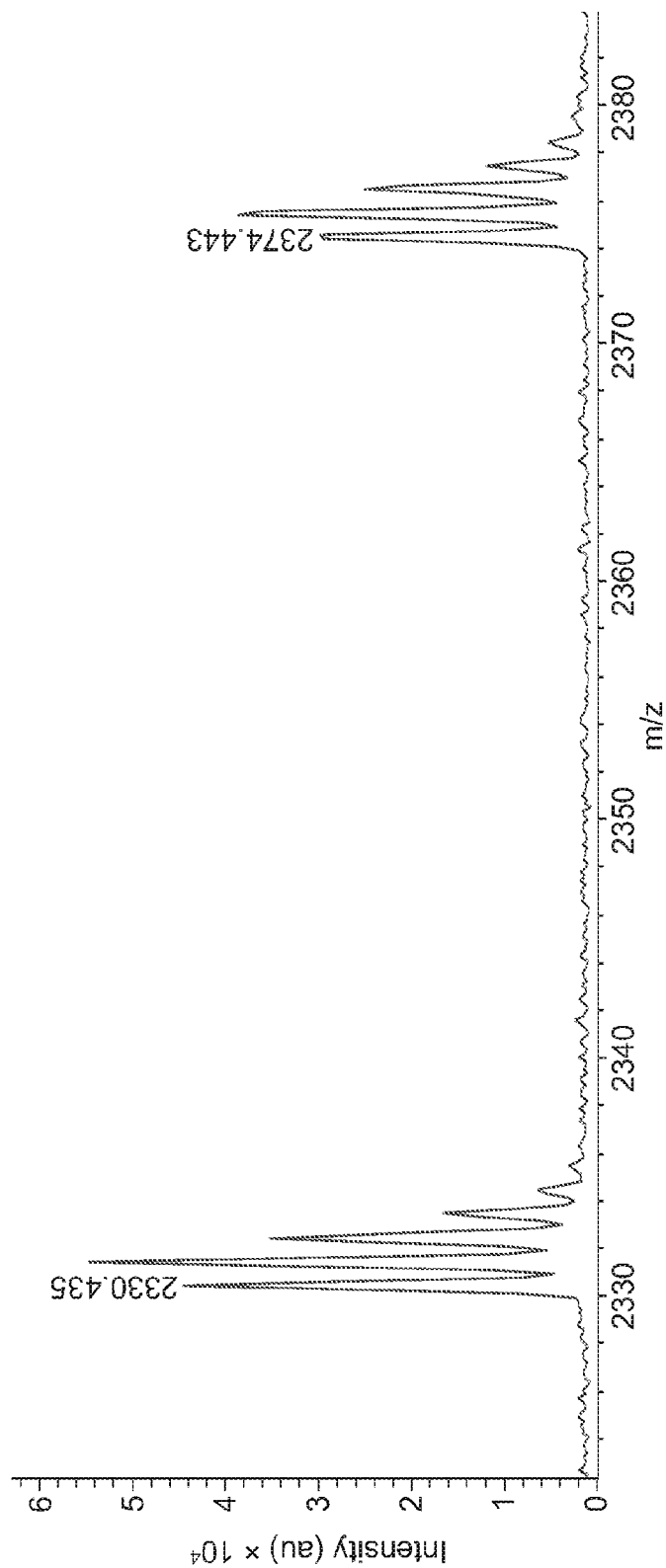
FIG. 16 shows the results of MALDI-TOF analysis of the PEG 1970 53-mer, having the molecular formula $C_{106}H_{214}O_{54}$.

To further verify the utility of the calibrants of the present disclosure in acquiring accurate MALDI-TOF data with high mass resolution, synthetic polymer PEG 1970 (a polydisperse polymer of three different oligomers: a 33-mer, a 43-mer, and a 53 mer), was examined. The number average molecular weight (M$_n$) of PEG 1970 is 1970, and its polydispersity index (PDI) is 1.05. The spectrometric results are shown in FIGS. 14-16.

The PEG 1970 33-mer has the molecular formula C$_{66}$H$_{134}$O$_{34}$. As shown in FIG. 14, MALDI-TOF MS: Theoretical Exact MW: [M+Na]$^+$ m/z=1493.865. Observed MW: [M+Na]$^+$ m/z=1493.96. Mass Accuracy: 63.6 ppm.

The PEG 1970 43-mer has the molecular formula C$_{86}$H$_{174}$O$_{44}$. As shown in FIG. 15, MALDI-TOF MS: Theoretical Exact MW: [M+Na]$^+$ m/z=1934.127. Observed MW: [M+Na]$^+$ m/z=1934.20. Mass Accuracy: 37.7 ppm.

The PEG 1970 53-mer has the molecular formula $C_{106}H_{214}O_{54}$. As shown in FIG. 16, MALDI-TOF MS: Theoretical Exact MW: $[M+Na]^+$ m/z=2374.389. Observed MW: $[M+Na]^+$ m/z=2374.44. Mass Accuracy: 21.5 ppm.

Example 21

Calibrant Test—Proprietary Peptide JF-1485

Figure 17:
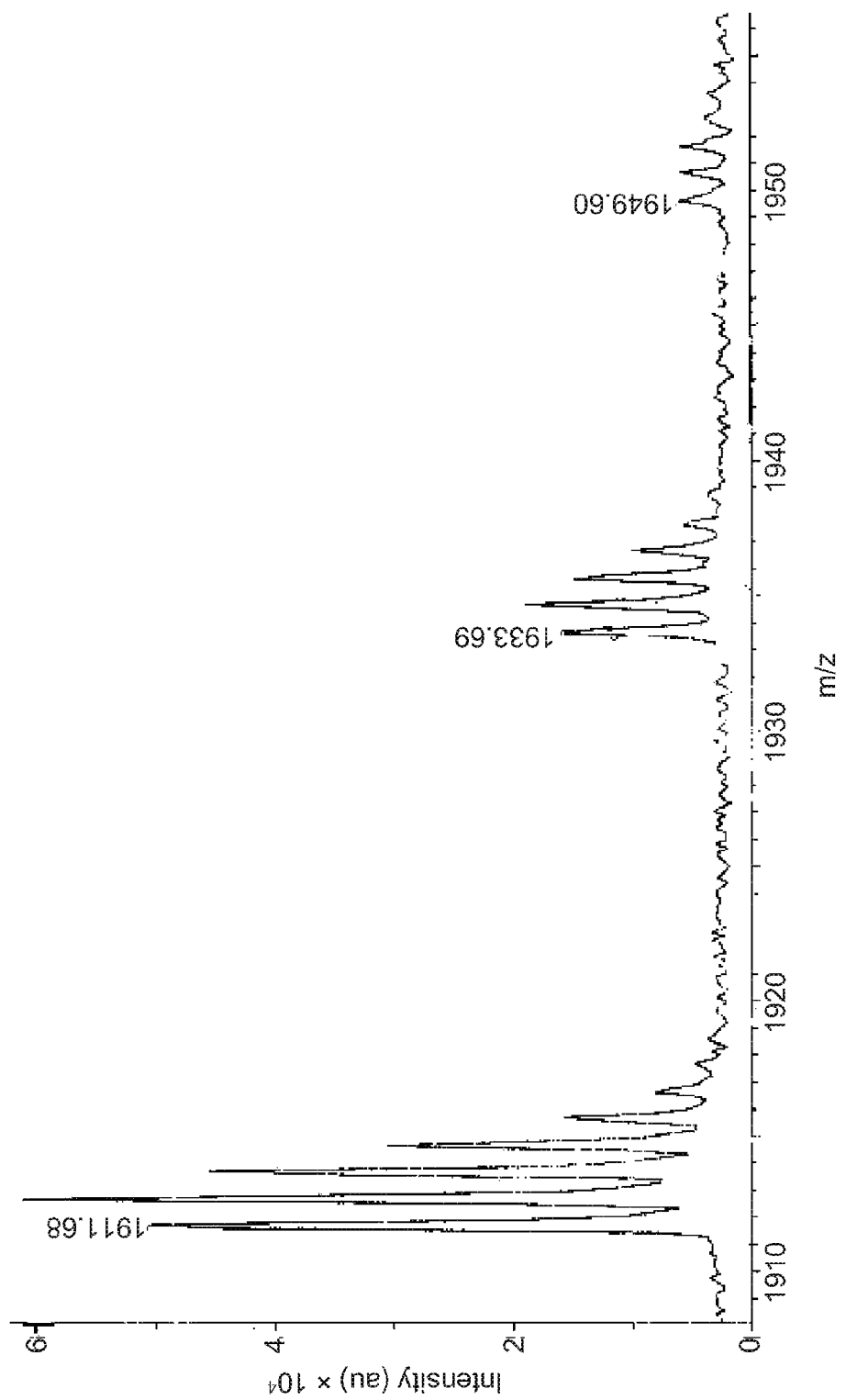
FIG. 17 shows the results of MALDI-TOF analysis of the proprietary peptide JF-1485, having the formula $C_{88}H_{118}N_{16}O_{22}S_{5+}$.
Figure 18:
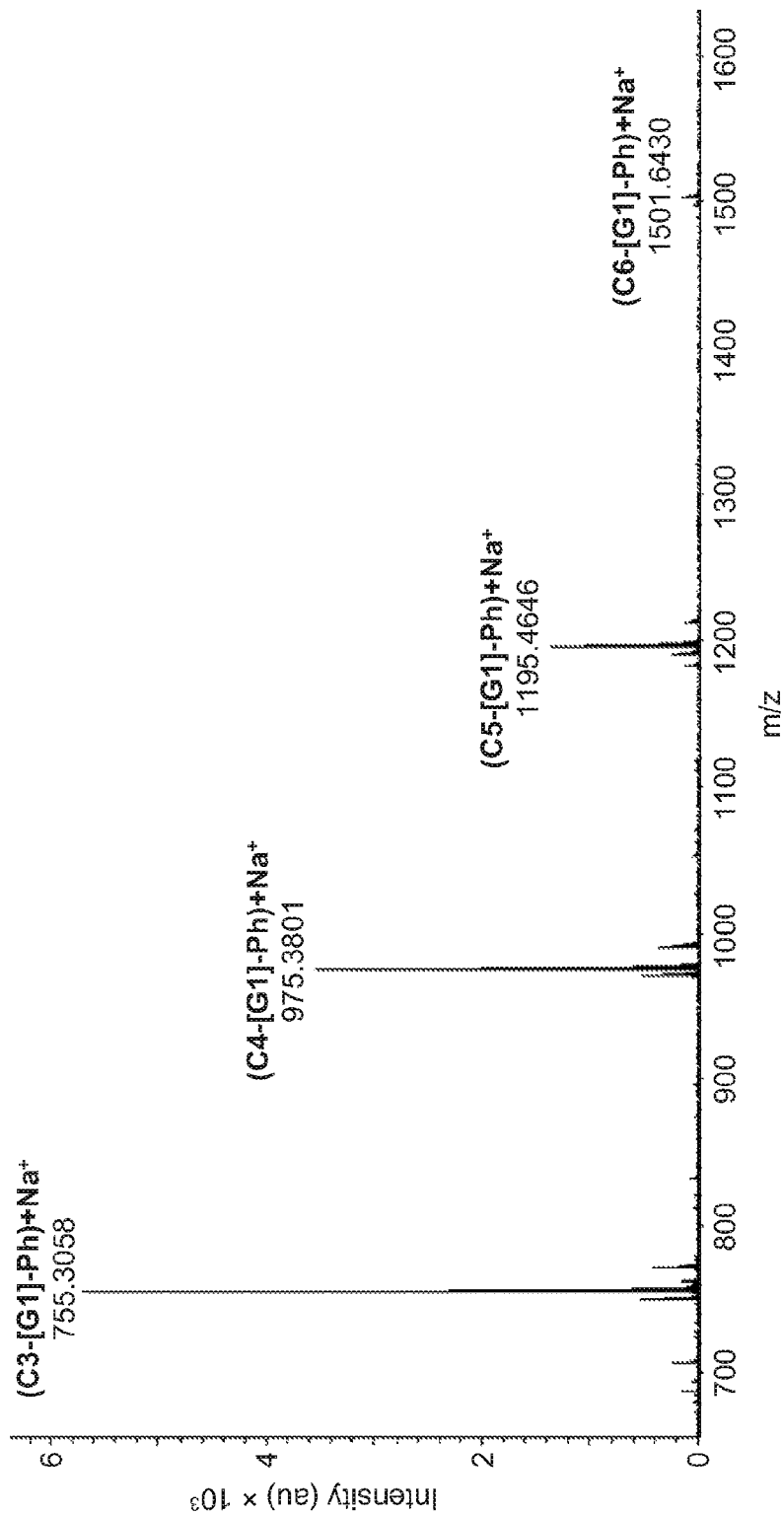
FIG. 18 shows an ESI-mass spectrum of G1 mixture of dendrimers 1 (C3-([G-1]Ph)$_3$), 11 (C4-([G-1]Ph)$_4$), 21 (C5-([G-1]Ph)$_5$), and 31 (C6-([G-1]Ph)$_6$). Samples were prepared by dissolving in acetonitrile and injecting directly without addition of counterion. Residual sodium yielded the observed mass spectra with a single sodium cation.
Figure 19:
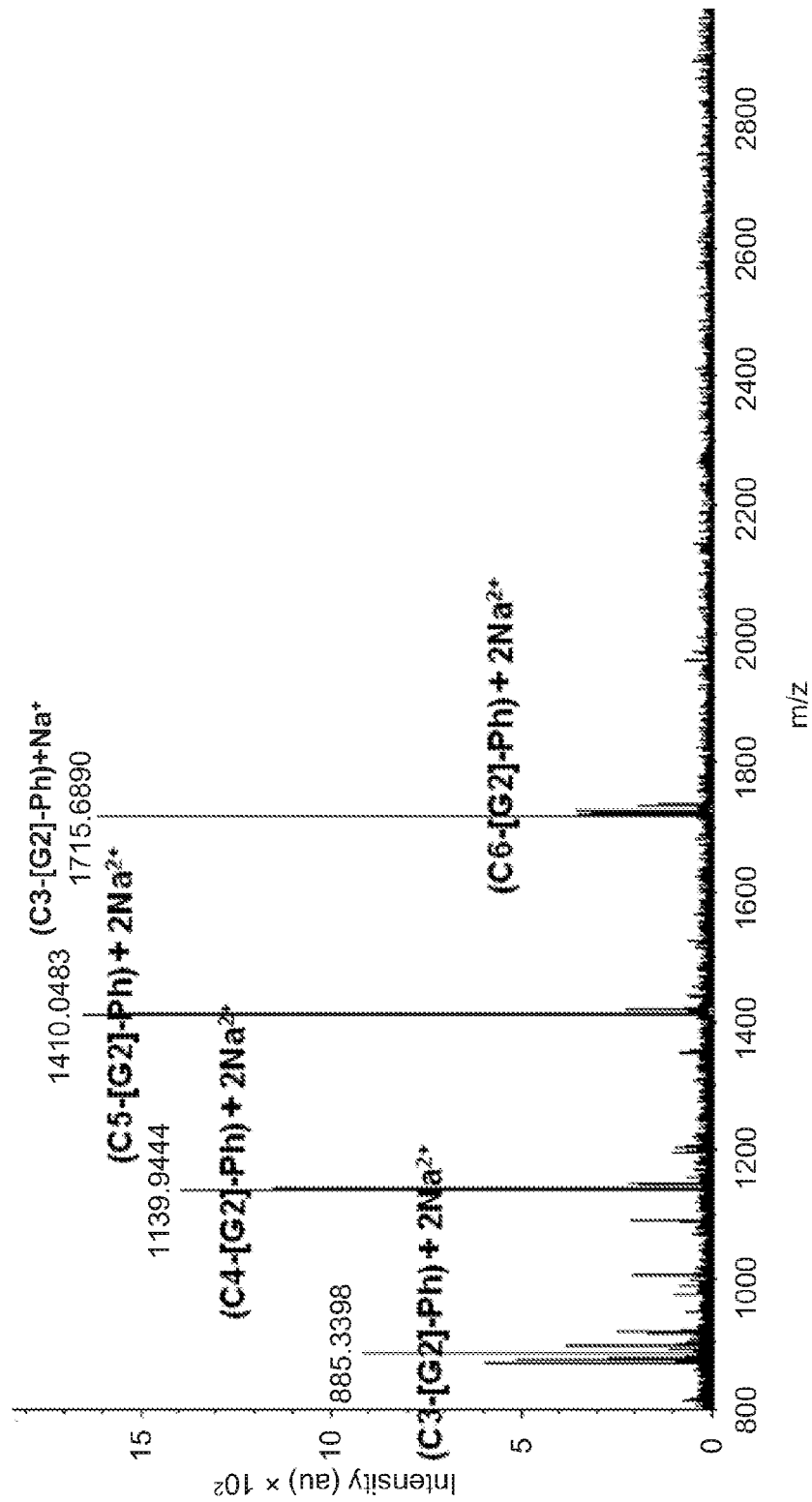
FIG. 19 shows an ESI-mass spectrum of G1 mixture of dendrimers 3 (C3-([G-2]Ph$_2$)$_3$), 13 (C4-([G2]Ph$_2$)$_4$), 23 (C5-([G-2]Ph$_2$)$_5$), and 33 (C6-([G-2]Ph$_2$)$_6$). Samples were prepared by dissolving in acetonitrile and injecting directly without addition of counterion. Residual sodium yielded the observed mass spectra with a single sodium cation for dendrimer 3, as well as doubly-charged complexes (two sodium cations) for dendrimers 13, 23, and 33.
Figure 20:
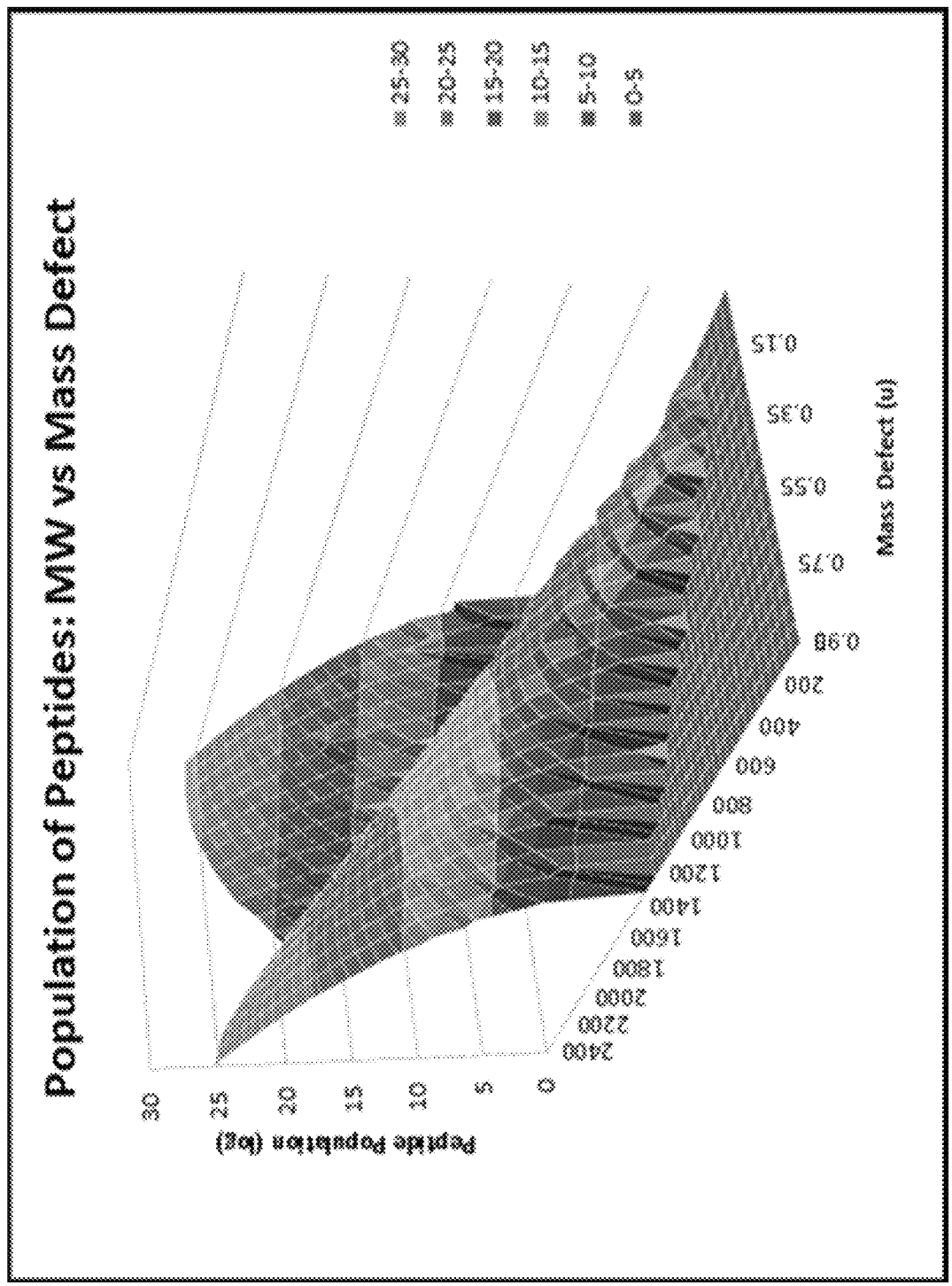
FIG. 20 shows a first view of a peptide population map wherein the graphical data represents the total population of all possible peptides per 0.01 u of mass defect for each nominal molecular weight.
Figure 21:
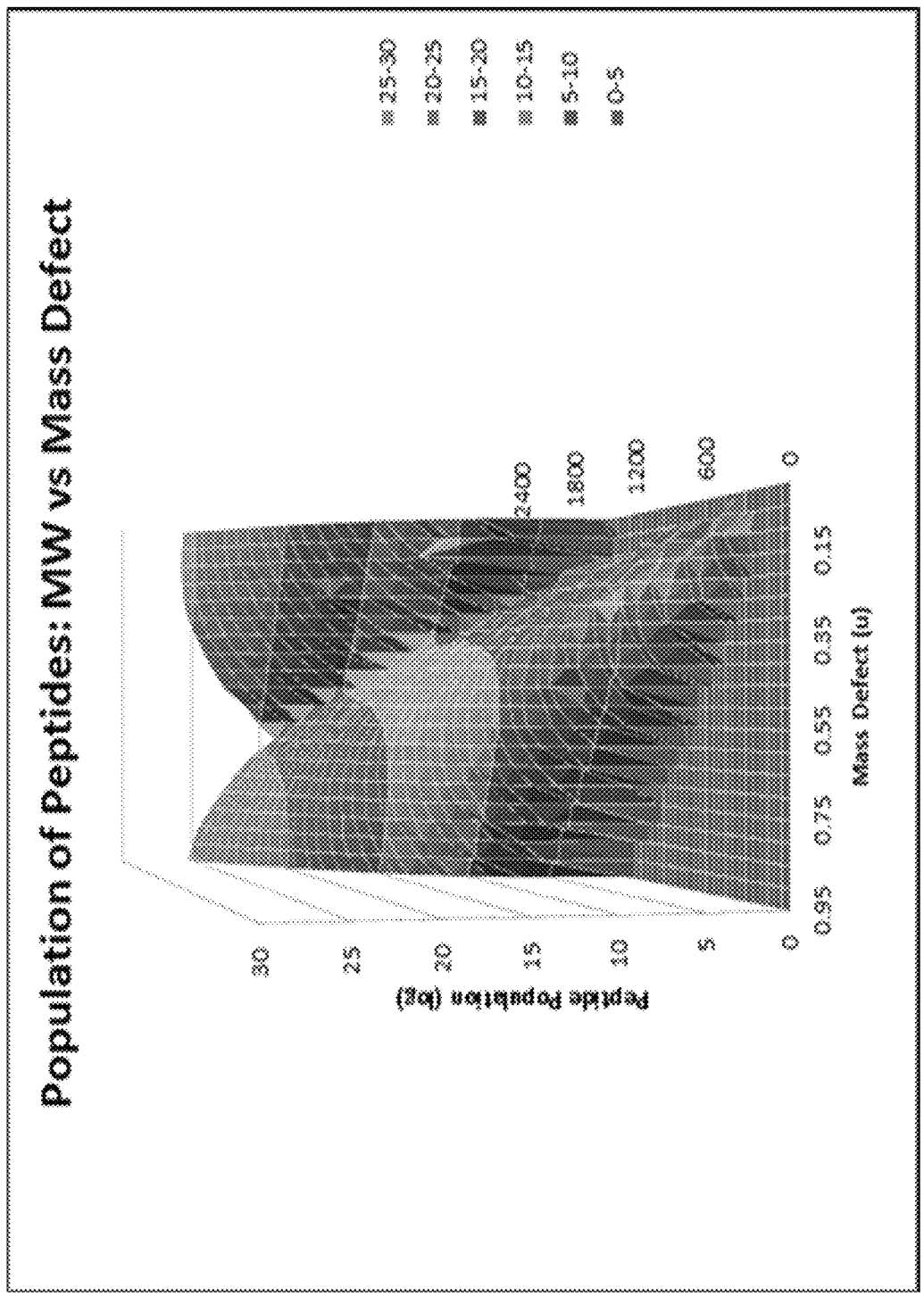
FIG. 21 shows a second view of said peptide population map wherein the graphical data represents the total population of all possible peptides per 0.01 u of mass defect for each nominal molecular weight.
Figure 22:
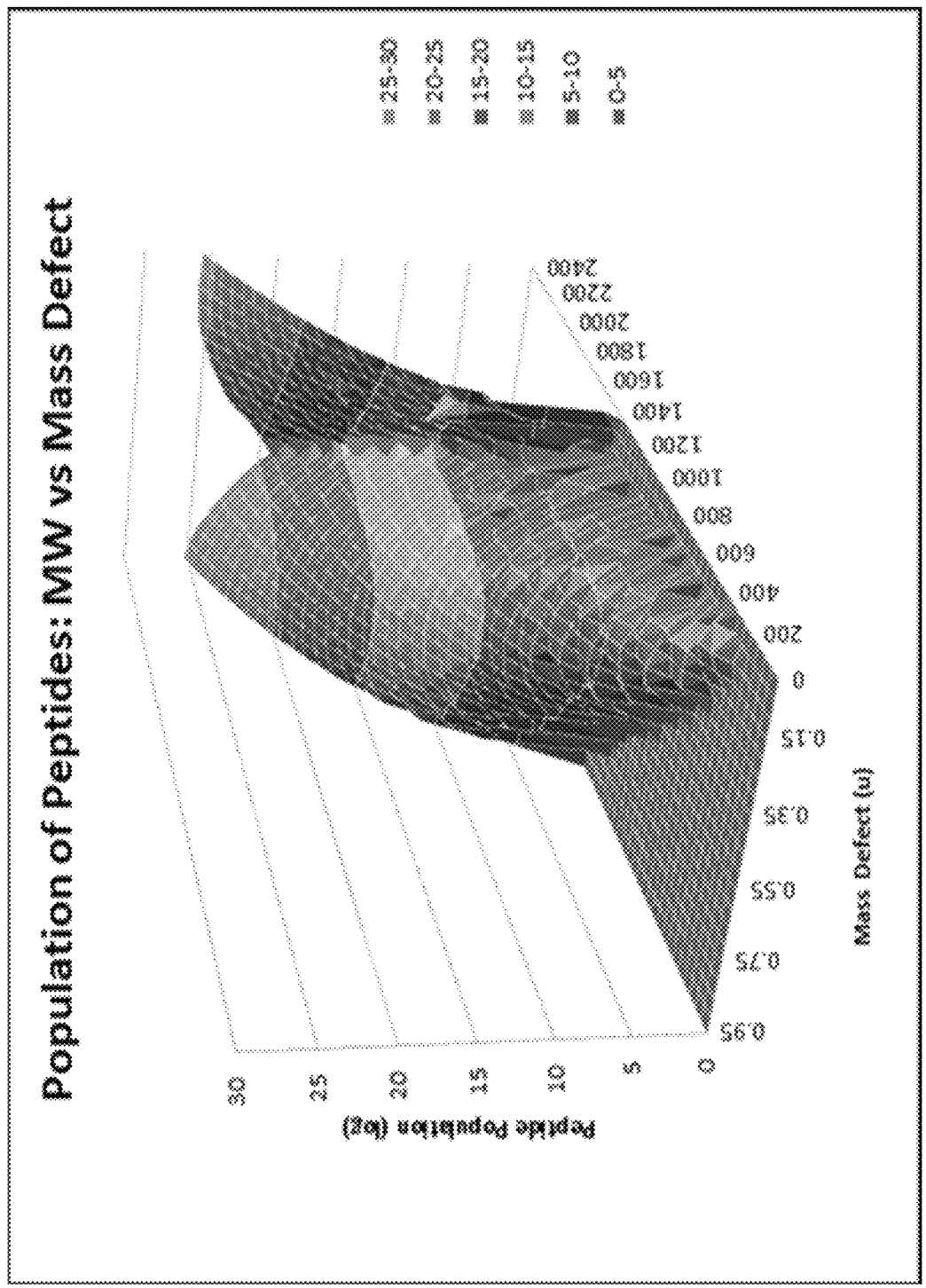
FIG. 22 shows a third view of said peptide population map wherein the graphical data represents the total population of all possible peptides per 0.01 u of mass defect for each nominal molecular weight.

To further verify the utility of the calibrants of the present disclosure in acquiring accurate MALDI-TOF data with high mass resolution, peptide JF-1485 having the formula $C_{88}H_{118}N_{16}O_{22}S_5$ (and having a proprietary structure) was examined. As shown in FIG. 17, MALDI-TOF MS: Theoretical Exact MW of the $H^+$ adduct $[M+H]^-$ m/z=1911.728. Observed MW: $[M+H]^+$ m/z=1911.68. Theoretical Exact MW of the $Na^+$ adduct: $[M+Na]^+$ m/z=1933.7102. Observed MW: $[M+Na]^+$ m/z=1933.69. Theoretical Exact MW of the $K^+$ adduct $[M+K]^+$ m/z=1949.6842 Observed MW: $[M+K]^+$ m/z=1949.60. Mass Accuracy: 25.1 ppm.

Alternative Hydroxyl-Terminated Cores

As will be appreciated by those having ordinary skill in the art, dendrimers of various functionalities other than the ones described above may be synthesized via the General Dendronization Procedure of EXAMPLE 3 followed (optionally) by the General Deprotection Procedure of EXAMPLE 4. This could be accomplished, for example, and without intending to be limited, simply by choosing a hydroxyl-terminated core different from the ones disclosed above (e.g., a core other than 1,1,1-tris(hydroxymethyl) ethane, pentaerythritol, xylitol, or dipentaerythritol) for the General Dendronization Procedure of EXAMPLE 3. Exemplary alternative hydroxyl-terminated cores include, without intending to be limited: tripentaerythritol (eight hydroxyl termini) and tetrapentaerythritol (ten hydroxyl termini). Those having ordinary skill in the art will also understand from the foregoing description that each dendrimer created via the General Dendronization Procedure of EXAMPLE 3 may also function as an alternative hydroxyl-terminated core. For example, the dendrimer denoted C3-([G-2]$OH_4)_3$—dendrimer 4 of FIG. 1—possesses twelve —OH termini, each of which may undergo a round of dendronization (via the General Dendronization Procedure of EXAMPLE 3). The resulting dendrimer may then undergo the General Deprotection Procedure of EXAMPLE 4 to yield yet another dendrimer, and the steps may be repeated to create even larger dendrimers. Thus, alcohols containing from about 1 to many hundreds of hydroxyl (—OH) termini may be used in the General Dendronization Procedure of EXAMPLE 3 (preferably polyalcohols, and including linear polyols such as poly(vinyl alcohol) and hyperbranched polyols such as poly(glycerols)), and followed (optionally) by the General Deprotection Procedure of EXAMPLE 4 to produce calibrants useful for mass spectrometry, especially for MALDI-TOF, ESI, APCI, and FAB techniques. Moreover, combinations of such alcohols (and preferably polyalcohols) may be used in parallel syntheses (e.g., as described in EXAMPLES 9-18) to create a panel of calibrants useful across a broad range of m/z ratios.

In addition, the coupling acylation chemistry used to covert alcohols to the corresponding esters during the "coupling" or "dendronization" step as described in EXAMPLE 3 is equally amenable to the acylation reaction, using the same reagents, that converts amines to amides. As a result, polyamine core molecules can also be used (as core molecules), including commercially available families of dendritic polyamine such as the poly(amidoamine)(PAMAM) and poly(propylene amine) (PPI) dendrimers.

Trismonomer

The benzylidene protected bis-MPA monomer described above may be modified by substituting a hydroxymethyl group for the pendent methyl group, to produce a protected trismonomer, as shown in Formula 1 below:

Formula 1

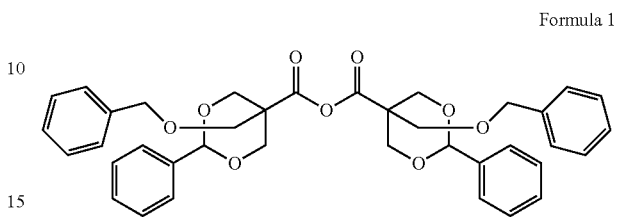

By substituting a hydroxymethyl group for the pendent methyl group of the benzylidene protected bis-MPA anhydride monomer ((bis(5-methyl-2-phenyl-1,3-dioxane-5-carboxylic) acid anhydride monomer), each dendrimer layer could contain three branches, rather than the two branches shown in FIGS. 1-5. In other words, by using the monomer of Formula 1 in the General Dendronization Procedure of EXAMPLE 3 and subsequently in the General Deprotection Procedure of EXAMPLE 4, each branch point would yield three branches, instead of the two branches shown in FIGS. 1-5. For example, by starting with 1,1,1-tris(hydroxymethyl) ethane and using the trismonomer of Formula 1 for one round of dendronization and deprotection according to EXAMPLES 3 and 4, respectively, a C3 calibrant—C3-([G-1]$OH_3)_3$—according to Formula 2 (and similar to dendrimer 2) would be produced:

Formula 2

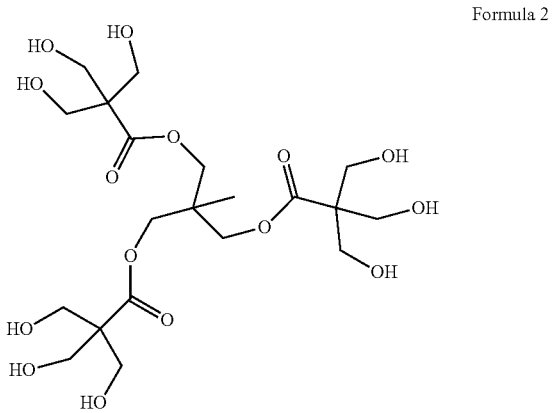 [SMILES: CC(COC(=O)C(CO)(CO)CO)(COC(=O)C(CO)(CO)CO)COC(=O)C(CO)(CO)CO]

The —OH groups of Formula 2 may be protected using methylidene orthoesters to carry out subsequent dendronization and deprotection steps.

Tuning the Dendrimers

Because the dendrimers described originate almost exclusively from the bis(hydroxymethyl)propanoic acid monomer, the composition of the overall structure can be easily tuned by subtle changes in the monomer structure. Such tuning could include modification of a pendant methyl group and/or synthesis of dendrimers using $^{12}C$ isotopically-enriched monomer.

The exact atomic masses of all atoms are close to, but not exactly, whole numbers. Because larger molecular weight (MW) compounds are comprised of multiple atoms, they have a significant mass defect—an offset from the nominal mass (the value of the nearest integer approximation of the most abundant isotope for each atomic mass). Simply put, the mass defect is the difference between the whole number approximate "nominal mass" and the actually-observed monoisotopic mass. The mass defect can be used to identify classes of compounds, and can be used to distinguish natural biomolecules from unnaturally modified ones. By tuning the elemental composition of the dendrimer backbone, the mass defect can be adjusted to ensure that they do not overlap with—and can be easily differentiated from—natural compounds. Such tuning can also facilitate automated data analysis by simplifying the distinction between analyte and calibrant. Because the disclosed dendrimers are made predominantly by multiple layers of the same monomer, tuning the elemental composition of that monomer allows the mass defect of all of the disclosed dendrimers to be tuned. For example, an average peptide will exhibit the "averagine" mass defect of +0.506 daltons (Da) per 1000 Da of molecular weight. "Averagine" is the theoretical "average" amino acid in regards to its elemental composition (with the non integer molecular formula: $C_{4.9384}H_{7.7583}N_{1.3577}O_{1.4773}S_{0.0417}$), and can be used to calculate the expected elemental composition and mass defect of peptides and proteins across a range of molecular weights. The hydroxyl-functionalized dendrons (see, e.g., dendrimers 2, 4, 6, 8, etc.) exhibit a mass defect of +0.42±0.02 Da per 1000 Da of molecular weight, while the benzylidene functionalized dendrons (see, e.g., dendrimers 1, 3, 5, 7, 9, etc.) exhibit a mass defect of 0.39±0.02 Da per 1000 Da of molecular weight. In order to differentiate this mass defect further, the pendant methyl of the hydroxyl-functionalized dendrons can be modified or functionalized with a variety of longer alkyl chains or with halogenated alkyl chains, without any significant effect on the synthetic procedure. This may be accomplished by modifying the benzylidene protected bis-MPA anhydride monomer (bis(5-methyl-2-phenyl-1,3-dioxane-5-carboxylic) acid anhydride monomer at the 5-methyl position as shown in Formula 3 below:

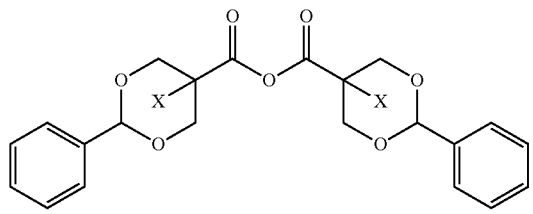

Formula 3

In Formula 3, X may be: alkyl (e.g., $CH_3$, $CH_2CH_3$, $CH_2CH_2CH_3$, or $(CH_2)_nCH_3$, where n is an integer from 0 to 16); $CH_2$—O—$CH_2$-Ph, where Ph represents phenyl; $CQ_3$, where "Q" represents a halogen, preferably fluorine (F) or chlorine (Cl) (e.g., $CF_3$, $CCl_3$, etc.); or $(CQ_2)_nCQ_3$, where "Q" represents a halogen, preferably fluorine (F) or chlorine (Cl), and where n is an integer from 1 to 16. For example, a rather significant shift in MW can be demonstrated by replacing the methyl group with a trifluoromethyl group, resulting in a shift in the mass defect to +0.11±0.02 Da per 1000 Da of MW. The molecular mass defect can also be modified by a simple functionalization of the periphery with a substituent with the desired mass defect. Despite modification at "X," dendrimer synthesis using the benzylidene protected monomer of Formula 3 may proceed via serial iterations of the General Dendronization Procedure of EXAMPLE 3 and the General Deprotection Procedure of EXAMPLE 4.

As the molecular weight of carbon-containing molecules increases, the natural prevalence of $^{13}C$ (natural abundance=1.109%) in the molecules leads to a broadening of the molecular isotopic distribution in their mass spectra. Above about 8,000 Da, the signal corresponding to the monoisotopic species (having only $^{12}C$) is so small, relative to polyisotopic species, that exact mass determination is difficult because the monoisotopic species' peak is difficult to identify amongst the peaks from polyisotopic species. Consequently, the presence of polyisotopic species greatly reduces the resolution of molecular weight calculations. Take, for example, Formula 4:

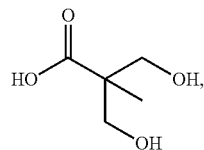

Formula 4 which can be represented by the formula $C_5H_{12}O_4$. Because greater than 1% of C is $^{13}C$, the MS of any carbon-containing compound will exhibit higher molecular weight signals corresponding to these $^{13}C$ isotopes. As the number of carbons in a compound increases, the likelihood that $^{13}C$ is present in the compound increases. This is seen in the isotopic distribution of the monomer of Formula 4, which has an exact mass of 136.07356, exhibits a monoisotopic signal at 136.07356 (m/z; 100.0% relative signal intensity), and a higher molecular weight species at 137.07691 (m/z; 5.4% relative signal intensity).

With increasing carbon content (e.g., without intending to be limited, 500 carbon atoms per molecule) the statistical distribution of molecular weights from different polyisotopic species becomes so broad that the single monoisotopic peak can become difficult to resolve. The native abundance of $^{12}C$ is 98.89%, of $^{13}C$ is 1.109%, of $^{1}H$ is 99.99%, of $^{2}H$ is 0.01%, of $^{16}O$ is 99.76%, of $^{18}O$ is 0.20%, and of $^{17}O$ is 0.04%. The $^{13}C$ isotope is the most common higher isotope in most organic compounds. Thus, the simplest way to narrow the isotopic distribution at high molecular weights is to start with building materials in which $^{13}C$ has been depleted—for example, starting materials in which all carbon is $^{132}C$.

Because the dendrimers described originate almost exclusively from the bis(hydroxymethy)propanoic acid monomer, if the synthesis is carried out with $^{12}C$ isotopically enriched monomer then the mass spectral peak broadening will be reduced substantially, and high accuracy calibration above 10,000 Da can be achieved easily. While isotopic broadening due to $^{18}O$ is much less pronounced (because $^{18}O$ represents only 0.201% of all O species) $^{16}O$ isotopic enrichment can also be carried out to improve the accuracy even further. These isotopic enrichments contemplated here are not expected to have any effect on the synthetic parameters, beyond subtly altering the molecular weights of the reactants and the dendrimer products.

As shown in the General Dendronization Procedure for Preparation of CX-([G-n]$Ph_p$)$_z$ described in EXAMPLE 3, the alcohol functionalities of the monomer must be "protected" in order to control the iterative dendrimer growth that yields exact monodisperse structures. Two alcohols can be protected simultaneously with benzylidene (described in EXAMPLE 3 and shown below at Formula 5), and those of ordinary skill in the art will also recognize that they may be protected with acetonide (Formula 6), or other acetal or ketal protecting group (see, e.g., Formulae 7 & 8, where $R^3$ is H or $CH_3$, $R^4$ is Ph, $CH_3$, $C_6H_4OCH_3$, or $C_6H_4NO_2$, $R_5$ is $CH_2Ph$, $Si(CH_3)_3$, $C_6H_5NO_2$, $CH_2OCH_3$, $C_5H_9O$ (Tetrahydropyranyl ether), or $SiPh_2t$-Bu, and where Ph is phenyl).

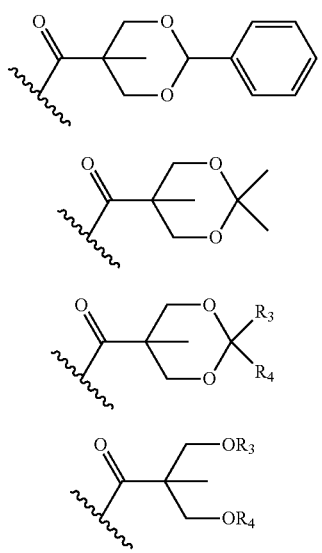

Formula 5

Formula 6

Formula 7

Formula 8

Further examples of protecting groups may be found in "Protective Groups in Organic Synthesis" by P. G. M. Wuts and T. W. Greene (4th edition, 2007, John Wiley and Sons Inc. Hoboken, NJ), which is incorporated by reference herein in its entirety. In addition, a number of labile ether linkages, including benzyl ethers, substituted benzyl ethers, and silyl ethers, can be also be used instead of, or in addition to, to enable the synthesis of structurally pure dendrimers. Such modifications to the dendronization procedure lie within the scope of the present disclosure.

Tuning the Dendrimers Via the Core Molecule

Another method of tuning is to modify the core molecule of the dendrimer. In one embodiment, the dendrimer is tuned so as to incorporate a specific element or elements not commonly found in biomolecules into the core molecule in order to create a dendritic calibrant with a mass defect marker distinct from common, natural biomolecules. By tuning the elemental composition of the dendrimer core molecule, the mass defect can be adjusted to ensure that the observed masses of the dendrimers do not overlap with—and therefore can be easily differentiated from—the more common natural compounds during mass spectrometry.

Fluorine, phosphorus and iodine are all speculated to be desirable elements for incorporation into the core molecule because they are believed to result in a comparatively stable dendrimer calibrant that further results in a mass spectral peak of a narrower width. Specifically, because halogens (e.g., fluorine, chlorine, bromine, iodine) are capable of relatively easily substituting for hydrogen atoms, and as such will bond with the carbons of the core molecule, they should result in relatively stable dendrimers. Furthermore, because fluorine, phosphorous and iodine are monoisotopic, their incorporation into the dendrimers should further result in a desirable relatively narrow mass spectral peak.

Additionally, it is preferable to incorporate an element with a larger negative mass defect into the core molecule as it results in a more substantial shift in the peak of the mass spectra. The mass defects for a sampling of various elements are provided in TABLE 2.

TABLE 2

| Element | Isotope | Atomic Mass (u) | Mass Defect | % Isotopic comp. | Mass defect per 1000 u |
|---|---|---|---|---|---|
| Hydrogen | $^1H$ | 1.00783 | 0.00783 | 99.9885 | 7.7692 |
|  | $^2H$ | 2.01410 | 0.01410 | 0.0115 | 7.0065 |
| Carbon | $^{12}C$ | 12.00000 | 0.00000 | 98.93 | 0.0000 |
|  | $^{13}C$ | 13.00335 | 0.00335 | 1.07 | 0.2576 |
| Nitrogen | $^{14}N$ | 14.00307 | 0.00307 | 99.632 | 0.2192 |
|  | $^{15}N$ | 15.00011 | 0.00011 | 0.368 | 0.0073 |
| Oxygen | $^{16}O$ | 15.99491 | −0.00509 | 99.757 | −0.3182 |
|  | $^{17}O$ | 16.99913 | −0.00087 | 0.038 | −0.0512 |
|  | $^{18}O$ | 17.99916 | −0.00084 | 0.205 | −0.4667 |
| Fluorine | $^{19}F$ | 18.99840 | −0.00160 | 100 | −0.0842 |
| Phosphorus | $^{31}P$ | 30.97377 | −0.02623 | 100 | −0.8468 |
| Sulfur | $^{32}S$ | 31.97207 | −0.02793 | 94.93 | −0.8736 |
|  | $^{33}S$ | 32.97146 | −0.02854 | 0.76 | −0.8656 |
|  | $^{34}S$ | 33.96787 | −0.03213 | 4.29 | −0.9459 |
| Chlorine | $^{35}Cl$ | 34.96885 | −0.03115 | 75.78 | −0.8908 |
|  | $^{37}Cl$ | 36.96885 | −0.03419 | 24.22 | −0.9248 |
| Bromine | $^{79}Br$ | 78.91834 | −0.08166 | 50.69 | −1.0347 |
|  | $^{81}Br$ | 80.90585 | −0.08371 | 49.31 | −1.0347 |
| Iodine | $^{127}I$ | 126.93032 | −0.09553 | 100 | −0.7526 |

Knowing the mass defect for each dement, one skilled in the art can create a graphical representation of the total population of all possible peptides (composed of the 20 standard amino acids) per 0.01 u of mass defect for each nominal molecular weight. Such a graphical representation is shown, in various views, in FIGS. 20-23.

As can be seen in FIGS. 20-23, the graphical representation is defined by two prominent features: (1) an "averagine ridge" and (2) a "scarcine valley." The averagine ridge follows the trend of the average amino acid ($C_{4.9384}H_{7.7583}N_{1.3577}O_{1.4773}S_{0.0417}$) with exact molecular weight of 111.05431. The scarcine valley represents the least likely mass defects for a given molecular weight.

Thus, in use as a calibrant, it is desirable to have a dendrimer tuned so that it has a mass defect that falls within the scarcine valley. In one embodiment, this can be accomplished by using a dendrimer calibrant with 2,4,6-triiodalphenol as the core molecule, as shown in Formula 9.

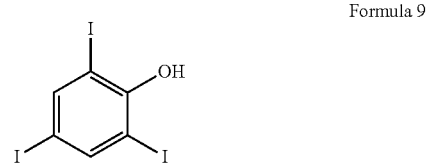

Formula 9

In alternative embodiments, various other tuned core molecules can be utilized. Such core molecules include, but are not limited to, hydroxyl-functional cores such as pentose sugars (linear and furanose forms), hexaose sugars (linear, pyranose and furanose forms), oligomers of pentose sugars, oligomers of hexose sugars, and cyclodextrins.

Other core molecules may include, but are not limited to, amino-functional cores such as diethylenetriamine [$N^1$-(2-aminoethyl)ethane-1,2-diamine], N,N'-Bis(3-aminopropyl) ethylenediamine[$N^1$,$N^{1'}$-(ethane-1,2-diyl)bis(ethane-1,2-diamine)], bis(hexamethylene)triamine [$N^1$-(6-aminohexyl)

hexane-1,6-diamine], spermidine [N¹-(3-aminopropyl)butane-1,4-diaimine], tetraethylenepentamine [N¹,N¹¹-(ethane-1,2-diyl)bis(N²-(2-aminoethyl)ethane-1,2-diamine)], spermine [N¹,N¹¹-(butane-1,4-diyl)bis(propane-1,3-diamine)], N,N'-bis(2-aminoethyl)1,3-propanediamine [N¹,N¹¹-(propane-1,3-diyl)bis(ethane-1,2-diamine)], and pentaethylenehexamine [N¹-(2-aminoethyl)-N²-(2-((2-((2-aminoethyl)amino)ethyl)amino) ethyl)amino)ethyl)ethane-1,2-diamine].

Yet other core molecules may include, but are not limited to, hydroxyl-functional tertiary amine cores such as N-methyldiethanolamine [2,2'-(methylazadiyl)diethanol], N-ethyldiethanolamine [2,2'-(ethylazadiyl)diethanol], N-propyldiethanolamine [2,2'-(propylazadiyl)diethanol], N-butyldiethanolamine [2,2'-(propylazadiyl)diethanol], N,N-Bis(2-hydroxyethyl)-p-toluidine [2,2'-(p-tolylazadiyl)diethanol], N,N-bis(2-hydroxyethyl)-m-toluidine [2,2'-(m-tolylazadiyl)diethanol], N-phenyldiethanolamine [2,2'-(phenylazadiyl)diethanol], triethanolamine [2,2',2"-nitrilotriethanol], 1-(N,N-bis(2-hydroxyethyl)-amino)-2-propanol [2,2'-((2-hydroxypropyl)azanediyl)diethanol], triisopropanolamine [1,1',1"-nitrilotris(propan-2-ol)], 3-(dimethylamino)-1,2-propanediol, 3-(diethylamino)-1,2-propanediol, 3-(dipropylamino)-1,2-propanediol, 3-(diisopropylamino)-1,2-propanediol, 2-bis(2-hydroxyethyl)amino-2-(hydroxymethyl)-1,3-propanediol (also known as bis-tris), N,N,N',N'-tetrakis(2-hydroxypropyl)ethylenediamine [1,1',1"',1"'-(ethane-1,2-diylbis(azanetriyl)) tetrakis(propan-2-ol)], N,N,N',N'-tetrakis(2-Hydroxyethyl)ethylenediamine, and pentrol [1,1',1",1"'-((((2-hydroxypropyl)azanediyl)bis(ethane-2,1-diyl))bis (azanetriyl))tetrakis(propan-2-d)].

Further core molecules may include, but are not limited to, amino-functional tertiary amine cores such as tris(aminoethyl)amine [N',N'-bis(2-aminoethyl)ethane-1,2-diamine] and N,N,N',N'-tetrakis(3-aminopropyl)-1,4-butanediamine [N¹,N¹'-(butane-1,4-diyl)bis(N¹-(3-aminopropyl) propane-1,3-diamine)].

Additional core molecules may include, but are not limited to, hydroxyl or amino functional iodocores such as 2,4,6-triiodophenol, 2,4,6-triiodophenyl)methanol, 2,4,6-triiodoaniline, (2,4,6-triiodophenyl)methanamine, iohexol [N¹,N³-bis(2,3-dihydroxypropyl)-5-(N-(2,3-dihydroxypropyl)acetamido)-2,4,6-triiodoisophthalamide], and iodixanol [N¹,N¹'-(2-hydroxypropane-1,3-diyl)bis(N³-(2,3-dihydroxpropyl)-5-(N-(2,3-dihydxypropyl)acetamido)-2,4,6-triiodoisophthalamide)].

Further additional core molecules may include, but are not limited to, hydroxyl-functional tertiary amine iodocores such as 2,2'-((2,4,6-triiodophenyl)azanediyl)diethanol, 2,2'-((2,4,6-triiodobenzyl)azanediyl)diethanol and 3,3'-(((5-((2,3-dihydroxypropyl)(ethyl)amino)-2,4,6-triiodo-1,3-phenylene)bis(methylene))bis(azanediyl))bis(propane-1,2-diol).

Example 22

General Dendronization Procedure for Preparation of CX-([G-n]Ac$_p$)$_z$

Figure 24:
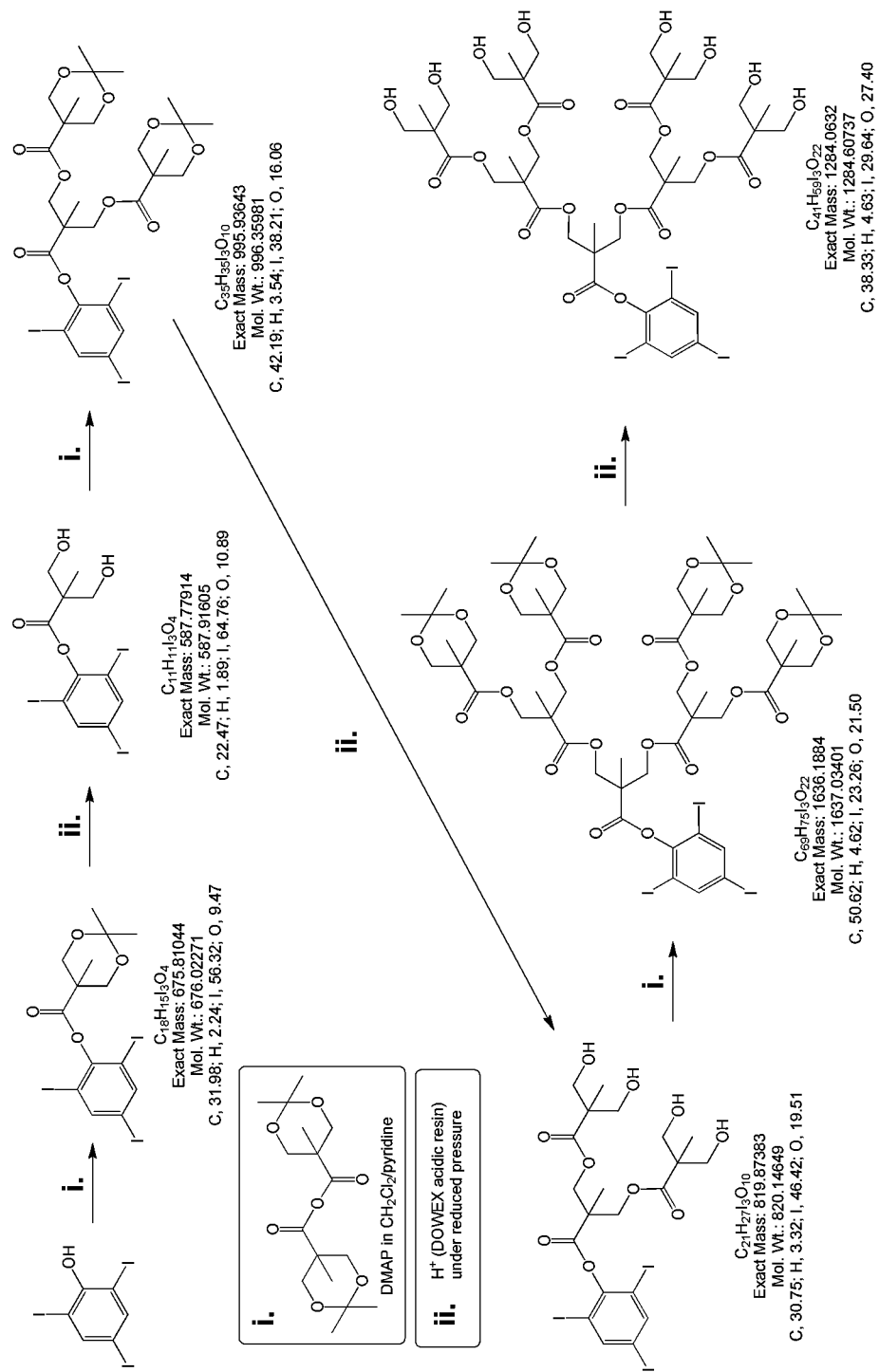
FIG. 24 is a schematic diagram showing the synthesis of mono-functional "C-1" iodo-core calibrants of the present disclosure.

The procedure of this EXAMPLE is shown schematically as step "i" of FIG. 24 (e.g., the syntheses of: dendrimer 1 from hydroxyl-terminated core; of dendrimer 3 from dendrimer 2; etc.). To a round bottom flask were added: a known quantity of either hydroxyl-terminated core (e.g., 2,4,6-triiodolphenol) or of dendrimer (e.g., one having the general formula CX-([G-(n−1)]OH$_r$)$_z$, where "r" has a value of $2^{(n-1)}$, as appropriate; 1.1 equivalents (per —OH of hydroxyl-terminated core or of dendrimer) of the acetonide protected bis-MPA anhydride monomer (2,2,5-trimethyl-1,3-dioxane-5-carboxylic) acid anhydride monomer); and 0.1 molar equivalents (per —OH of hydroxyl-terminated core or of dendrimer) of 4-dimethylaminopyridine (DMAP). The reaction mixture was dissolved in the minimum amount of pyridine, diluted in twice that amount (relative to pyridine) of dichloromethane, and the reaction mixture was then stirred vigorously for 4 hours at standard temperature and pressure. The reaction was monitored periodically by MALDI-TOF MS to determine the degree of coupling. After complete esterification was observed by MALDI-TOF MS, the flask contents were transferred to a separatory funnel, diluted with dichloromethane, extracted three times with 1M aqueous NaHSO$_4$ (sodium bis sulfate) and three extractions with 1M aqueous NaHCO$_3$ (sodium bicarbonate). The organic layers were reduced in vacuo to concentrate the sample, precipitated into hexanes, and filtered to yield the benzylidene protected dendrimers, CX-([G-n]Ac$_p$)$_z$, as a white powdery precipitate. The resulting precipitate may then be prepared for spectrometric analysis via standard protocols.

Example 23

General Deprotection Procedure for Preparation of CX-([G-n]OH$_q$)$_z$

The procedure of this EXAMPLE is shown schematically as step "ii" of FIG. 1 (e.g., the syntheses of: dendrimer 2 from dendrimer 1; of dendrimer 4 from dendrimer 3; etc.). To a round bottom flask, a measured quantity of CX-([G-n]Ac$_r$)$_z$, where "r" has a value of $2^{(n-1)}$ was added and dissolved in 1:1 toluene/methanol. Dowex® solid phase acid resin was added to this solution and the temperature was adjusted to 70° C. The reaction was stirred vigorously for 2-3 hours, and we speculate that reduced pressure could be used to expedite the reaction. The deprotection was monitored by MALDI-TOF MS and when completed, the Dowex® was filtered from the reaction using methanol. The filtrate was then reduced in vacuo to yield a transparent glassy solid having the formula CX ([G-n]OH$_q$)$_z$. The resulting filtrate may then be prepared for spectrometric analysis via standard protocols.

Example 24

Synthesis of Iodo-Core Calibrants

The iodo-core dendrimer species of this EXAMPLE 24 are shown in FIG. 24.

Synthesis of C1-([G-1]Ac)$_1$, dendrimer 1 of FIG. 24: 2,4,6-triiodolphenol was esterified following the General Dendronization Procedure of EXAMPLE 22, using the acetonide-protected Bis-MPA anhydride of EXAMPLE 2 and DMAP to afford C1-([G-1]Ac)$_1$. Molecular Formula: $C_{14}H_{15}I_3O_4$. MALDI-TOF MS: Theoretical Exact MW: [M+Na]⁻ m/z=650.80021. Observed MW: [M+Na]⁺ m/z=650.66.

Synthesis of C1-([G-1]OH$_2$)$_1$, dendrimer 2 of FIG. 24: The acetonide protected dendrimer 1 was deprotected using DOWEX® solid phase acid resin following the General Deprotection Procedure of EXAMPLE 23, to afford C1-([G-1]OH$_2$)$_1$. Molecular Formula: $C_{11}H_{11}I_3O_4$. MALDI-TOF MS: Theoretical Exact MW: [M+Na]⁺ m/z=610.769. Observed MW: [M+Na]⁺ m/z=610.753.

Synthesis of C1-([G-2]Ac$_2$)$_1$, dendrimer 3 of FIG. 24: The hydroxylated dendrimer 2, was esterified following the General Dendronization Procedure of EXAMPLE 22, using the acetonide-protected Bis-MPA anhydride of EXAMPLE 2 and DMAP to afford C1-([G-2]Ac$_2$)$_1$. Molecular Formula: C$_{27}$H$_{33}$I$_3$O$_{10}$. MALDI-TOF MS: Theoretical Exact MW: [M+Na]$^+$ m/z=922.92620. Observed MW: [M+Na]$^+$ m/z=922.97.

Synthesis of C1-([G-2]OH$_4$)$_1$, dendrimer 4 of FIG. 24: The acetonide protected dendrimer 3 was deprotected using DOWEX® solid phase acid resin following the General Deprotection Procedure of EXAMPLE 23, to afford C1-([G-2]OH$_4$)$_1$. Molecular Formula: C$_{21}$H$_{27}$I$_2$O$_{10}$. MALDI-TOF MS: Theoretical Exact MW: [M+Na]$^+$ m/z=842.864. Observed MW: [M+Na]$^+$ m/z=842.85.

Synthesis of C$_1$-([G-3]Ac$_4$)$_1$, dendrimer 5 of FIG. 24: The hydroxylated dendrimer 4, was esterified following the General Dendronization Procedure of EXAMPLE 22, using the acetonide-protected Bis-MPA anhydride of EXAMPLE 2 and DMAP to afford C1-([G-3]Ac$_4$)$_1$. Molecular Formula: C$_{53}$H$_{75}$I$_3$O$_{22}$. MALDI-TOF MS: Theoretical Exact MW: [M+Na]$^+$ m/z=1467.17817. Observed MW: [M+Na]$^+$ m/z=1467.07.

Synthesis of C1-([G-3]OH$_8$)$_1$, dendrimer 6 of FIG. 24: The acetonide protected dendrimer 5 was deprotected using DOWEX® solid phase acid resin following the General Deprotection Procedure of EXAMPLE 23, to afford C1-([G-3]OH$_8$)$_1$. Molecular Formula: C$_{41}$H$_{59}$I$_3$O$_{22}$. MALDI-TOF MS: Theoretical Exact MW: [M+Na]$^+$ m/z=1307.050. Observed MW: [M+Na]$^+$ m/z=1306.98.

Figure 23:
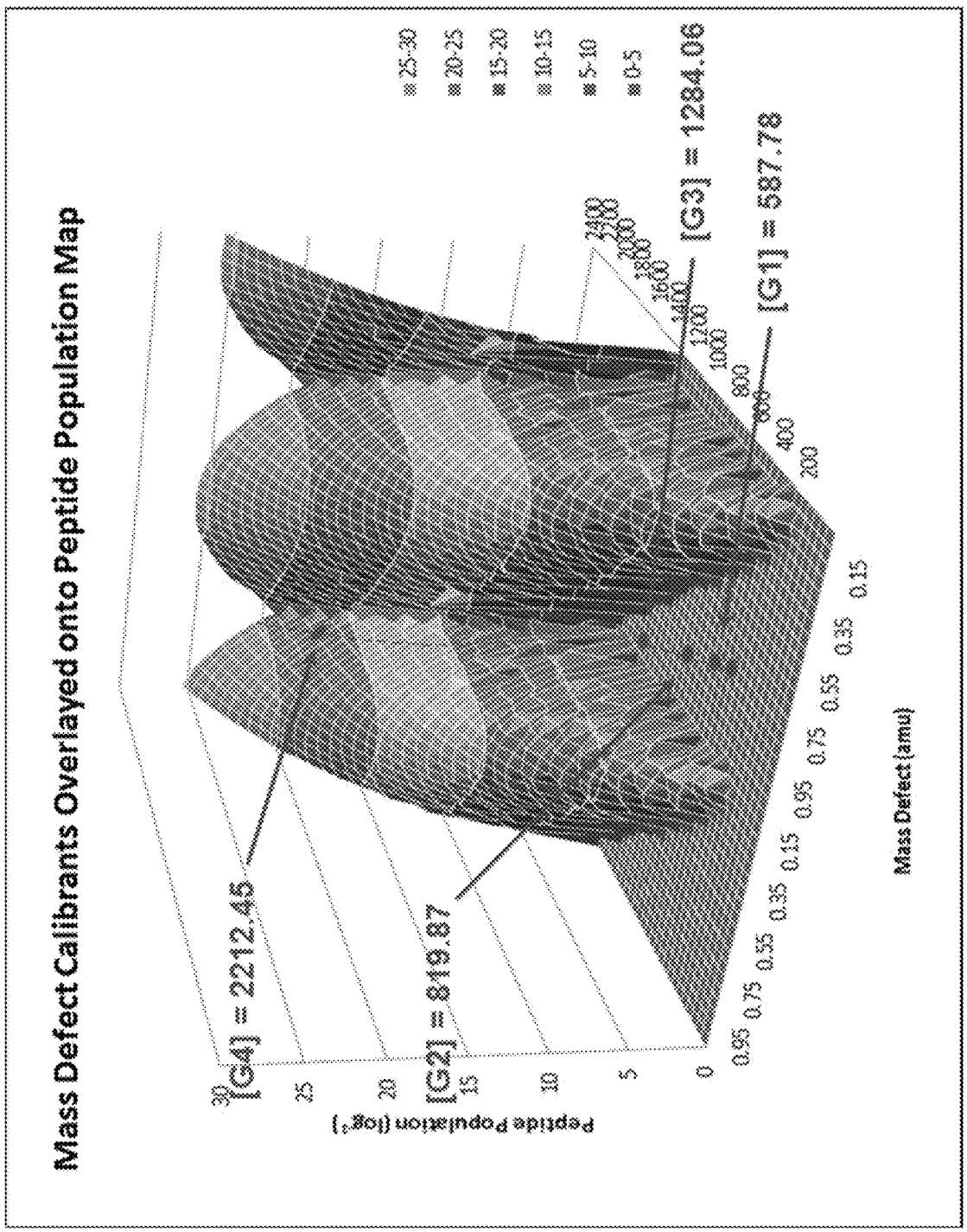
FIG. 23 shows a peptide population map configured to show the scarcine ridge wherein the graphical data represents the total population of all possible peptides per 0.01 u of mass defect for each nominal molecular weight.
Figure 25:
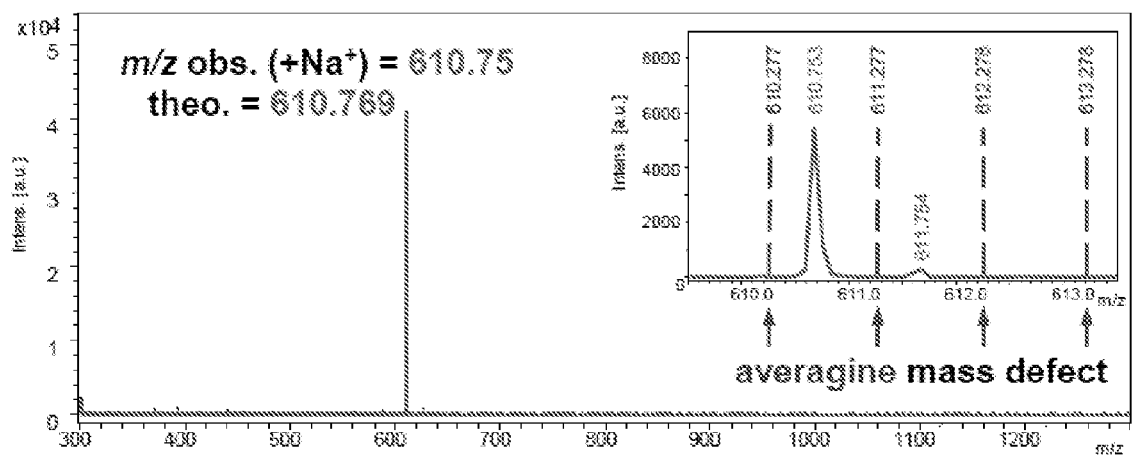
FIG. 25 shows the results of MALDI-TOF analysis of iodo-core dendrimer 2 of the present disclosure.
Figure 26:
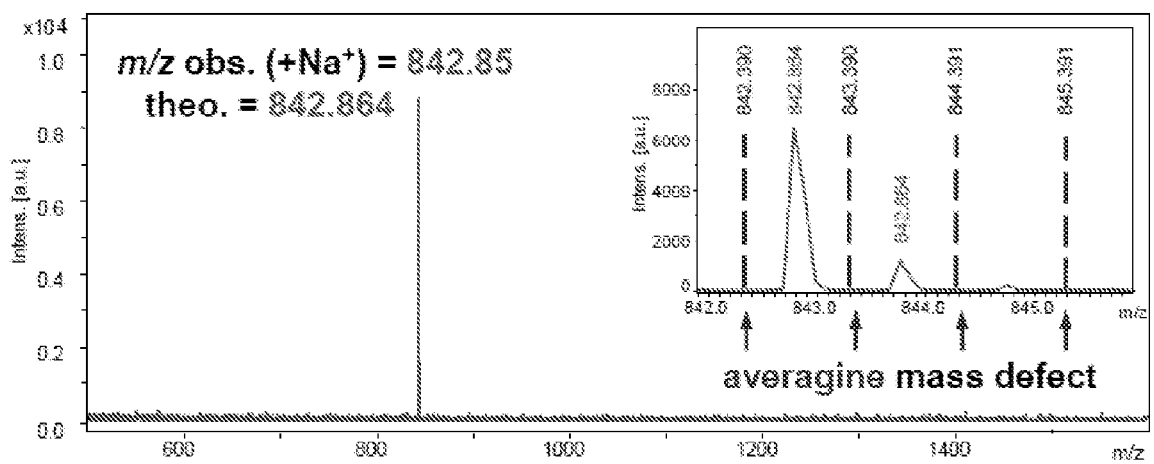
FIG. 26 shows the results of MALDI-TOF analysis of iodo-core dendrimer 4 of the present disclosure.
Figure 27:
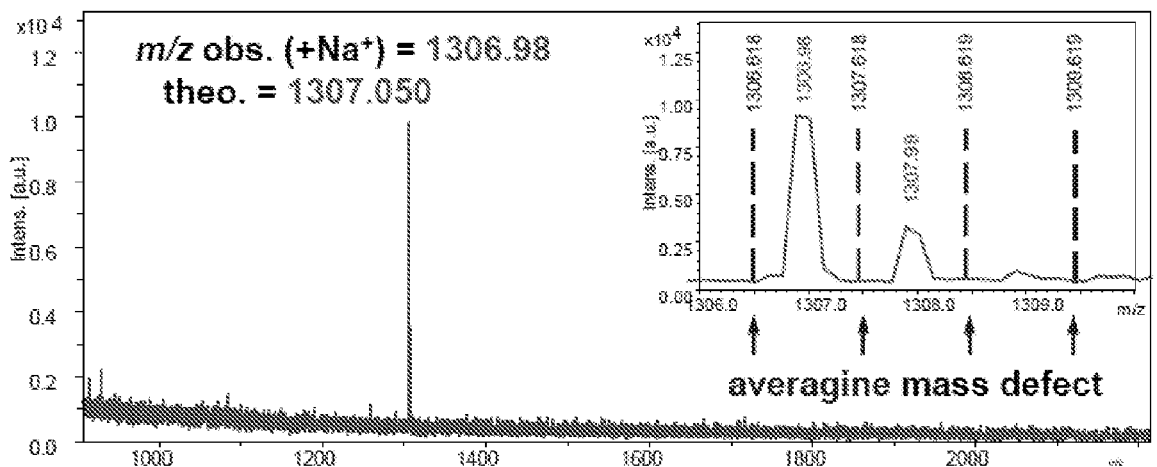
FIG. 27 shows the results of MALDI-TOF analysis of iodo-core dendrimer 6 of the present disclosure.

The dendrimers (dendrimers 2, 4 and 6) made according to the above examples yield a calibrant that is easily distinguishable from naturally occurring peptides and peptidic fragments. "First generation" dendrimer 2 (as shown in FIG. 24) has a molecular weight (with sodium counterion) of 610.769 (as demonstrated in FIG. 25). As further demonstrated in FIG. 25, the mass spectra peak for the first generation dendrimer falls clearly to the right of, and does not overlap with, the averagine molecular weight of 610.277. "Second generation" dendrimer 4 (as shown in FIG. 24) has a molecular weight (with sodium counterion) of 842.864 (as demonstrated in FIG. 26). As further demonstrated in FIG. 26, the mass spectra peak for the second generation dendrimer falls dearly to the right of (by approximately 0.5 u), and does not overlap with, the averagine molecular weight of 842.390. "Third generation" dendrimer 6 (as shown in FIG. 24) has a molecular weight (with sodium counterion) of 1307.050 (as demonstrated in FIG. 27). As further demonstrated in FIG. 27, the mass spectra peak for the third generation dendrimer falls dearly to the right of, and does not overlap with, the averagine molecular weight of 1306.618. Additionally, as shown in FIG. 23, when the first (labeled as G1), second (labeled as G2) and third generation (labeled as G3) dendrimers are overlayed onto the peptide population map, the dendrimers clearly fall within the scarcine ridge.

Example 25

Internal Calibration Test—Endomorphin I

Figure 28:
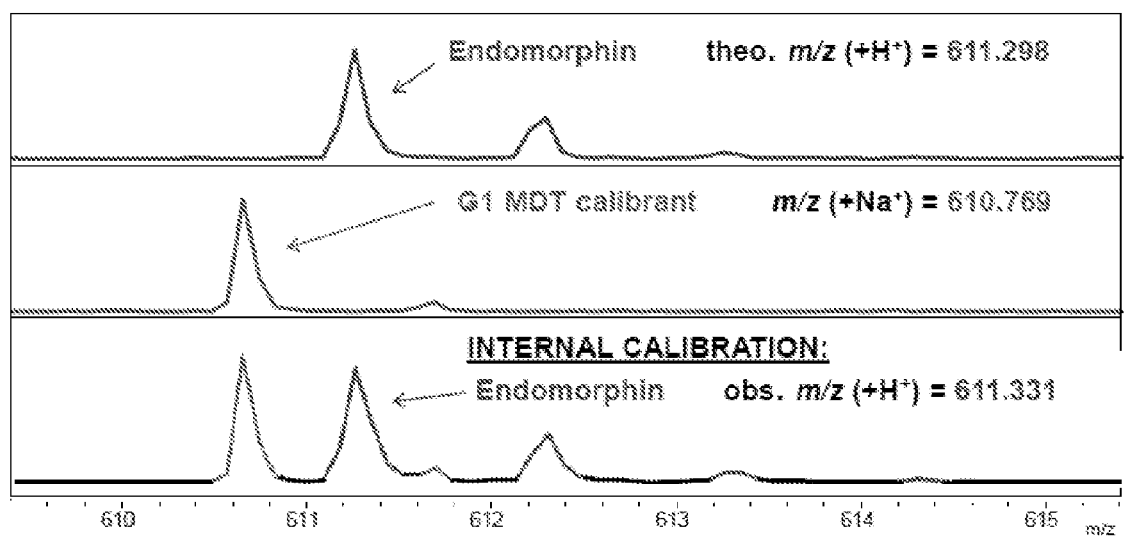
FIG. 28 shows the results of an internal calibration test of iodo-core dendrimer 2 against representative peptide Endomorphin I.

To further verify the utility of the iodo-core calibrants of the present disclosure in acquiring accurate MALDI-TOF data with high mass resolution, peptide Endomorphin I (H-Try-Pro-Trp-Phe-NH$_2$), having the formula C$_{34}$H$_{38}$N$_6$O$_5$ was used in an internal calibration test wherein first generation dendrimer was mixed with Endomorphin I (H-Try-Pro-Trp-Phe-NH$_2$, C$_{34}$H$_{38}$N$_6$O$_5$). As demonstrated in FIG. 28, the peak of the first generation iodo-core calibrant is distinct from the Endomorphin I peak.

In another embodiment, the dendrimer calibrants may be tuned to include an amine core. During ionization of the analyte, one counterion is attached per molecule. These counterions include, for example, H, Na, and K. It is desirable, as a calibrant, for the core molecule of the dendrimer to be compatible with various counterions. Because amines have an unbounded pair of electrons, they readily attract a hydrogen ion. As such, a core molecule containing an amine will readily attract a hydrogen counterion. Triethanolamine may be used as an amine core, as shown in Formula 10. Alternatives to triethanolamine that are speculated to also readily attract hydrogen counterions are those shown in Formula 11 and Formula 12.

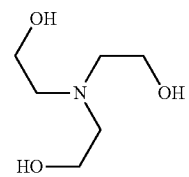

Formula 10

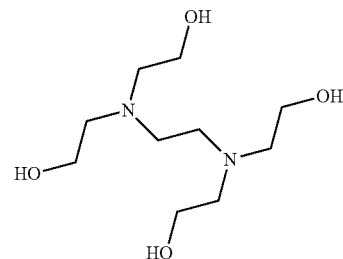

Formula 11

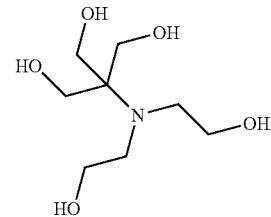

Formula 12

Example 26

Synthesis of Amine-Core Calibrants

Figure 29:
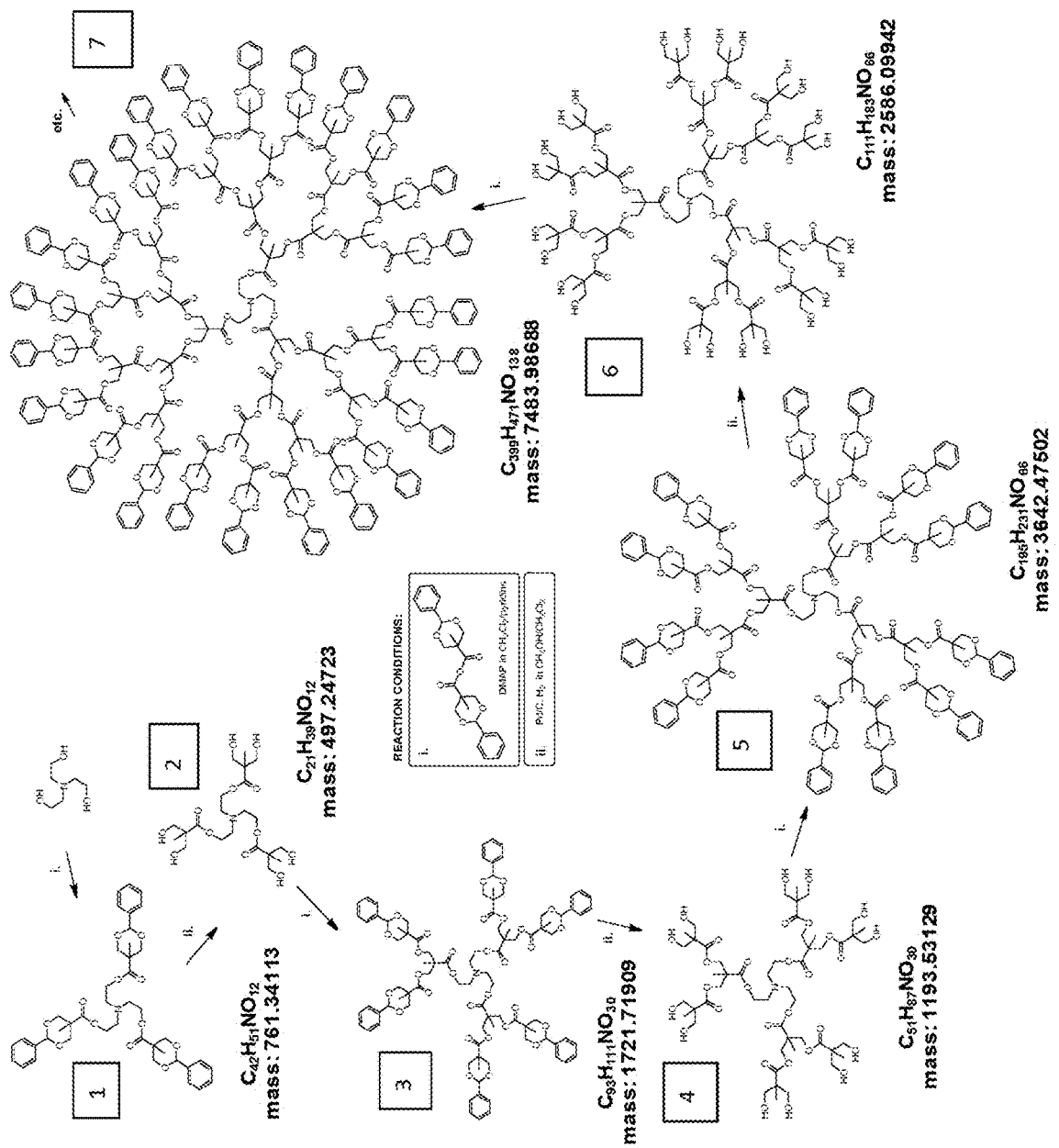
FIG. 29 is a schematic diagram showing the synthesis of tri-functional "C-3" amine-core calibrants of the present disclosure.

The amine-core dendrimer species of this EXAMPLE 26 are shown in FIG. 29.

Synthesis of C3-([G-1]Ph)$_3$, dendrimer 1 of FIG. 29: Triethanolamine, was esterified following the General Dendronization Procedure of EXAMPLE 3, using the benzylidene-protected Bis-MPA anhydride of EXAMPLE 2 and DMAP to afford C3-([G-1]Ph)$_3$. Molecular Formula: C$_{42}$H$_{51}$NO$_{12}$. MALDI-TOF MS: Theoretical Exact MW: [M+H]$^+$ m/z=762.34893. Observed MW: [M+H]$^+$ m/z=762.04.

Synthesis of C3-([G-1]OH$_2$)$_3$, dendrimer 2 of FIG. 29: The benzylidene protected dendrimer 1 was deprotected using 5% Pd(OH)$_2$/C and hydrogen gas following the General Deprotection Procedure of EXAMPLE 4 to afford C3-([G-1]OH$_2$)$_3$. Molecular Formula: C$_{21}$H$_{39}$NO$_{12}$. MALDI-TOF MS: Theoretical Exact MW: [M+H]$^-$ m/z=498.25505. Observed MW: [M+H]$^+$ m/z=to be determined.

Synthesis of C3-([G-2]Ph$_2$)$_3$, dendrimer 3 of FIG. 29: The hydroxylated dendrimer 2, was esterified following the General Dendronization Procedure of EXAMPLE 3, using the benzylidene-protected Bis-MPA anhydride of EXAMPLE 2 and DMAP to afford C3-([G-2]Ph$_2$)$_3$. Molecular Formula: C$_{93}$H$_{111}$NO$_{30}$, MALDI-TOF MS: Theoretical Exact MW: [M+H]$^+$ m/z=1722.72692. Observed MW: [M+H]$^+$ m/z=1722.628.

Synthesis of C3-([G-2]OH$_4$)$_3$, dendrimer 4 of FIG. 29: The benzylidene protected dendrimer 3 was deprotected using 5% Pd(OH)$_2$/C and hydrogen gas following the General Deprotection Procedure of EXAMPLE 4, to afford C3-([G-2]OH$_4$)$_3$. Molecular Formula: C$_{51}$H$_{87}$NO$_{30}$. MALDI-TOF MS: Theoretical Exact MW: [M+H]$^+$ m/z=1194.53912. Observed MW: [M+H]$^+$ m/z=119427.

Synthesis of C3-([G-3]Ph$_4$)$_3$, dendrimer 5 of FIG. 29: The hydroxylated dendrimer 4, was esterified following the General Dendronization Procedure of EXAMPLE 3, using the benzylidene-protected Bis-MPA anhydride of EXAMPLE 2 and DMAP to afford C3-([G-3]Ph$_4$)$_3$. Molecular Formula: C$_{195}$H$_{231}$NO$_{66}$. MALDI-TOF MS: Theoretical Exact MW: [M+H]$^+$ m/z=3643.48285. Observed MW: [M+H]$^+$ m/z=3641.413.

Synthesis of C3-([G-3]OH$_8$)$_3$, dendrimer 6 of FIG. 29: The benzylidene protected dendrimer 5 was deprotected using 5% Pd(OH)$_2$/C and hydrogen gas following the General Deprotection Procedure of EXAMPLE 23, to afford C3-([G-3]OH$_8$)$_3$. Molecular Formula: C$_{111}$H$_{183}$NO$_{66}$. MALDI-TOF MS: Theoretical Exact MW: [M+H]$^+$ m/z=2587.10724 Observed MW: [M+H]$^+$ m/z=2587.19.

Synthesis of C3-([G-4]Ph$_8$)$_3$, dendrimer 7 of FIG. 29: The hydroxylated dendrimer 6, was esterified following the General Dendronization Procedure of EXAMPLE 3, using the benzylidene-protected Bis-MPA anhydride of EXAMPLE 2 and DMAP to afford C3-([G-4]Ph$_8$)$_3$. Molecular Formula: C$_{111}$H$_{183}$NO$_{66}$. MALDI-TOF MS: Theoretical Exact MW: [M+H]$^+$ m/z=7484.99471. Observed MW: [M+H]$^+$ m/z=7480.

Figure 30:
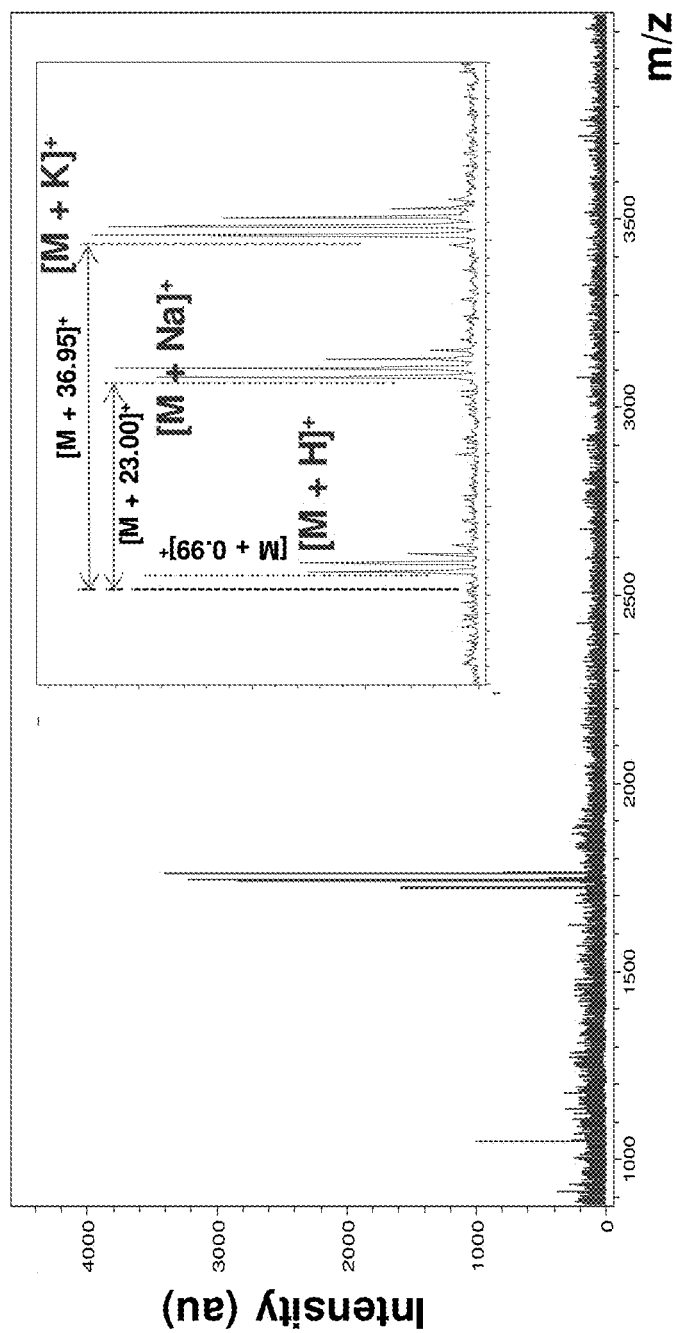
FIG. 30 shows the results of a MALDI-TOF analysis of amine core dendrimer 2 of the present disclosure.
Figure 31:
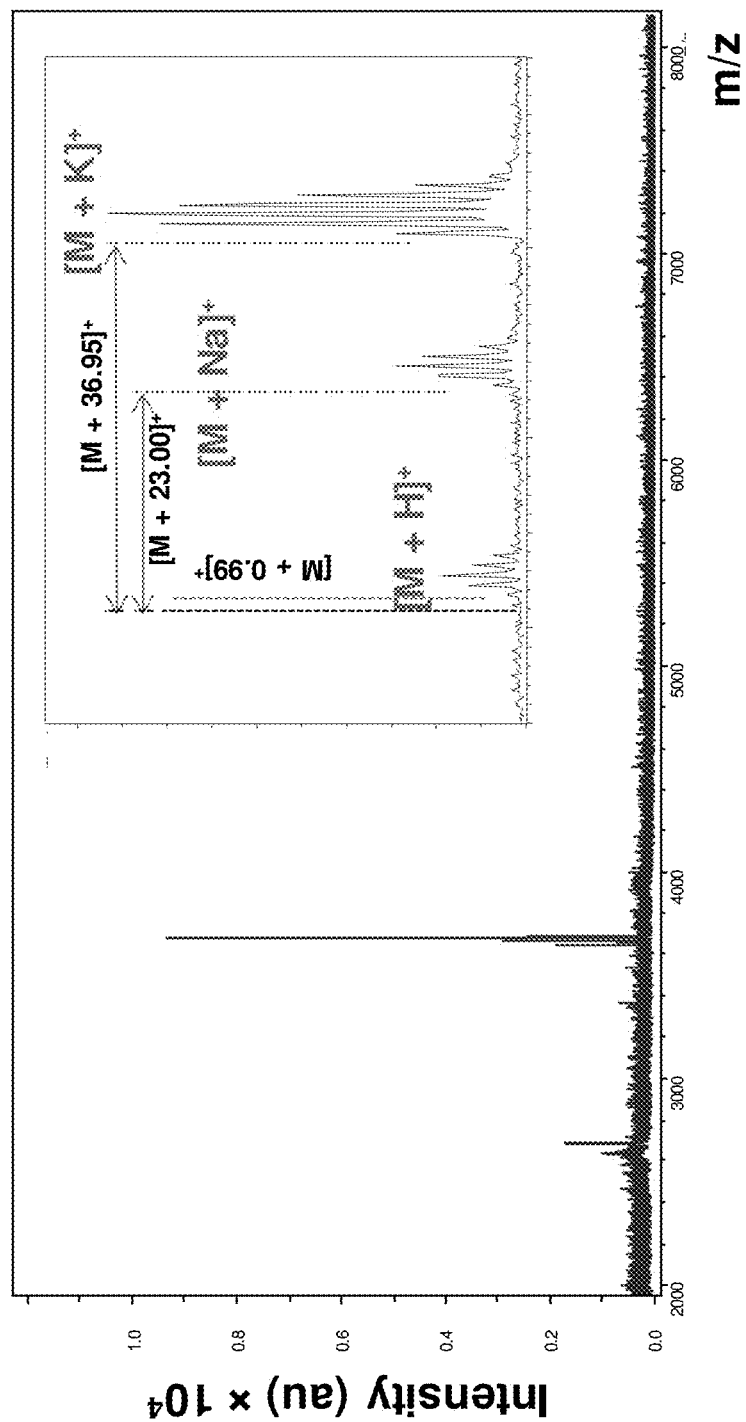
FIG. 31 shows the results of a MALDI-TOF analysis of amine core dendrimer 4 of the present disclosure.

FIG. 30 shows a MALDI-TOF mass spectra of the amine core dendrimer 2 in a α-Cyano-4-hydroxycinnamic acid (CHCA) matrix, and showing the mass spectra peaks of the ionized dendrimer. FIG. 31 shows a MALDI-TOF mass spectra of the amine core dendrimer 4 in a CHCA matrix, and showing the mass spectra peaks of the ionized dendrimer. As can be appreciated from FIGS. 30 and 31, the second and third generation amine core dendrimer calibrants are readily compatible with various counterions. Thus, these dendrimers with an amine molecular core result in a more useful synthetic dendritic calibrant.

Figure 32:
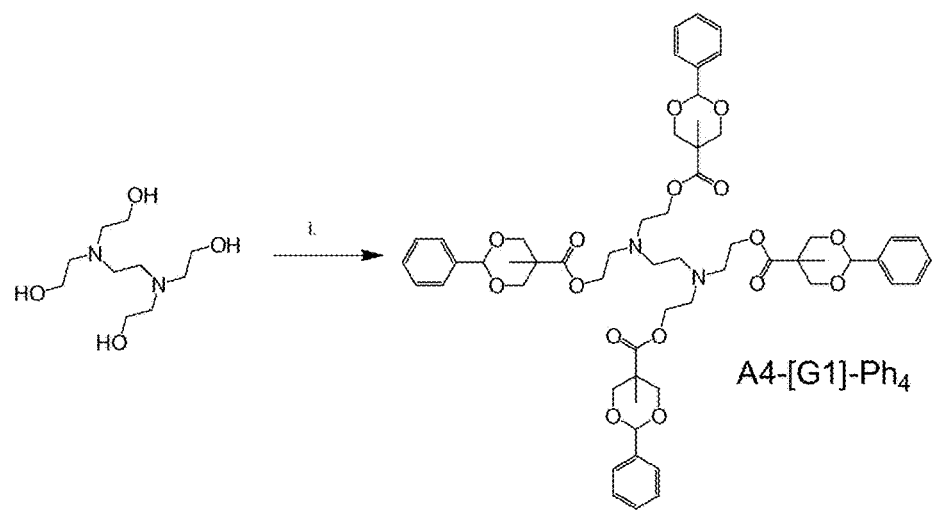
FIG. 32 is a schematic diagram showing the dendronization of N,N,N',N'-Tetrakis(2-hydroxyethyl) ethylenediamine to create C4-[G1]-Ph$_4$.
Figure 33:
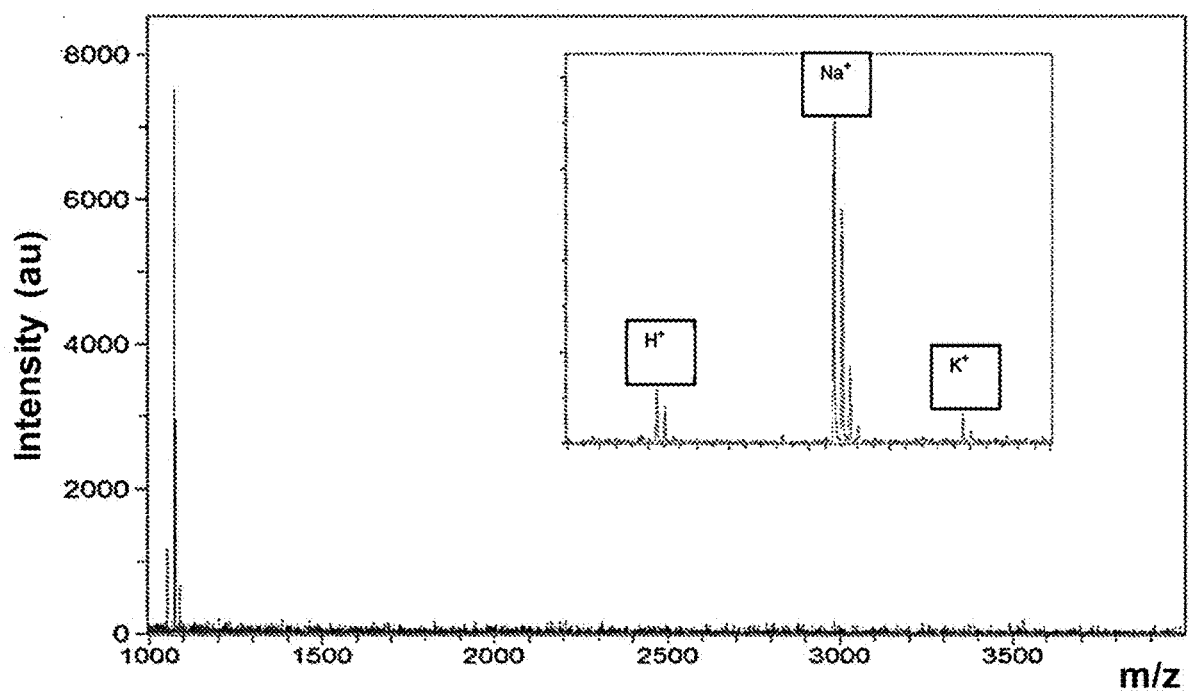
FIG. 33 shows the results of a MALDI-TOF analysis of amine core dendrimer C4-[G1]-Ph$_4$ of FIG. 32.

An alternate exemplary amine-core dendrimer species is shown in FIG. 32 wherein N,N,N',N'-Tetrakis(2-hydroxyethyl) ethylenediamine was esterified following the General Dendronization Procedure of EXAMPLE 3, using the benzylidene-protected Bis-MPA anhydride of EXAMPLE 2 and DMAP to afford C4-([G-1]Ph)$_4$. FIG. 33 shows a MALDI-TOF mass spectra of C4-([G-1]Ph)$_4$ in a α-Cyano-4-hydroxycinnamic acid (CHCA) matrix, and showing the mass spectra peaks of the ionized dendrimer. As can be appreciated from FIG. 33, this amine core dendrimer calibrants is readily compatible with various counterions. Thus, dendrimers with an amine molecular core result in a more useful synthetic dendritic calibrant.

Figure 34:
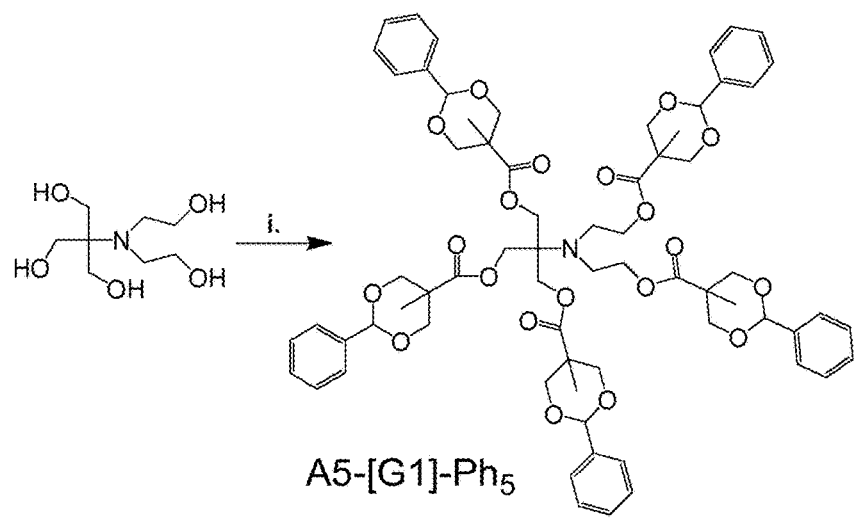
FIG. 34 is a schematic diagram showing the dendronization of bis-tris to create C5-[G1]-Ph$_5$.
Figure 35:
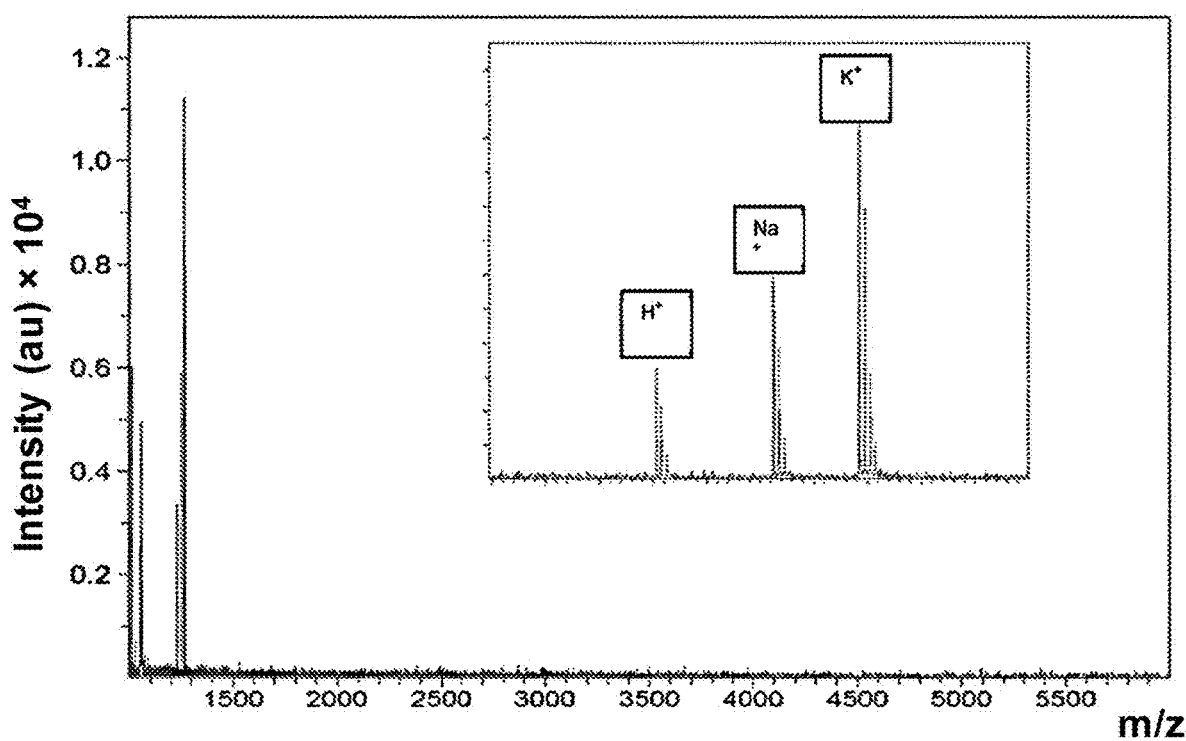
FIG. 35 shows the results of a MALDI-TOF analysis of amine core dendrimer C5-[G1]-Ph$_5$ of FIG. 34.

Yet another alternate exemplary amine-core dendrimer species is shown in FIG. 34 wherein bis-tris was esterified following the General Dendronization Procedure of EXAMPLE 3, using the benzylidene-protected Bis-MPA anhydride of EXAMPLE 2 and DMAP to afford to C5-[G1]-Ph$_5$. FIG. 35 shows a MALDI-TOF mass spectra of C5-([G-1]Ph)$_5$, in a α-Cyano-4-hydroxycinnamic acid (CHCA) matrix, and showing the mass spectra peaks of the ionized dendrimer. As can be appreciated from FIG. 35, this amine core dendrimer calibrants is readily compatible with various counterions. Thus, dendrimers with an amine molecular core result in a more useful synthetic dendritic calibrant.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A composition comprising:
a first dendrimer comprising a first core molecule, wherein said first core molecule is selected from the group consisting of: a molecule comprising between 1 and 8 alcohol functionalities, a molecule comprising between 1 and 8 amine functionalities, and a molecule comprising at least one amine functionality and at least one alcohol functionality wherein the combined number of amine and alcohol functionalities of said first core molecule is at least 2 but no greater than 8; and
a second dendrimer comprising a second core molecule, wherein said second core molecule is selected from the group consisting of: a molecule comprising between 1 and 8 alcohol functionalities, a molecule comprising between 1 and 8 amine functionalities, and a molecule comprising at least one amine functionality and at least one alcohol functionality wherein the combined number of amine and alcohol functionalities of said second core molecule is at least 2 but no greater than 8;
wherein said first core molecule has a different number of total alcohol functionalities and amine functionalities than said second core molecule;
wherein the first dendrimer and the second dendrimer each have a mass defect falling within a scarcine valley of an average amino acid; and
wherein the first core molecule and the second core molecule each comprise a mass defect marker selected from the group consisting of phosphorous, iodine, bromine, and combinations thereof.

2. A method of calibrating a mass spectrometer, the method comprising:
providing a composition comprising
a first dendrimer comprising a first core molecule, wherein said first core molecule is selected from the group consisting of: a molecule comprising between 1 and 8 alcohol functionalities, a molecule comprising between 1 and 8 amine functionalities, and a molecule comprising at least one amine functionality and at least one alcohol functionality, wherein the combined number of amine and alcohol functionalities of said first core molecule is at least 2 but no greater than 8, and the first core molecule comprises three iodine atoms; and a second dendrimer comprising a second core molecule, wherein said second core molecule is selected from the group consisting of: a molecule comprising between 1 and 8 alcohol functionalities, a molecule comprising between 1 and 8 amine functionalities, and a molecule comprising at least one amine functionality and at least one alcohol functionality wherein the combined number of amine and alcohol functionalities of said second core molecule is at least 2 but no greater than 8;

wherein said first core molecule has a different number of total alcohol functionalities and amine functionalities than said second core molecule; and wherein said composition has physical properties;

ionizing at least a portion of said composition;

collecting data from said ionized portion of said composition; and relating said data to said physical properties.

3. A method of calibrating a mass spectrometer, the method comprising:

providing a composition comprising a first dendrimer comprising a first core molecule, wherein said first core molecule is selected from the group consisting of: a molecule comprising between 1 and 8 alcohol functionalities, a molecule comprising between 1 and 8 amine functionalities, and a molecule comprising at least one amine functionality and at least one alcohol functionality wherein the combined number of amine and alcohol functionalities of said first core molecule is at least 2 but no greater than 8; and a second dendrimer comprising a second core molecule, wherein;

said second core molecule comprises a subsequent generation dendrimer of said first core molecule;

the first dendrimer and the second dendrimer each have a mass defect falling within a scarcine valley of an average amino acid;

the first core molecule and the second core molecule each comprise a mass defect marker selected from the group consisting of phosphorous, iodine, bromine, and combinations thereof; and said composition has physical properties;

ionizing at least a portion of said composition;

collecting data from said ionized portion of said composition; and relating said data to said physical properties.

4. The method of claim 3, wherein said first core molecule comprises three iodine atoms.

5. The method of claim 3, wherein the first core molecule comprises a tertiary amine functionality.

6. The method of claim 3, wherein the mass defect marker for the first core molecule and for the second core molecule is iodine.

7. The method of claim 3, wherein the first dendrimer and the second dendrimer each have a mass defect distinct from an averagine ridge of an average amino acid.

8. The method of claim 7, wherein the average amino acid has an average chemical formula of $C_{4.9384}H_{7.7583}N_{1.3577}O_{1.4773}S_{0.0417}$ with a molecular weight of 111.05431.

9. The method of claim 7, wherein the first dendrimer and the second dendrimer each have a mass difference of about 0.2 amu about 0.5 amu relative to the averagine ridge.

10. The method of claim 7, wherein the first dendrimer and the second dendrimer each have a mass difference of about 0.3 amu to about 0.5 amu relative to the averagine ridge.

11. The method of claim 7, wherein the first dendrimer and the second dendrimer each have a mass difference of about 0.4 amu to about 0.5 amu relative to the averagine ridge.

12. The method of claim 7, wherein the first dendrimer and the second dendrimer each have a mass difference of about 0.5 amu relative to the averagine ridge.

13. The composition of claim 1, wherein at least one of the first core molecule and the second core molecule comprises a tertiary amine functionality.

14. The composition of claim 1, wherein the mass defect marker for the first core molecule and for the second core molecule is iodine.

15. The composition of claim 1, wherein the first dendrimer and the second dendrimer each have a mass defect distinct from an averagine ridge of an average amino acid.

16. The composition of claim 15, wherein the average amino acid has an average chemical formula of $C_{4.9384}H_{7.7583}N_{1.3577}O_{1.4773}S_{0.0417}$ with a molecular weight of 111.05431.

17. The composition of claim 15, wherein the first dendrimer and the second dendrimer each have a mass difference of about 0.2 amu about 0.5 amu relative to the averagine ridge.

18. The composition of claim 15, wherein the first dendrimer and the second dendrimer each have a mass difference of about 0.3 amu to about 0.5 amu relative to the averagine ridge.

19. The composition of claim 15, wherein the first dendrimer and the second dendrimer each have a mass difference of about 0.4 amu to about 0.5 amu relative to the averagine ridge.

20. The composition of claim 15, wherein the first dendrimer and the second dendrimer each have a mass difference of about 0.5 amu relative to the averagine ridge.

* * * * *